US011535651B2

(12) United States Patent
Harris et al.

(10) Patent No.: US 11,535,651 B2
(45) Date of Patent: Dec. 27, 2022

(54) HEPATITIS B NANOPARTICLE-BASED VACCINE FOR INFLUENZA VIRUS

(71) Applicant: THE USA, AS REPRESENTED BY THE SECRETARY, DEPT. OF HEALTH AND HUMAN SERVICES, Bethesda, MD (US)

(72) Inventors: Audray K. Harris, Bethesda, MD (US); Dustin M. McCraw, North Bethesda, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 16/635,240

(22) PCT Filed: Aug. 2, 2018

(86) PCT No.: PCT/US2018/045032
§ 371 (c)(1),
(2) Date: Jan. 30, 2020

(87) PCT Pub. No.: WO2019/028266
PCT Pub. Date: Feb. 7, 2019

(65) Prior Publication Data
US 2020/0369730 A1  Nov. 26, 2020

Related U.S. Application Data

(60) Provisional application No. 62/540,474, filed on Aug. 2, 2017.

(51) Int. Cl.
*C07K 14/11*   (2006.01)
*A61P 31/16*   (2006.01)
*C12N 7/00*    (2006.01)
*A61K 39/145*  (2006.01)

(52) U.S. Cl.
CPC ............ *C07K 14/11* (2013.01); *A61K 39/145* (2013.01); *A61P 31/16* (2018.01); *C12N 7/00* (2013.01)

(58) Field of Classification Search
None
See application file for complete search history.

(56) References Cited

FOREIGN PATENT DOCUMENTS

| EP | 1897887 | 3/2008 |
|----|---------|--------|
| WO | WO 2016/087863 | 6/2016 |

OTHER PUBLICATIONS

Schneemann et al., A Virus-Like Particle That Elicits CrossReactive Antibodies to the Conserved Stem of Influenza Virus Hemagglutinin, 2012, Journal of Virology, vol. 86, No. 21, pp. 11686-11697.*

Birnbaum et al. "Hepatitis B Virus Nucleocapsid Assembly: Primary Structure Requirements in the Core Protein," Journal of Virology, Jul. 1990, vol. 64, No. 7, pp. 3319-3330.

Chen et al. "Protection against Multiple Subtypes of Influenza Viruses by Virus-Like Particle Vaccines Based on a Hemagglutinin Conserved Epitope," Biomed Research International, vol. 2015, Jan. 2015, 901817, 12 pages.

Corti et al. "Broadly Neutralizing Antiviral Antibodies," Annual Review of Immunology, Mar. 2013, vol. 31, No. 1, pp. 705-742.

Kazaks et al. "Production and purification of chimeric HBc virus-like particles carrying influenza virus LAH domain as vaccine candidates," BMC Biotechnology, 2017, vol. 17, No. 1, 79, 12 pages.

Koschel et al. "Hepatitis B Virus Core Gene Mutations Which Block Nucleocapsid Envelopment," Journal of Virology, Jan. 2000, vol. 74, No. 1, pp. 1-7.

Lange et al. "Hepatitis C Virus Hypervariable Region 1 Variants Presented on Hepatitis B Virus Capsid-Like Particles Induce Cross-Neutralizing Antibodies," PLOSOne, Jul. 2014, vol. 9, No. 7, e102235, 10 pages.

Nassal et al. "A fusion product of the complete Borrelia burgdorferi outer surface protein A (OspA) and the hepatitis B virus capsid protein is highly immunogenic and induces protective immunity similar to that seen with an effective lipidated OspA vaccine formula," European Journal of Immunology, 2005, vol. 35, pp. 655-665.

Peyret et al. "Tandem Fusion of Hepatitis B Core Antigen Allows Assembly of Virus-Like Particles in Bacteria and Plants with Enhanced Capacity to Accommodate Foreign Proteins," PLOSOne, Apr. 2015, vol. 10, No. 4, e0120751, 20 pages.

Schneemann et al. "A Virus-Like Particle That Elicits Cross-Reactive Antibodies to the Conserved Stem of Influenza Virus Hemagglutinin," Journal of Virology, Nov. 2012, vol. 86, No. 21, pp. 11686-11697.

Skamel et al. "Hepatitis B Virus Capsid-like Particles Can Display the Complete, Dimeric Outer Surface Protein C and Stimulate Production of Protective Antibody Responses against Borrelia burgdorferi Infection," The Journal of Biological Chemistry, Jun. 2006, vol. 281, No. 25, pp. 17474-17481.

Walker et al. "Splitcore: An exceptionally versatile viral nanoparticle for native whole protein display regardless of 3D structure," Scientific Reports, Jun. 2011, vol. 1, No. 5, 8 pages.

(Continued)

*Primary Examiner* — Benjamin P Blumel
(74) *Attorney, Agent, or Firm* — Klarquist Sparkman, LLP

(57) ABSTRACT

Fusion proteins comprising one or more portions of hepatitis virus core antigen (HBcAg) fused to immunogenic portions of influenza virus hemagglutinin (HA) protein, and nanoparticles (virus-like particles) formed from such proteins, nucleic acid molecules encoding such proteins, methods of making such nanoparticles, methods of using the disclosed nanoparticles to vaccinate an individual against influenza virus, and antibodies elicited by vaccination of a mammal with the disclosed nanoparticles.

23 Claims, 36 Drawing Sheets
Specification includes a Sequence Listing.

(56) References Cited

OTHER PUBLICATIONS

International Preliminary Report on Patentability for International (PCT) Patent Application No. PCT/US2018/045032, dated Feb. 13, 2020 9 pages.
International Search Report and Written Opinion prepared by the European Patent Office dated Oct. 22, 2018, for International Application No. PCT/US2018/045032.

* cited by examiner

FIG. 1A Helix A of HA2 involved in stem epitopes
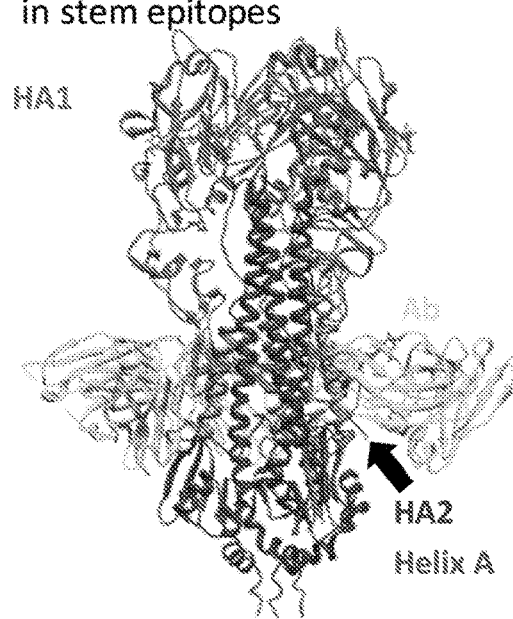
FIG. 1B capsid protein (HBV)
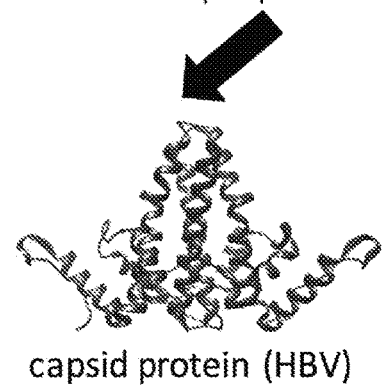
Epitope insertion site replaces immunodominant site of capsid protein
capsid protein (HBV)
FIG. 1C Capsid particle
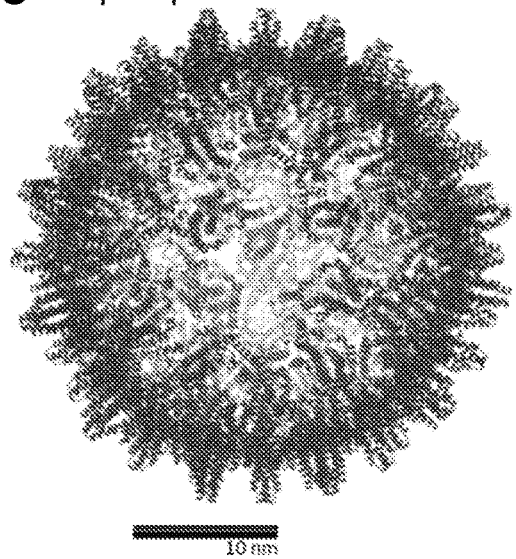
capsid proteins can from particles
FIG. 1D
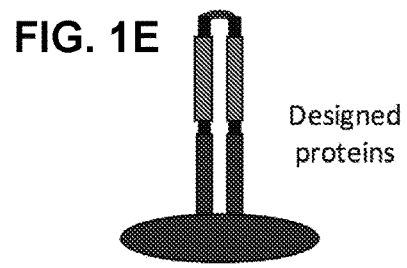
capsid prot

Schematics of constructs
FIG. 2A
capsid
*c1
FIG. 2B
NP st01
FIG. 2C
NP st02
FIG. 2D
Diagram Key
 (Capsid scaffold)
 Helix-A
 Linkers (flanking sequencing)
 Insertion site (capsid)
 Epitope tag (detection)

capsid

NPst01

NPst02

Capsid: Purification and particle formation

NPst01: Purification and particle formation

NPst02: Purification and particle formation
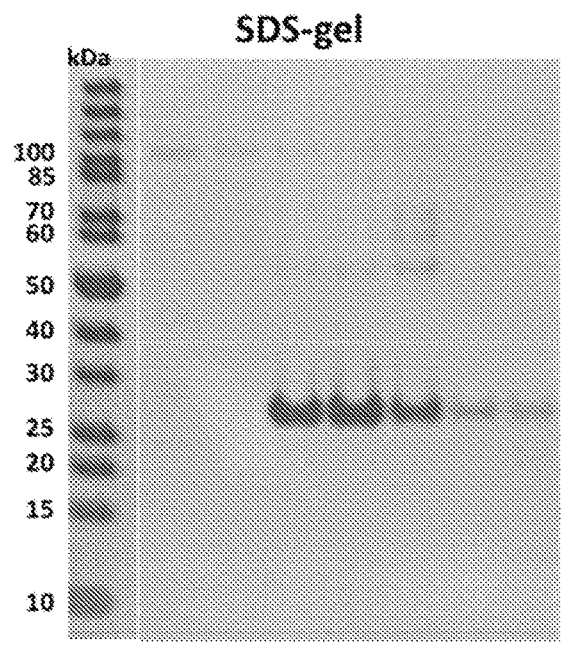
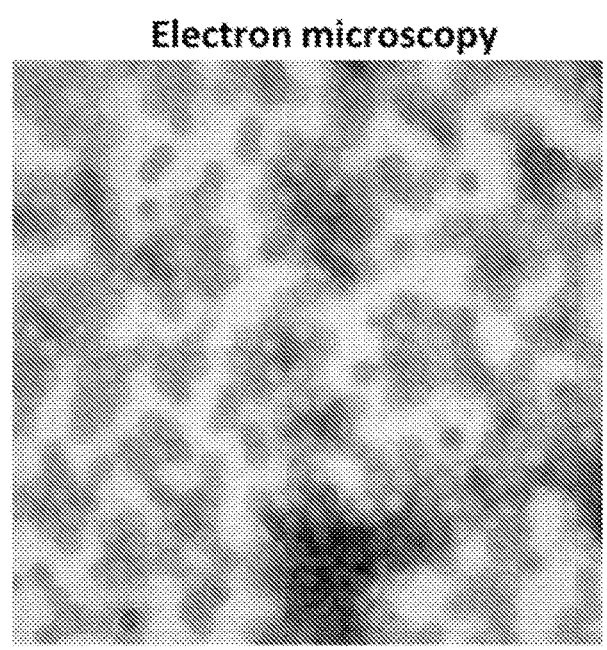
FIG. 6A
FIG. 6B

Nanoparticles show reactivity with anti-H1 HA antibodies
Dot blot

| antigens | 1.0 | 0.5 | 0.250 | 0.125 | 0.062 | 0.031 | 0.015 | 0.007 | 0.003 µg |
|---|---|---|---|---|---|---|---|---|---|
| capsid | | | | | | | | | |
| capsid | | | | | | | | | |
| NP st01 | | | | | | | | | |
| NP st01 | | | | | | | | | |
| NP st02 | | | | | | | | | |
| NP st02 | | | | | | | | | |
| BSA | | | | | | | | | |

Primary antibody : Anti H1 HA pAb

FIG. 7

Nanoparticle with insertion of epitope abrogates immunodominant epitope of capsid scaffold

Dot blot

| antigens | 6 µg | 2 µg | 200 ng | 20 ng | 2 ng | 200 pg | 20 pg | 2 pg |
|---|---|---|---|---|---|---|---|---|
| capsid | ● | ● | | | | | | |
| NP st02 | | | | | | | | |
| NP st02 | | | | | | | | |
| H1 HA | | | | | | | | |
| H1 HA | | | | | | | | |

Primary antibody: anti-capsid mAb88
mAb 88 (recognizes the immunodominant
Loop, epitope c1 of the capsid)

FIG. 8

Immunization and challenge (mice)

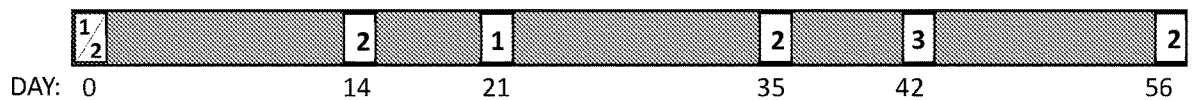

DAY:  0     14    21         35    42         56

| | |
|---|---|
| 1 | = Intramuscular injection (Antigen, Antigen + Adjuvant, or Vehicle) |
| 2 | = Blood collection (Tail Vein or Cardiac puncture) |
| 3 | = Challenge by Intranasal Virus exposure (A/California/07/2009) |

BALB/c mice (n=5) per group   Injected twice at weeks 0 and 3
Group 1: PBS                  Intramuscular route
Group 2: NP-st02 + adjuvant   Challenge: Intranasal
Group 3: NP-st02
50μg NP-st02
SAS (Ribi) adjuvant

FIG. 9

Immunogenicity: Nanoparticle (NP-st02) elicits antibodies that bind nanoparticles and influenza hemagglutinin ■ Control (Saline)  □ Nanoparticle  ▨ Nanoparticle + Adjuvant

FIG. 10A        FIG. 10B

Immunization with NP-st02 immunogen
protects mice against lethal challenge

FIG. 11A

— PBS Control
··· Nanoparticle

80% protection

FIG. 11B

— PBS Control
··· Nanoparticle + adjuvant

Immunization with NP-st02 immunogen
reduces weight lost of mice against lethal challenge

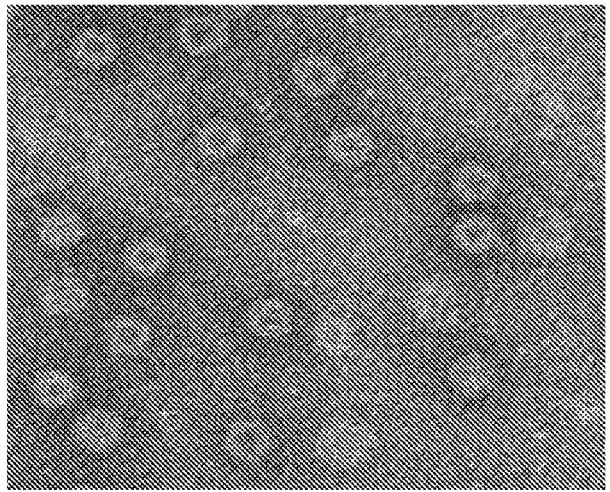
FIG. 13A 4°C
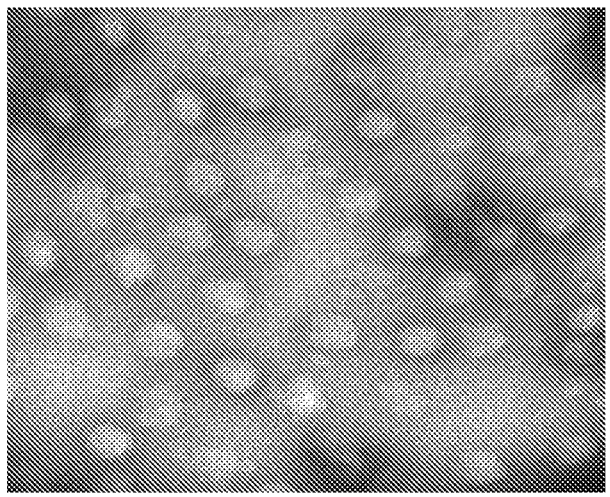
FIG. 13B 40°C
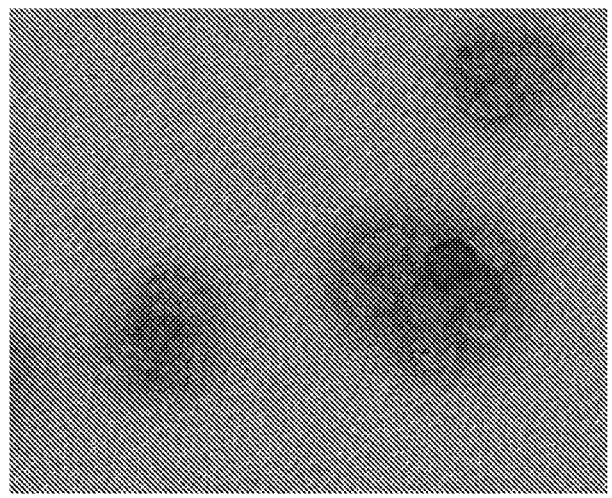
FIG. 13C 90°C

|     | H1 | H2 | H3 | H4 | H5 | H6 | H7 | H8 | H9 | H10 | H11 | H12 | H13 | H14 | H15 | H16 |
|-----|----|----|----|----|----|----|----|----|----|-----|-----|-----|-----|-----|-----|-----|
| H1  |    | 86 | 64 | 68 | 73 | 77 | 68 | 68 | 59 | 68  | 55  | 59  | 59  | 68  | 68  | 59  |
| H2  |    |    | 55 | 59 | 86 | 86 | 64 | 64 | 64 | 64  | 68  | 64  | 73  | 59  | 64  | 68  |
| H3  |    |    |    | 95 | 50 | 55 | 82 | 55 | 50 | 86  | 50  | 55  | 59  | 95  | 86  | 50  |
| H4  |    |    |    |    | 50 | 55 | 86 | 55 | 50 | 91  | 50  | 55  | 59  | 100 | 91  | 55  |
| H5  |    |    |    |    |    | 91 | 55 | 68 | 68 | 55  | 73  | 64  | 77  | 50  | 55  | 64  |
| H6  |    |    |    |    |    |    | 59 | 73 | 77 | 59  | 73  | 68  | 77  | 55  | 59  | 64  |
| H7  |    |    |    |    |    |    |    | 59 | 55 | 95  | 55  | 55  | 64  | 86  | 95  | 59  |
| H8  |    |    |    |    |    |    |    |    | 82 | 59  | 73  | 59  | 68  | 55  | 59  | 59  |
| H9  |    |    |    |    |    |    |    |    |    | 55  | 82  | 68  | 73  | 50  | 55  | 64  |
| H10 |    |    |    |    |    |    |    |    |    |     | 55  | 55  | 64  | 91  | 100 | 59  |
| H11 |    |    |    |    |    |    |    |    |    |     |     | 55  | 82  | 50  | 55  | 64  |
| H12 |    |    |    |    |    |    |    |    |    |     |     |     | 64  | 55  | 55  | 55  |
| H13 |    |    |    |    |    |    |    |    |    |     |     |     |     | 59  | 64  | 82  |
| H14 |    |    |    |    |    |    |    |    |    |     |     |     |     |     | 91  | 55  |
| H15 |    |    |    |    |    |    |    |    |    |     |     |     |     |     |     | 59  |
| H16 |    |    |    |    |    |    |    |    |    |     |     |     |     |     |     |     |

Library Design

> 50,000 HA sequences downloaded

> 36,000 epitopes categorized

18 IAV subtypes characterized
2 influenza B lineages 30 sequences
selected

Influenza
database

Bioinformatics

Library

Fig. 17B

Identity

| Percent identities of library to database sequences | Corresponding coverage of influenza database epitopes |
|---|---|
| 100% | 62.50% |
| 95% | 28.60% |
| 91% | 5.10% |
| 86% | 2.50% |
| 82% | 0.90% |
| 77% | 0.40% |

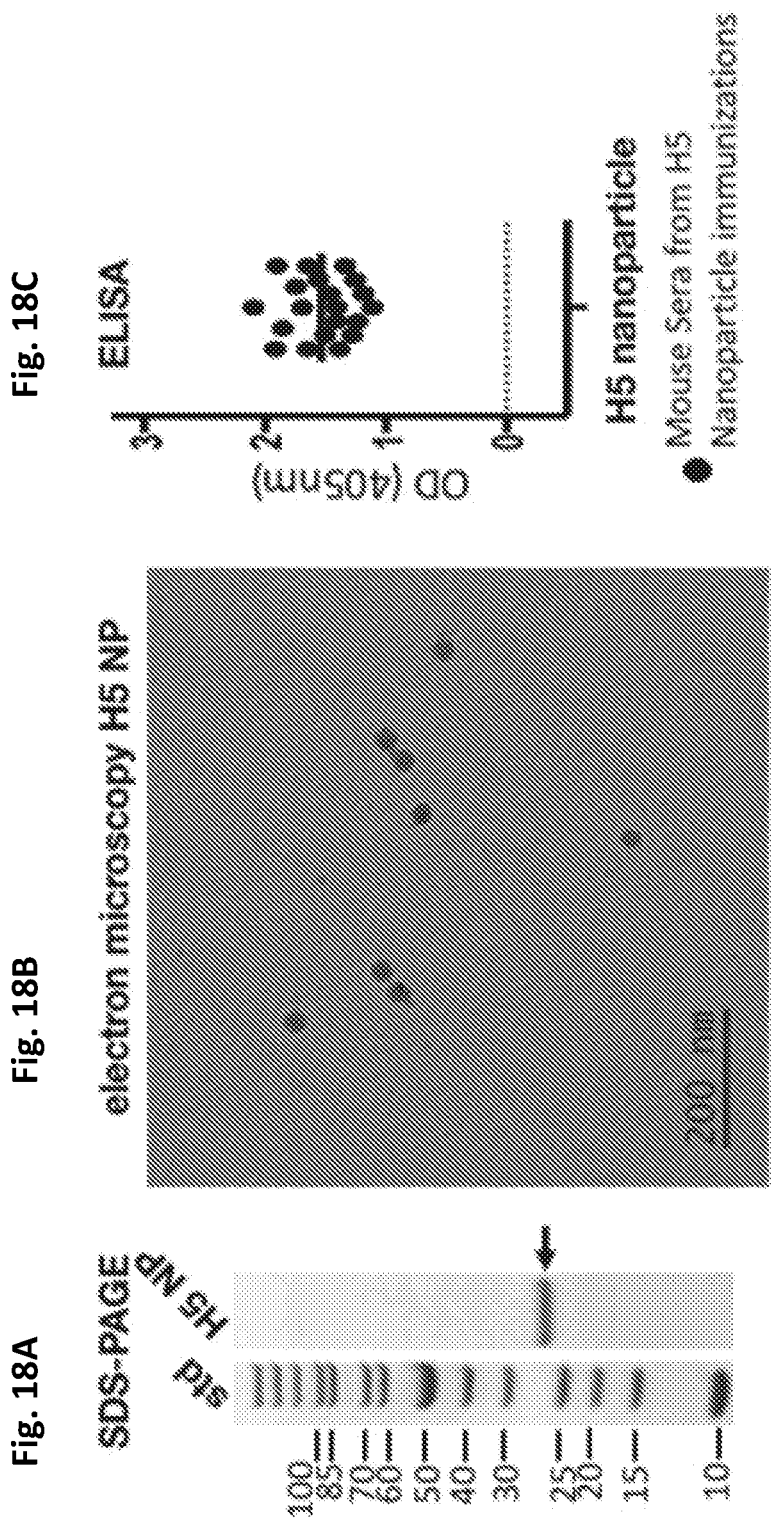

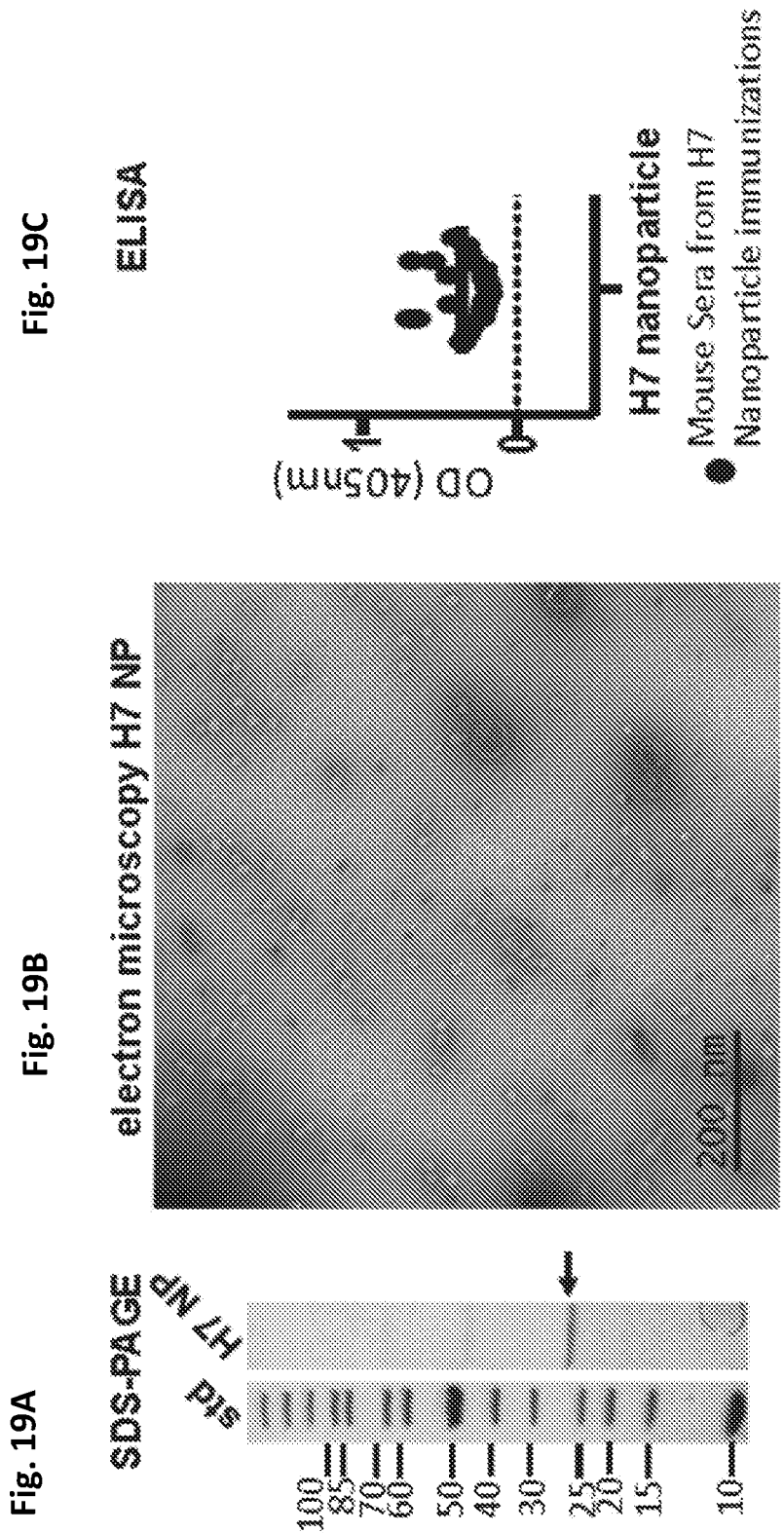

α H7 NP sera

Nanoparticle cross-reactivity to H1
(A/Cali/07/2009)

$t(3) = 3.293, p = 0.0460$

H1 HA    PBS

Fig. 20C

α H5 NP sera

Nanoparticle cross-reactivity to H1
(A/Cali/07/2009)

t(3)=1.65, p=0.1976
N.S.

OD 405nm

H1 HA    PBS

Fig. 20E

HEPATITIS B NANOPARTICLE-BASED VACCINE FOR INFLUENZA VIRUS

CROSS REFERENCE TO RELATED APPLICATION

This application is a national stage application under 35 U.S.C. 371 of PCT Application No. PCT/US2018/045032 having an international filing date of 2 Aug. 2018, which designated the United States, which PCT application claimed the benefit of U.S. Provisional Patent Application Ser. No. 62/540,474 filed on 2 Aug. 2017, the disclosures of each of which are incorporated herein by reference in their entireties.

REFERENCE TO SEQUENCE LISTING

This application contains a Sequence Listing submitted as an electronic text file named "6137NIAID-66-PCT_Sequence_Listing_ST25.txt", having a size in bytes of 95 KB, and created on Aug. 2, 2018. The information contained in this electronic file is hereby incorporated by reference in its entirety pursuant to 37 CFR § 1.52(e)(5).

FIELD OF TECHNOLOGY

The invention relates to fusion proteins comprising one or more portions of hepatitis virus core antigen (HBcAg) fused to immunogenic portions of influenza virus hemagglutinin (HA) protein, and nanoparticles (virus-like particles (VLPs)) formed from such proteins, nucleic acid molecules encoding such proteins, methods of making such nanoparticles, and methods of using the disclosed nanoparticles to vaccinate an individual against influenza virus.

BACKGROUND

Protective immune responses induced by vaccination against influenza virus are primarily directed to the viral hemagglutinin (HA) protein, which is a glycoprotein on the surface of the virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HA1. The globular head of a hemagglutinin protein includes two domains: the receptor binding domain (RBD), an approximately 148-amino acid residue domain that includes the sialic acid binding site, and the vestigial esterase domain, a smaller approximately 75-amino acid residue region just below the RBD. The top part of the RBD adjacent to the 2,6-sialic acid recognition sites includes a large region (amino acids 131-143, 170-182, 205-215 and 257-262, 1918 numbering) (referred to as the RBD-A region) of over 6000 squared angstrom per trimer that is 95% conserved between A/South Carolina/1/1918 (1918 SC) and A/California/04/2009 (2009 CA) pandemic strains. The globular head includes several antigenic sites that include immunodominant epitopes. Antibodies against influenza often target variable antigenic sites in the globular head of HA, which surround a conserved sialic acid binding site, and therefore neutralize only viruses that are antigenically closely related.

Recently, entirely new classes of broadly neutralizing antibodies against influenza viruses were isolated. One class of antibodies recognizes the highly conserved HA stem (Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)). Another class of antibodies precisely recognizes the sialic acid binding site of the RBD on the variable HA head (Whittle, J. R. et al. *Proc Natl Acad Sci USA* 108, 14216-14221 (2011); Krause, J. C. et al. *J Virol* 85, 10905-10908 (2011)). Unlike strain-specific antibodies, those antibodies are capable of neutralizing multiple antigenically distinct viruses (Nabel, G. J. et al. *Nat Med* 16, 1389-1391 (2010)). But robustly eliciting such antibodies with heterologous neutralizing profile by vaccination has been difficult (Steel, J. et al. *MBio* 1, e0018 (2010); Wang, T. T. et al. *PLoS Pathog* 6, e1000796 (2010); Wei, C. J. et al. *Science* 329, 1060-1064 (2010)).

There remains a need for an efficacious influenza vaccine that provides robust protection against influenza virus. In particular, there is a need for an influenza vaccine that protects individuals from heterologous strains of influenza virus, including evolving seasonal and pandemic influenza virus strains of the future. The present invention meets this need by providing a novel hepatitis B virus (HBV)-based nanoparticle influenza vaccine that is easily manufactured, potent, and which elicits broadly neutralizing influenza antibodies.

SUMMARY

The HA2 region of hemagglutinin (HA) comprises an alpha helix called helix A that is part of the epitopes for a number of broadly neutralizing stem antibodies. However, some of the stem epitopes not only involve helix A but also surrounding residues that can abrogate stem antibody binding by acquiring glycosylation sites and antibody-escape mutations. Thus, the present inventors desired to create a smaller epitope footprint, specific to helix A, to use in the preparation of a broad vaccine that induces strong immunological protection against influenza viruses. The inventors have surprisingly discovered that a conserved helix A region of the HA2 stem, fused with a viral capsid elicits a strong immunological response that is protective against challenge with even lethal, pandemic strains of influenza.

Thus, one aspect of this disclosure is a fusion protein selected from the group consisting of: a) a first fusion protein comprising an immunogenic peptide from helix A from the stem region of an influenza hemagglutinin (HA) protein, joined to the carboxyl-terminal end of the α3 helix from a hepatitis B core antigen (HBcAg); and, b) a second fusion protein comprising an immunogenic peptide from helix A from the stem region of an influenza hemagglutinin (HA) protein, joined to the amino-terminal end of the α4 helix from a hepatitis B core antigen (HBcAg). The first fusion protein may form a virus-like particle (VLP) when combined with a HAcAg-C protein. The second fusion protein may form a virus-like particle (VLP) when combined with a HAcAG-N protein. The immunogenic peptide may include an epitope from SEQ ID NO:2 or from a sequence selected from the group consisting of SEQ ID NO:70-SEQ ID NO:99. For example, the immunogenic peptide may include at least six contiguous amino acids from SEQ ID NO:2 or from a sequence selected from the group consisting of SEQ ID NO:70-SEQ ID NO:99. The helix A may include an amino acid sequence at least 50% identical, or 100% identical to SEQ ID NO:2. The HBcAg may include an amino acid sequence at least 50% identical, or 100% identical to SEQ D NO:3. The α3 helix sequence may include an amino acid sequence at least 50% identical, or 100% identical to a sequence selected from the group consisting of SEQ ID NOs:4, 5, 6, 7, and 8.

The α4 helix sequence may include an amino acid sequence at least 50% identical, or 100% identical to a sequence selected from the group consisting of SEQ ID NOs:9, 10, 11, and 12. In these fusion proteins, the immunogenic peptide of the first fusion protein may be joined to the carboxyl-terminal end of a first amino acid sequence comprising at least 30 contiguous amino acid residues from the polypeptide sequence immediately upstream of the c/e1 loop sequence of a HBcAG. The c/e1 loop may have an amino acid sequence selected from the group consisting of SEQ ID NOs:18, 19, 20, and 21. The at least 30 contiguous amino acid residues may be from the polypeptide sequence immediately upstream of any one of amino acid residues 71-82 in SEQ ID NO:3. The at least 30 contiguous amino acid residues may comprise an amino acid sequence at least 50% identical, or 100% identical to a sequence selected from the group consisting of SEQ ID NOs:22, 23, 24, and 25.

In these fusion proteins, the immunogenic peptide of the second fusion protein may be joined to the amino-terminal end of a second amino acid sequence comprising at least 50 contiguous amino acid residues from the polypeptide sequence immediately downstream of the c/e1 loop sequence of a HBcAg. The at least 50 contiguous amino acid residues may be from the polypeptide sequence immediately downstream of any one of amino acid residues 71-82 in SEQ ID NO:3. The at least 50 contiguous amino acid residues may include an amino acid sequence at least 50% identical, or 100% identical to a sequence selected from the group consisting of SEQ ID NOs:26, 27, 28, and 29.

In these fusion proteins, the immunogenic peptide of the first fusion protein may be joined to the carboxyl-terminal end of a HBcAg coreN domain. The coreN domain may include an amino acid sequence at least 50% identical, or 100% identical to a region corresponding to amino acid 1 to any one of amino acids 71-78 of an HBcAG. The coreN domain may include an amino acid sequence at least 50% identical, or 100% identical to a sequence selected from the group consisting of SEQ ID NOs:30, 31, 32, and 33.

In these fusion proteins, the immunogenic peptide of the second fusion protein may be joined to the amino-terminal end of a HBcAg core C domain. The coreC domain may include an amino acid sequence at least 50% identical, or 100% identical to a region corresponding to any one of amino acids 71-78 to an amino acid residue between amino acid 143 and amino acid 183 of SEQ ID NO:3. The coreC domain may include an amino acid sequence at least 50% identical, or 100% identical to a sequence selected from the group consisting of SEQ ID NOs:34, 35, 36, and 37.

In these fusion proteins, one end of the immunogenic peptide may be joined to the carboxyl-terminal end of the HBcAg α3 helix, and the other end of the helix A immunogenic peptide is joined to the amino-terminal end of the HBcAg α4 helix, and the fusion protein forms a VLP. Thus, the amino-terminal end of the helix A immunogenic peptide may be joined to the carboxyl-terminal end of the HBcAG α3 helix, and the carboxyl-terminal end of the helix A immunogenic peptide may be joined to the amino-terminal end of the HBcAg α4 helix.

Thus, the fusion proteins may include: a) an immunogenic peptide from helix A in the stem region of an influenza hemagglutinin protein; b) a first amino acid sequence comprising at least 30, at least 40, at least 50, or at least 60 contiguous amino acid residues from the polypeptide sequence immediately upstream of the HBcAg c/e1 loop sequence, wherein the first amino acid sequence comprises an HBcAg α3 helix sequence; and, c) a second amino acid sequence comprising at least 50, at least 60, or at least 70 contiguous amino acid residues from the polypeptide sequence immediately downstream of the HBcAg c/e1 loop sequence, wherein the second amino acid sequence comprises an HBcAg α4 helix sequence; such that one end of the immunogenic peptide is joined to the carboxy-terminal end of the first amino acid sequence, and the other end of the immunogenic peptide is joined to the amino-terminal end of the second amino acid sequence. This fusion protein is capable of self-assembling into a VLP. The at least 30, at least 40, at least 50, or at least 60 contiguous amino acid residues are from the polypeptide sequence immediately upstream of any one of amino acid residues 71-82 in SEQ ID NO:3. The at least 30, at least 40, at least 50, or at least 60 contiguous amino acid residues may include an amino acid sequence at least 50% identical, or 100% identical to a sequence selected from the group consisting of SEQ ID NOs:22, 23, 24 and 25. The at least 50, at least 60, or at least 70 contiguous amino acid residues may be from the polypeptide sequence immediately downstream of any one of amino acid residues 71-82 in SEQ ID NO:3. The at least 50, at least 60, or at least 70 contiguous amino acid residues may include an amino acid sequence at least 50%, or 100% identical to a sequence selected from the group consisting of SEQ ID NOs:26, 27, 28, and 29.

Similarly, the fusion protein may include: a) an immunogenic peptide from helix A in the stem region of an influenza hemagglutinin (HA) protein; b) an HBcAg coreN domain; and, c) an HBcAg coreC domain; such that one end of the immunogenic peptide is joined to the carboxy-terminal end of the coreN domain; the other end of the immunogenic peptide is joined to the amino-terminal end of the coreC domain. This fusion protein self-assembles into a VLP. The coreN domain may include an amino acid sequence at least 50% identical, or 100% identical to a region corresponding to amino acid 1 to any one of amino acids 71-78 of an HBcAG. The coreN domain may include an amino acid sequence at least 50% identical, or 100% identical to a region corresponding to amino acid 1 to any one of amino acids 71-78 of SEQ ID NO:3. The coreN domain may include an amino acid sequence at least 50% identical, or 100% identical to a sequence selected from the group consisting of SEQ ID NOs:30, 31, 32, 33. The coreC domain may include an amino acid sequence at least 50% identical, or 100% identical to a region corresponding to any one of amino acids 71-78 to an amino acid residue between amino acid 143 and amino acid 183 of SEQ ID NO:3 of an HBcAg. The coreC domain may include an amino acid sequence at least 50% identical, or 100% identical to a sequence selected from the group consisting of SEQ ID NO:34, 35, 36, and 37.

These fusion proteins may include the amino acid sequence of an HBcAg, such that the helix A immunogenic peptide is inserted into the c/e1 loop. The immunogenic peptide may be inserted between the α3 helix and the c/e1 loop, or between the c/e1 loop and the α4 helix, or between any two amino acids in the region corresponding to amino acids amino acid residues 71-82 in SEQ ID NO:3. In these fusion proteins, the immunogenic protein may replace the c/e1 loop These fusion proteins may comprise an amino acid sequence at least 50%, at least 90%, at least 95%, or at least 99% identical, or 100% identical to the amino acid sequence of a fusion protein listed in Table 1. These fusion proteins may consist of an amino acid sequence at least 50%, at least 90%, at least 95%, or at least 99% identical, or 100% identical to the amino acid sequence of a fusion protein listed in Table 1. These fusion proteins may comprise an amino acid sequence at least 50%, at least 90%, at least 95%, or at least 99% identical, or 100% identical to an amino acid sequence selected from the group consisting of SEQ ID NO:38-SEQ ID NO:69. These fusion proteins may consist of an amino acid sequence at least 50%, at least 90%, at least 95%, or at least 99% identical, or 100% identical to an amino acid sequence selected from the group consisting of SEQ ID NO:38-SEQ ID NO:69.

Another aspect of this disclosure is a nucleic acid molecule encoding any one of these fusion proteins. Another aspect of this disclosure is a virus like particle (VLP) comprising any one of these fusion proteins. Another aspect of this disclosure is a vaccine comprising these VLPs.

Another aspect of this disclosure provides methods of eliciting an immune response against influenza virus in an individual by administering to the individual a VLP or vaccine of this disclosure. Similarly, this disclosure provides methods of vaccinating an individual against influenza virus, by administering to the individual a vaccine of this disclosure. Similarly, this disclosure provides methods protecting an individual against infection by influenza virus by administering to the individual a vaccine of this disclosure.

Another aspect of the disclosure is an antibody that specifically binds to influenza hemagglutinin protein. These antibodies are induced following vaccination of a mammal with a vaccine of this disclosure. These antibodies may be polyclonal antibodies, monoclonal antibodies, bi-specific antibodies, and/or chimeric antibodies.

BRIEF DESCRIPTION OF THE FIGURES

FIGS. 1A-1E depict the design for epitope grafting of the conserved helix A of hemagglutinin (HA) onto a capsid nanoparticle. FIG. 1A shows the structure of influenza HA in complex with scFv from a broadly neutralizing antibody F10 that targets the stem region (PDBID 3FKU). The HA1 head region at the top is shown in medium gray with HA2 stem region in darker gray. The arrow points to helix A within the stem region. The antibody scFv (Ab) is colored in light grey. FIG. 1B shows a hepatitis B virus capsid dimer indicating the alpha helical fold of the protein. The immunodominant loop at the tip of the dimeric spike is denoted by an arrow. The loop area is also referred to as the c1 epitope. FIG. 1C shows the structure of the hepatitis B virus capsid (PDBID 1QGT) with T=4 icosahedral symmetry with 240 subunits of the capsid dimer. The capsid is shown at a reduced scaled. Scale bar, 10 nm. FIG. 1D is a schematic of the capsid protein monomer. FIG. 1E is a schematic of the protein design consisting of a capsid monomer with two copies of helix A (light grey) inserted into the tip of the loop of the capsid protein (dark grey). Alpha helices are schematically shown as rectangles with the base as an oval. Loops are between capsid and influenza sequences.

FIGS. 2A-2D are schematic diagrams of expression constructs of this disclosure. FIG. 2A shows a capsid scaffold without epitope insertions. The capsid sequence is represented by boxes with vertical lines. The immunodominant loop (c1 epitope) is represented as a white box denoted by an asterisk. FIG. 2B shows the nanoparticle stem 01 construct (NP st01) consisting of copies of helix A of influenza hemagglutinin inserted into the capsid at the immunodominant loop region. Each copy of helix is represented by a box with diagonal lines. FIG. 2C shows the nanoparticle stem 02 construct (NP st02) consisting of copies of helix A of influenza hemagglutinin inserted into the capsid at the immunodominant loop region. Each copy of helix is represented by a box with diagonal lines. The NP st02 contains additional flanking linking sequencing (black boxes). An epitope tag is shown as a grey box with horizontal lines. The epitope tag is the epitope for antibody 10E11 that recognizes residues 1-10 at the N-terminus of the capsid. FIG. 2D is the diagram key to indicate the schematic representations for each region: capsid, detection epitope tag, epitope insertion site (immunodominant loop), helix-A, and flanking linkers.

FIG. 3A shows an immunoblot of capsid expression (as positive-control) with at band at about 20 kilodaltons (kDa). FIG. 3B shows an immunoblot of nanoparticle stem 01 construct (NP st01) with at band at about 25 kilodaltons (kDa). FIG. 3C shows an immunoblot of nanoparticle stem 02 construct (NP st02) with at band at about 25 kilodaltons (kDa) Molecular weight standards (std) are denoted.

FIG. 4A shows an SDS-PAGE gel analysis of purified capsid protein detected in different purification fractions. The first lane contains molecular weight stands (std) and other lanes gradient fractions. The capsid bands are at about 20 kilodaltons (kDa). FIG. 4B is an image from electron microscopy of capsid samples. Capsid particles are observed.

FIG. 5A shows an SDS-gel analysis of purified NP st01 protein detected in different purification fractions. The first lane contains molecular weight stands (std) and other lanes gradient fractions. NP st01 bands are at about 25 kilodaltons (kDa) within fractions. FIG. 5B shows an electron microscopy of NP st01 samples. Nanoparticles are observed.

FIGS. 6A and 6B depict the purification and particle formation of nanoparticle stem 02 construct (NP st02). FIG. 6A is an SDS-PAGE gel analysis of purified NP st02 protein detected in different purification fractions. The first lane contains molecular weight stands (std) and other lanes gradient fractions. NP st02 bands are at about 25 kilodaltons (kDa) within fractions. FIG. 6B shows an electron microscopy of NP st02 samples. Nanoparticles are observed.

FIG. 7 shows the comparative reactivity of nanoparticles with antibodies. Dob-blot analysis of cross-reactivity of nanoparticles with polyclonal rabbit antibodies to influenza H1 hemagglutinin protein. Antigens were capsid, NPst01, and NPst02 at decreasing concentrations (1.0 to 0.003 micrograms (µg)). Bovine serum albumin (BSA) was negative control. Primary antibody was a rabbit polyclonal (H1 pAb) that was raised against full-length H1 hemagglutinin. The secondary antibody used for detection was anti-mouse antibody conjugated to alkaline-phosphate and chromogenic development was used to visualize dots. Two different purified preparations were tested for each particle sample. NP st01 showed low level of reactivity while NP st-02 showed relatively stronger reactivity to H1 polyclonal antibodies.

FIG. 8 shows the results of probing for insertion of foreign epitope into capsid loop by anti-loop monoclonal antibody 88 (mAb88). Dob-blot analysis to compare the reactivity of capsid versus the nanoparticle stem 02 construct (NP st02) when probed with a capsid-specific mAb 88 to the immunodominant loop (c1 epitope) of the capsid. Antigens were capsid and NPst02 preparations at decreasing concentrations. Hemagglutinin (HA) H1 was used as a negative control.

FIG. 9 shows the schedule for immunization of mice with nanoparticle stem 02 (NP st02) and challenge with 2009 pandemic H1N1 influenza virus. BALB/c mice were used. There were three groups consisting of PBS, NP st-02 plus adjuvant (Ribi) and NP st-02 without adjuvant. The route of injection was intramuscular and the route of challenge was intranasal with pandemic influenza virus (A/California/07/09) H1N1.

FIGS. 10A and 10B show the immunogenicity of nanoparticle stem 02 (NP st02) assessed by ELISA. FIG. 10A shows antibody levels of sera of immunized mice analyzed by ELISA for reactivity to nanoparticle (NP st02) and cross-reactivity with influenza H1 hemagglutinin (HA) protein at Day 14 with one intramuscular (IM) injection. FIG. 10B shows similar analysis of mice sera at Day 35 after two intramuscular (2IM) injections. There were three groups of sera tested consisting of PBS (saline, black bar), NP st-02 without adjuvant (white bar) and NP st-02 plus adjuvant (Ribi) (grey bar). NP st02 is labeled as Nanoparticle and hemagglutinin as H1.

FIGS. 11A and 11B show the protection of mice from challenge with influenza virus following immunization with nanoparticle. FIG. 11A shows a comparison of survival curves of mice challenged with 10 MLD50 (mouse lethal dose) of H1N1 virus at day 42 after two intramuscular inoculations at days 0 and 21 with nanoparticle NP-st02 without addition of Ribi adjuvant (panel A, dotted line) compared with a PBS control (panel A, solid line). FIG. 11B shows a comparison of survival curves of mice challenged with 10 MLD50 (mouse lethal dose) of H1N1 virus at day 42 after two intramuscular inoculations at days 0 and 21 with nanoparticle NP-st02 with the addition of Ribi adjuvant (panel B, dotted line) compared with a PBS control (panel B, solid line). Virus was pandemic influenza virus (A/California/07/09) H1N1.

FIGS. 12A and 12B show the reduction in observed morbidity of mice from challenge with influenza virus following immunization with nanoparticle. FIG. 12A shows a comparison of weight-loss curves of challenged mice immunized with nanoparticle NP-st02 without Ribi adjuvant (panel A, dotted line with squares) compared to PBS control (panel A, solid black line). FIG. 12B shows a comparison of weight-loss curves of challenged mice immunized with nanoparticle NP-st02 with Ribi adjuvant (panel B, dotted line with circles) compared to PBS control (panel B, solid black line). Virus was pandemic influenza virus (A/California/07/09) H1N1. Nanoparticle without Ribi adjuvant appeared more efficacious in reducing weight-loss associated with infection.

FIGS. 13A-13D show an analysis of the effects of temperature on integrity and immunogenicity of nanoparticle NPst02. FIGS. 13A, 13B, and 13C are negative-stained electron microscopy images of nanoparticles incubated at 4, 40, and 90 degrees Celsius, respectively, for 30 minutes then returned to room temperature (Scale bar 100 nm). FIG. 13D shows antibody levels of sera from immunized mice analyzed by ELISA for reactivity to capsid, nanoparticle (Nano), and influenza H1 hemagglutinin (HA) protein at day 35 after two intramuscular injections. Four groups of sera were tested consisting of PBS (saline) and nanoparticle NP st-02 exposed to three temperatures, 4, 40, and 90 degrees Celsius (Nano 4, 40, 90).

FIG. 14 shows identity comparisons of sequences for helix A for each HA subtype collected from hemagglutinin sequences (n=50,426) (H1 to H16) from an influenza sequence database.

FIGS. 15A-15D shows the results of an immunogenicity study in which nanoparticle stem 02 (NP-st02) is used for prime and/or prime/boost. Mice were primed with either saline, scaffold alone (Scaf), HA protein from A/California/07/09 H1 or NP-st02, and then boosted at 21 days with either saline, scaffold alone (Scaf), A/California/07/09 H1 HA protein, or NP-st02. The charts show sera levels of anti-A/California/07/09 H1 HA protein antibody at various times post-immunization, as determined by ELISA. FIG. 15A shows the level of anti-HA antibody in mice primed with saline and boosted with saline (black circles), primed with saline and boosted with scaffold (Scaff) (black diamonds), primed with Scaf and boosted with saline (grey circles), or primed with Scaf and boosted with Scaf (grey diamonds); FIG. 15B shows the level of anti-HA antibody in mice primed with saline and boosted with saline (black circles, dotted line), primed with saline and boosted with influenza H1 HA protein (black triangles, dotted line), prime with H1 HA protein and boosted with saline (grey circle, solid line), or primed with H1 HA protein and boosted with H1 HA protein; (grey triangles, solid line). FIG. 5C shows the level of anti-HA antibody in mice primed with saline and boosted with saline (black circles, dotted line), primed with saline and boosted with H1-nanoparticle (NPst02) (black squares, dotted line), primed with NPst02 and boosted with saline (black circle, solid line), or primed with NPst02 and boosted with NPst02 (black square, solid line); FIG. 5D shows the level of anti-HA antibody in mice primed with NP-st02 and boosted with NPst02 (black squares), primed with NPst02 and boosted with H1 HA protein (black triangles), primed with H1 HA protein (grey squares), or primed with H1 HA protein and boosted with H1 HA protein (grey triangles). Nanoparticles (NP-502) appeared to be more immunogenic and elicit higher level of anti-HA antibodies than HA protein.

FIGS. 16A-16E show a structural analysis of H1-nanoparticle (NPst02) by cryo-electron microscopy and molecular modeling. FIG. 16A is a Cryo-EM image of a field of H1-nanoparticle. White arrows denote some particles. Scale bar 100 nm. Protein contrast is black. FIG. 16B shows reference-free 2D classes of the nanoparticle. Protein contrast is white. Scale bar 20 nm. FIG. 16C shows a central-slice through the 3D reconstruction of the nanoparticle. Black arrows denote some of surface spikes where the inserted epitope is located. Protein contrast is black. Scale bar 20 nm. FIG. 16D shows a molecular model of the nanoparticle. The influenza HA epitopes are displayed on the surface and fused to the scaffold region. FIG. 16E is a schematic illustrating a building block of the nanoparticle which is a dimeric unit. For FIGS. 16D and 16E, arrows denote some HA epitopes. Epitopes and scaffold regions are delineated by brackets.

FIGS. 17A-17D shows the strategy for bioinformatic design of a nanoparticle library for the display of stem regions of different hemagglutinin (HA) subtypes and expression screening of the designed fusion proteins. FIG. 17A shows a library design by downloading and curating over 50,0000 sequences of HA from the influenza database into about 36,000 stem epitopes for HA subtypes (H1-H18) and influenza B HA. A cDNA sequence library was created containing 30 HA-nanoparticle fusion proteins containing H1-H18 stem epitopes and HB stem epitopes. FIG. 17B shows a bioinformatic analysis of 27 sequences (H1-H16) HA-nanoparticle library in order to compare sequence identity and coverage against the larger epitope database of over 36,000 HA sequences. FIG. 17C is a pie chart showing the coverage of the 27 H1-H16 nanoparticle library.

FIGS. 18A-18E show expression, purification, and immunogenicity of H5-nanoparticle.

FIG. 18A is a SDS-PAGE gel analysis of purified H5-nanoparticle protein (H5-NP) constructed of a H5 HA stem region fused to a scaffold. The first lane contains molecular weight stands (std) and other lane purified H5-nanoparticle (H5-NP). An arrow indicates a monomer band at about 25 kilodaltons (kDa) for H5-NP. FIG. 18B shows electron microscopy of H5-NP sample. Scale bar 200 nm. FIG. 18C is an ELISA of sera from mice injected with H5-NP. Sera was probed for binding to H5-NP. The dotted line represents PBS baseline subtracted and set to zero. FIG. 18D is an ELISA to compare the reactivity of H5-NP sera to H5-NP, recombinant H5 hemagglutinin (HA) proteins and scaffold without epitope. FIG. 18E shows an immunoblot to probe the binding of H5 NP sera to recombinant H5 hemagglutinin (HA) proteins. Standards are std. Recombinant H5 HA proteins were from H5N1 influenza viruses A/Indonesia/05/2005 (H5N1) (H5 HA Indo) and A/Vietnam/1203/2004 (H5N1) (H5 HA Viet). Nanoparticle carrying the H5 HA stem regions (H5-NP) could be purified and was immunogenic and elicited antibodies that bound H5-nanoparticle and recombinant H5 HA protein.

FIGS. 19A-19E show expression, purification, and immunogenicity of H7-nanoparticle. FIG. 19A is an SDS-PAGE gel analysis of purified H7-nanoparticle protein (H7-NP) constructed of a H7 HA stem region fused to a scaffold. The first lane contains molecular weight stands (std) and other lane purified H7-nanoparticle (H7-NP). An arrow indicates a monomer band at about 25 kilodaltons (kDa) for H7-NP. FIG. 19B is an electron microscopy of H7-NP sample. Scale bar 200 nm. FIG. 19C is an ELISA of sera from mice injected with H7-NP. Sera was probed for binding to H7-NP. The dotted line represents PBS baseline subtracted and set to zero. FIG. 19D is an ELISA to compare the reactivity of H7-NP sera to H7-NP, recombinant H7 hemagglutinin (HA) proteins and scaffold without epitope. FIG. 19E is an immunoblot to probe the binding of H7-NP sera to recombinant H7 hemagglutinin (HA) proteins. Standards are std. Recombinant H7 HA proteins were from influenza viruses A/Anhui/01/2013 (H7N9) (H7 HA Anhui) and A/Netherlands/219/2003 (H7N7) (H7 HA Neth). Nanoparticle carrying the H7 HA stem regions (H7-NP) could be purified and was immunogenic and elicited antibodies that bound H7-nanoparticle and recombinant H7 HA proteins.

FIGS. 20A-20E show the results of using recombinant HA proteins and nanoparticle sera to probe for homosubtypic and heterosubtypic binding of antibodies. FIG. 20A is an immunoblot displaying reactivity of H7 nanoparticle mice sera to recombinant H1 HA proteins. FIG. 20B is an immunoblot displaying reactivity of H1 nanoparticle sera to recombinant H7 HA proteins. Standards are denoted (std). FIG. 20C is an ELISA displaying reactivity of H7 nanoparticle sera to recombinant H1 HA proteins. H1 HA binding by H7 sera is statically significant when compared to PBS control. FIG. 20D is an immunoblot displaying reactivity of H5 nanoparticle sera to recombinant H1 HA proteins. FIG. 20E is an ELISA displaying reactivity of H5 nanoparticle sera to recombinant H1 HA proteins. Based on ELISA H1 HA binding by H5 sera is statically not significant when compared to PBS control, but binding can be detected by immunoblots (FIG. 20D). Recombinant HA proteins were from influenza viruses: H1 A/California/04/2009 (H1N1), H1 A/California/07/2009 (H1N1), H1 A/Brisbane/59/2007 (H1N1), H1 A/Solomon Islands/03/2006 (H1N1), H1 A/New Caledonia/20/1999 (H1N1), H1 A/Puerto Rico/8/1934 H1N1, H7 A/Anhui/01/2013 (H7N9), H7 A/Netherlands/219/2003 (H7N7). The designed nanoparticles with HA stem epitopes appear to have the ability to elicit both homosubtypic and heterosubtypic binding antibodies to influenza hemagglutinins.

FIG. 21A shows an analysis by ELISA of the binding of different nanoparticle mice sera to recombinant H1 HA protein (A/California/07/2009 (H1N1)). FIG. 21B shows an analysis by ELISA of the binding of different nanoparticle sera to recombinant H7 HA protein (A/Anhui/01/2013 (H7N9)). FIG. 21C shows an analysis by ELISA of the binding of different nanoparticle sera to recombinant H5 HA protein (A/Vietnam/1203/2004 (H5N1)). FIG. 21D is a schematic key for sera used. Nanoparticles carried HA stem epitopes from H1 pandemic (H1 P), H1 seasonal (H1 S), H5 and H7 hemagglutinins (HA). Scaffolding does not contain a stem epitope. Saline is given to mice as a control and PBS is used in ELISA as a control. The designed nanoparticles with HA stem epitopes appear to have the ability to elicit both homosubtypic and heterosubtypic binding antibodies to influenza hemagglutinins.

DETAILED DESCRIPTION

Figure 3A:
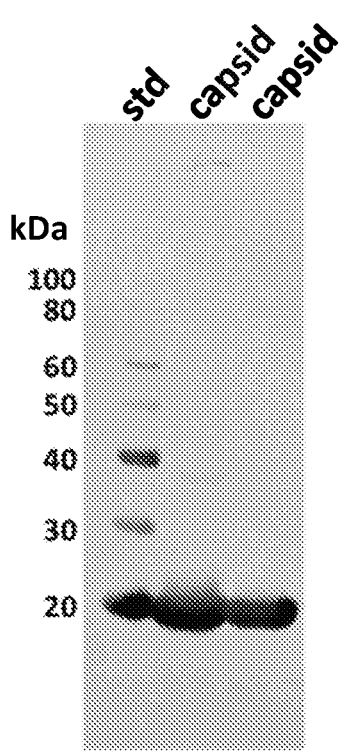
FIGS. 3A-3C show the detection of protein expression from expression constructs by immunoblotting (western blotting). Samples were denatured by SDS-PAGE under reducing conditions and then transferred to nitrocellulose membrane. Primary antibody was mAb 10E11 that recognizes residues 1-10 at the N-terminus of the capsid region. The secondary antibody used for detection was anti-mouse antibody conjugated to alkaline-phosphate and chromogenic development was used to visualize bands. For each construct two independent preparations of crude lysates of bacteria from expression cultures were tested.

This disclosure provides a fusion-protein based nanoparticle vaccine for influenza virus. Nanoparticle vaccines of this disclosure comprise virus-like particles (VLPs) that are made from hepatitis B virus (HBV) core antigen (cAg) (HBcAg) monomeric subunits, which display influenza virus antigens on their surface. More specifically, VLPs of this disclosure are made from fusion proteins comprising at least a portion of a HBcAg joined to an influenza HA epitope in such a manner that the fusion protein is capable of forming a VLP displaying the HA epitope on its surface. Such VLPs are capable of inducing broadly neutralizing antibodies against one or more serotypes of influenza virus. Thus, methods of this disclosure can generally be practiced by administering a VLP of this disclosure to an individual.

The invention is not limited to the specific embodiments described herein, as such may vary. It is also to be understood that the terminology used herein is used to describe embodiments only, and is not intended to be limiting.

Although methods and materials similar or equivalent to those described herein can be used in the practice or testing of the present invention, suitable methods and materials are described below. The publications and applications discussed herein are provided solely for their disclosure prior to the filing date of the present application. Nothing herein is to be construed as an admission that the present invention is not entitled to antedate such publication. In addition, the materials, methods, and examples are illustrative only and are not intended to be limiting.

Unless defined otherwise, all technical and scientific terms used herein have the meaning commonly understood by one of skill in art to which the subject matter belongs. The following definitions are supplied to facilitate the understanding of the present invention.

As used herein, the singular forms "a," "an," and "the" include plural referents unless the context clearly dictates otherwise. For example, a nucleic acid molecule refers to one or more nucleic acid molecules. The terms "comprising," "including," and "having" can also be used interchangeably. Furthermore, the phrase "selected from the group consisting of" refers to one or more members of the group in the list that follows, including mixtures (i.e. combinations) of two or more members. As used herein, "at least one" means one or more. The term "comprise" is generally used in the sense of "including", i.e., permitting the presence of one or more features or components. Where descriptions of various embodiments use the term comprising, that embodiment may also be described using the transitional phrase "consisting essentially of."

The claims may be drafted to exclude any optional element, and this statement serves as antecedent basis for use of such exclusive terminology as "solely," "only" and the like in connection with the recitation of claim elements or use of a "negative" limitation. Further, while various embodiments and technical aspects of this disclosure may appear in separate locations in the specification, it should be clear that combinations of such embodiments and technical aspects are also encompassed by this disclosure.

As briefly discussed above, nanoparticle vaccines of this disclosure comprise virus-like particles (VLPs) that are assembled from HBV core antigen (HBcAg) monomeric subunits, preferably HBcAg monomeric subunits made from fusion proteins of the present invention. For ease of discussion, in the present application the terms nanoparticle and VLP may be used interchangeably.

Hepatitis B virus core particles are nanoparticles of icoshedral symmetry (diameter: approx. 30 nm) which consist of 180 or 240 copies of the viral core protein. The core particle is made of monomeric subunits of HBV core antigen (HBcAg). The HBcAg has a unique structure comprised of two anti-parallel α-helices which form a characteristic "spike" structure. Two HBc molecules then spontaneously dimerize to form a twin spike bundle, which is the building block of the core particle.

The three-dimensional structure of the HBcAg protein has shown to contain numerous α-helical structures, two of which (α3 and α4) pair to form a paired-helix, spike-like structure. Between the distal tips of the two helices (thus at the end of the spike) is a sequence that forms a loop structure, which is referred to as the "c/e1" loop. The spike-like monomeric subunits dimerize to form a four-helix HBcAG dimer, which then assemble to from the viral core (or VLP). The α3/α4 spike-like structure projects out from the viral core, with the result that the c/e1 loop is displayed on the outside of the core particle.

HBV core antigen monomers can self-assemble to form virus-like particles. (Conway et al., Nature, 386:91-94 (1997); Bottcher et al., Nature, 386:88-91 (1997)). Moreover, it has also been shown that if the N-terminal half and the C-terminal half of the HBcAg are expressed separately, the middle of the HBcAG sequence being roughly defined by the c/e1 loop sequence, the two halves can associate though pairing of their helices, to form the spike-like, monomeric subunit, which can then dimerize and self-assemble into a VLP. Such proteins can therefore be used to produce HBV VLP-based vaccines.

This disclosure provides fusion proteins selected from:
a) a first fusion protein comprising an immunogenic peptide from helix A in the stem region of an influenza hemagglutinin (HA) protein, joined to the carboxyl-terminal end of the α3 helix from a hepatitis B core antigen (HBcAg); and,
b) a second fusion protein comprising an immunogenic peptide from helix A from the stem region of an influenza hemagglutinin (HA) protein, joined to the amino-terminal end of the α4 helix from a hepatitis B core antigen (HBcAg).

In these fusion proteins, the first fusion protein may form a virus-like particle (VLP) when combined with a HAcAg-C protein. The second fusion protein may form a virus-like particle (VLP) when combined with a HAcAG-N protein.

As used herein, a "fusion protein" is a recombinant protein containing amino acid sequences from at least two unrelated proteins that have been joined together to make a single protein. Two unrelated proteins may be joined by a covalent bond, for example, a peptide bond. It should be appreciated that fusion proteins are made by the hand of man.

As used herein, proteins are unrelated if their amino acid sequences are not normally found joined together via a peptide bond in their natural environment(s) (e.g., inside a cell). Sequences from the influenza virus hemagglutinin protein are not normally found joined to sequences from hepatitis B virus. However, such a construct can be recombinantly produced and would be referred to herein as a fusion protein.

The immunogenic peptide and the HBcAg sequences of this disclosure may be joined to each other directly. Alternatively or additionally, it may be necessary to employ linker sequences (also referred to as spacer sequences) so that the various domains are in the proper spatial orientation. A linker sequence may be designed to position the immunogenic peptide in such a way to maintain the ability of the protein to elicit an immune response to influenza virus. Linker sequences of the present invention comprise amino acids, preferably amino acids having small side chains and/or those which are not charged. Such amino acids are less likely to interfere with proper folding and activity of the fusion protein. Accordingly, preferred amino acids to use in linker sequences, either alone or in combination, are serine, glycine, and alanine. Examples of such linker sequences include, but are not limited to, a polyG sequence comprising between one and three glycine residues, a glycine-serine sequence (e.g., GGGS), and multiples thereof. Amino acids can be added or subtracted as needed. Those skilled in the art are capable of determining appropriate linker sequences for proteins of this disclosure.

As used herein, the term "immunogenic" refers to the ability of a specific protein, or a specific region thereof, to elicit an immune response to the specific protein, or to proteins comprising an amino acid sequence having a high degree of identity with the specific protein. According to the present invention, two proteins having a high degree of identity have amino acid sequences at least 50% identical, at least 87% identical, at least 90% identical, at least 92% identical, at least 94% identical, at least 96% identical, at least 98% identical or at least 99% identical.

As used herein, an "immune response" to a vaccine or nanoparticle is the development in a subject to which the vaccine or nanoparticle has been administered, of a humoral and/or a cellular immune response to a hemagglutinin protein present in the vaccine. For purposes of the present invention, a "humoral immune response" refers to an immune response mediated by antibody molecules, including secretory IgA or IgG molecules, while a "cellular immune response" is one mediated by T-lymphocytes and/or other white blood cells. One important aspect of cellular immunity involves an antigen-specific response by cytolytic T-cells (CTLs). CTLs have specificity for peptide antigens that are presented in association with proteins encoded by the major histocompatibility complex (MHC) and expressed on the surface of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A cellular immune response also refers to the production of cytokines, chemokines, and other such molecules produced by activated T-cells and/or other white blood cells, including those derived from CD4+ and CD8+ T-cells.

Thus, an immune response may be one that stimulates CTLs, and/or the production or activation of helper T-cells. The production of chemokines and/or cytokines may also be stimulated. The vaccine may also elicit an antibody-mediated immune response. Hence, an immune response may include one or more of the following effects: the production of antibodies (e.g., IgA or IgG) by B-cells; and/or the activation of suppressor, cytotoxic, or helper T-cells and/or T-cells directed specifically to a hemagglutinin protein present in the vaccine. These responses may serve to neutralize infectivity, and/or mediate antibody-complement, or antibody dependent cell cytotoxicity (ADCC) to provide protection to an immunized individual. Such responses can be determined using immunoassays and neutralization assays known in the art.

All nomenclature used in this disclosure to classify influenza virus is that commonly used by those skilled in the art. Thus, a Type, or Group, of influenza virus refers to influenza Type A, influenza Type B or influenza type C. The designation of a virus as a specific Type relates to sequence differences in the respective M1 (matrix) protein or NP (nucleoprotein). Type A influenza viruses are further divided into Group 1 and Group 2. These Groups are further divided into subtypes, which refers to classification of a virus based on the sequence of the viruses HA protein. Examples of commonly recognized subtypes are H1, H2, H3, H4, H5, H6, H7, H8, H8, H10, H11, H12, H13, H14, H15, H16, H17, and H18. Group 1 influenza subtypes are H1, H2, H5, H7 and H9. Group 2 influenza subtypes are H4, H4, H6, H8, H10, H11, H12, H13, H14, H15 H16, H17, and H18. Finally, the term strain refers to viruses within a subtype that differ from one another in that they have small, genetic variations in their genome.

As used herein, neutralizing antibodies are antibodies that prevent a pathogen, such as influenza virus from completing one round of replication. One round of replication refers to the life cycle of the virus, starting with attachment of the virus to a host cell and ending with budding and release of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles, and budding and release of viral particles from the host cell membrane.

As used herein, broadly neutralizing antibodies are antibodies that neutralize more than one type, subtype, and/or strain of a pathogen, such as influenza virus. For example, broadly neutralizing antibodies elicited against an HA protein from a Type A influenza virus may neutralize a Type B and/or a Type C virus. As a further example, broadly neutralizing antibodies elicited against an HA protein from Group I influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15, H16, H17, and H18.

As used herein, an influenza hemagglutinin protein, or HA protein, refers to a full-length influenza hemagglutinin protein, modified versions thereof, variants thereof, or any portion thereof, that elicits an immune response. Examples of influenza HA proteins useful for practicing the methods disclosed herein are known in the art, and are also disclosed in U.S. Pat. No. 9,441,019, which is incorporated herein by reference in its entirety. An immunogenic peptide from an influenza hemagglutinin protein means an amino acid sequence from an influenza HA protein comprises at least one epitope. An epitope of an influenza hemagglutinin protein refers to an at least six contiguous amino acid sequence from an influenza HA protein that can elicit a neutralizing antibody response against a homologous influenza strain, i.e., a strain from which the HA is derived. Such an epitope may also elicit a neutralizing antibody response against a heterologous influenza strain, i.e., a strain having an HA that is not identical to that of the HA of the immunogen.

As used herein, a variant refers to a protein or nucleic acid molecule, the sequence of which is similar, but not identical to a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6.

With regard to variants, any type of alteration in the amino acid or nucleic acid sequence is permissible as long as the activity of the resulting variant protein or polynucleotide is not significantly altered. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

Variant proteins of the present invention may contain amino acid substitutions relative the proteins disclosed herein. Amino acids can be classified into groups based on their physical properties. Examples of such groups include charged amino acids, uncharged amino acids, polar uncharged amino acids, and hydrophobic amino acids. Thus, protein variants containing substitutions may be those in which an amino acid is substituted with an amino acid from the same group. Such substitutions are referred to as "conservative" substitutions.

Naturally occurring residues may be divided into classes based on common side chain properties, as follows:
1) hydrophobic: Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

Non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those within ±1 are particularly preferred, and those within ±0.5 are even more preferred.

The substitution of like amino acids can be made effectively on the basis of hydrophilicity, particularly where the biologically functionally equivalent protein or peptide thereby created is intended for use in immunological invention, as in the present disclosure. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those within ±1 are particularly preferred, and those within ±0.5 are even more particularly preferred. One may also identify epitopes from primary amino acid sequences on the basis of hydrophilicity.

Desired amino acid substitutions (whether conservative or non-conservative) can be determined by those skilled in the art at the time of making such substitutions. For example, amino acid substitutions can be used to identify important residues of the protein, or to increase or decrease the immunogenicity, solubility, or stability of the proteins described herein. Exemplary amino acid substitutions are shown in the following table:

| Amino Acid Substitutions | |
|---|---|
| Original Amino Acid | Exemplary Substitutions |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase "significantly affects a protein's activity" refers to a decrease in the activity of a protein by at least 10%, at least 20%, at least 30%, at least 40% or at least 50%. With regard to the present fusion proteins, such an activity may be measured as the ability of a protein to elicit neutralizing antibodies against an influenza virus. Such activity may be measured by measuring the titer of such antibodies against influenza virus, or by measuring the number of types, subtypes or strains neutralized by the elicited antibodies. Methods of determining antibody titers and methods of performing virus neutralization assays are known to those skilled in the art. In addition to the activities described above, other activities that may be measured include the ability to agglutinate red blood cells and the binding affinity of the protein for a cell, and methods of measuring such protein activities are known to those skilled in the art.

Hemagglutinin proteins from different influenza viruses may have different lengths due to mutations (insertions, deletions) in the protein. Thus, reference to a corresponding region refers to a region of another protein that is identical, or nearly so (e.g., at least 95%, identical, at least 98% identical or at least 99% identical), in sequence, structure and/or function to the region being compared. For example, with regard to the stem region of a hemagglutinin protein, the corresponding region in another hemagglutinin protein may not have the same residue numbers but may have a nearly identical sequence and will perform the same function. To better clarify sequences comparisons between viruses, numbering systems are used by those in the field, which relate amino acid positions to a reference sequence. Thus, corresponding amino acid residues in hemagglutinin proteins from different strains of influenza may not have the same residue number with respect to their distance from the n-terminal amino acid of the protein. For example, using the H3 numbering system, reference to residue 100 in A/New Caledonia/20/1999 (1999 NC, H1) does not mean it is the 100<sup>th</sup> residue from the N-terminal amino acid. Instead, residue 100 of A/New Caledonia/20/1999 (1999 NC, H1) aligns with residue 100 of influenza H3N2 strain. The use of such numbering systems is understood by those skilled in the art. Unless otherwise noted, reference to amino acids in hemagglutinin proteins herein is made using the H3 numbering system.

As used herein, helix A from the stem region of an influenza HA protein refers to an amino acid sequence corresponding to the sequence of helix A from the stem region of an influenza H A/California/07/09 HA protein, the sequence of which is represented by SEQ ID NO:1, as shown below in Table 1, which lists examples of sequences useful for practicing the present invention.

TABLE 1

| SEQ ID NO | Sequence | Notes |
|---|---|---|
| 1 | MKAILVVLLYTFATANADTLCIGYHANNSTDTVDTVLEKNVTVTHSVN LLEDKHNGKLCKLRGVAPLHLGKCNIAGWILGNPECESLSTASSWSYI VETPSSDNGTCYPGDFIDYEELREQLSSVSSFERFEIFPKTSSWPNHD SNKGVTAACPHAGAKSFYKNLIWLVKKGNSYPKLSKSYINDKGKEVLV LWGIHHPSTSADQQSLYQNADAYVFVGSSRYSKKFKPEIAIRPKVRXX EGRMNYYWTLVEPGDKITFEATGNLVVPRYAFAMERNAGSGIIISDTP VHDCNTTCQTPKGAINTSLPFQNIHPITIGKCPKYVKSTKLRLATGLR NIPSIQSRGLFGAIAGFIEGGWTGMVDGWYGYHHQNEQGSGYAADLKS TQNAIDEITNKVNSVIEKMNTQFTAVGKEFNHLEKRIENLNKKVDDGF LDIWTYNAELLVLLENERTLDYHDSNVKNLYEKVRSQLKNNAKEIGNG CFEFYHKCDNTCMESVKNGTYDYPKYSEEAKLNREEIDGVKLESTRIY QILAIYSTVASSLVLVVSLGAISFWMCSNGSLQCRICI | HA Sequence of HA from influenza A/California/07/09 |
| 2 | DLKSTQNAIDEITNKVNSVIEK | Helix A sequence from SEQ ID NO: 1 (amino acids 381-402) |
| 3 | MDIDPYKEFGASELLSFLPSDFFPSIRDLLDTASALYREALESPEHCS PHHTALRQAILCWGELMNLATWVGSNLEDPASRELVVSYVNVNMGLKI RQLLWFHISCLTFGRETVLEYLVSEGVWIRTPPAYRPPNAPILSTLPE TTVVRRRGRSPRRRTPSPRRRRSQSPRRRRSQSRESQC | HBV core antigen (HBcAg) α3 and α4 helices are underlined |
| 4 | PHHTALRQAILCWGELMNLATWVGSNLEDP | Extended α3 helix |
| 5 | PHHTALRQAILCWGELMNLATWVGS | HBcAg α3 helix |
| 6 | PHHTALRQAILCWGELMNLATWVG | HBcAg α3 helix |
| 7 | PHHTALRQAILCWGELMNLATWV | HBcAg α3 helix |
| 8 | PHHTALRQAILCWGELMNLATW | HBcAg α3 helix |
| 9 | PASRELVVSYVNVNMGLKIRQLLWFHISCLTF | HBcAg α4 helix |
| 10 | ASRELVVSYVNVNMGLKIRQLLWFHISCLTF | HBcAg α4 helix |
| 11 | SRELVVSYVNVNMGLKIRQLLWFHISCLTF | HBcAg α4 helix |
| 12 | RELVVSYVNVNMGLKIRQLLWFHISCLTF | HBcAg α4 helix |
| 13 | PASRELVVSYVN | HBcAg α4a helix |
| 14 | ASRELVVSYVN | HBcAg α4a helix |
| 15 | SRELVVSYVN | HBcAg α4a helix |
| 16 | RELVVSYN | HBcAg α4a helix |
| 17 | NMGLKIRQLLWFHISCLTF | HBcAg α4b helix |
| 18 | VGSNLEDPAS | c/e1 loop |
| 19 | SNLEDPAS | c/e1 loop |
| 20 | VGSNLED | c/e1 loop |
| 21 | SNLED | c/e1 loop |
| 22 | LESPEHCSPHHTALRQAILCWGELMNLATW | c/e1 upstream sequence |

TABLE 1-continued

| SEQ ID NO | Sequence | Notes |
|---|---|---|
| 23 | DTASALYREALESPEHCSPHHTALRQAILCWGELFINLATW | c/e1 upstream sequence |
| 24 | DFFPSIRDLLDTASALYREALESPEHCSPHHTALLRQAILCWGELMNLATW | c/e1 upstream sequence |
| 25 | SVELLSFLPSDFFPSIRDLLDTASALYREALESPEHCSPHHTALRQAILCWGELMNLATW | c/e1 upstream sequence |
| 26 | RELVVSYVNVNMGLKIRQLLWFHISCLTFGRETVLEYLVSFGVWIRTPPAYRPPNAPILSTLPETTVVRR | c/e1 downstream sequence |
| 27 | RELVVSYVNVNMGLKIRQLLWFHISCLTFGRETVLEYLVSFGVWIRTPPAYRPPNAPILS | c/e1 downstream sequence |
| 28 | RELVVSYVNVKMGLKIRQLLWFHISCLTFGRETVLEVLVSFGVWIRTPPA | c/e1 downstream sequence |
| 29 | RELVVSYVNVNMGLKIRQLLWFHISCLTFGRETVLEYLVS | c/e1 downstream sequence |
| 30 | MDIDPYKEFGASVELLSFLPSDFFPSIRDLLDTASALYREALESPEHCSPHHTALRQAILCWGELMNLATWVGNLED | Core N domain sequence |
| 31 | MDIDPYKEFGASVELLSFLPSDFFPSIRDLLDTASALYREALESPEHCSPHHTALRQAILCWGELMNLATWVG | Core N domain sequence |
| 32 | MDIDPYKEFGASVELLSFLPSDFFPSIRDLLDTASALYREALESPEHCSPHHTALRQAILCWGELMNLATWV | Core N domain sequence |
| 33 | MDIDPYKEFGASVELLSFLPSDFFPSIRDLLDTASALYREALESPEHCSPHHTALRQAILCWGELMNLATW | Core N domain sequence |
| 34 | PASRELVVSYVNVNMGLKIRQLLWFHISCLTFGRETVLEYLVSFGVWIRTPPAYRPPNAPILSTL | CoreC domain sequence |
| 35 | ASRELVVSYVMVKMGLKIRQLLWFHISCLTFGRETYLEYLVSFGVWIRTPPAYRPPNAPILSTL | CoreC domain sequence |
| 36 | SRELVVSYVNVNMGLKIRQLLWFHISCLTFGRETVLEYLVSFGVWIRTFPAYRPPNAPILSTL | CoreC domain sequence |
| 37 | RELVVSYVNVKMGLKIRQLLWFHISCLTFGRETVLEYLVSFGVWIRTPPAYRPPKAPILSTL | CoreC domain sequence |
| 38 | MDIDPYKEFGASVELLSFLPSDFFPSIRDLLDTASALYREALSSPEHCSPHHTALSQAILCWGELMNLATWDLKSTQNAIDEITNKVNSVIEKVGSNLEDPASDLKSTQNAIDEITNKVKSVIEKRELWSYVNVKMGLKIRQLLWFHISCLTFGRETVLEYLVSFGVWIRTPPAYRPPNAPILSTLPETTVVRRRGRSPRRRTPSPRRRRSQSPRRRRSQSRESQC | HBcAg with inserted helix A sequence from influenza H1. |
| 39 | MDIDPYKSFGASVELLSFLPSDFFPSIRDLLDTASALYREALESPEHCSPHHTALRQAILCWGELMNLATWGGGDLKSTQNAIDEITNKVNSVIEKGGGVGSNLEDPASGGGDLKSTQNAIDEITNKVNSVIEKGGGRELWSYVNVNMGLKIRQLLWFHISCLTFGRETVLEYLVSFGVWIRTPPAYRPPNAPILSTLPETTVVRRRGRSPRRRTPSPRRRRSQSPRRRRSQSRESQC | HBcAg with inserted helix A sequence from influenza H1. Helix sequence flanked by linkers. |
| 40 | MDIDPYKEFGASVELLSFLPSDFFPSIRDLLDTASALYREALESPEHCSPHHTALRQAILCWGELMNLATWGGGDLKSTQNAIDEITNKVNSVIEKGGGVGSNLEDPASGGGDLKSTQNAIDEITNKVNSVIEKGGGRELVVSYVNVNMGLKIRQLLWFHISCLTFGRETVLEYLVSFGVWIRTPPAYRPPNAPILSTLPETTVVRRRGRSPRRRTPSPRRRRSQSPRRRRSQSRESQC | HBcAg with inserted helix A sequence from influenza H1. Helix sequence flanked by linkers. |
| 41 | MDIDPYKEFGASVELLSFLPSDFFPSIRDLLDTASALYREALESPEHCSPHHTALRQAILCWGELMNLATWGGGDQKSTQNAINGITNKVNSIIEKGGGVGSNLEDPASGGGDQKSTQNAINGITNKVNSIIEKGGGRELVVSYVNVNMGLKIRQLLWFHISCLTFGRETVLEYLVSFGVWIRTPPAYRPPNAPILSTLPETTVVRRRGRSPRRRTPSPRRRRSQSPRRRRSQSRESQC | HBcAg with inserted helix A sequence from influenza H1. Helix sequence flanked by linkers. |
| 42 | MDIDPYKEFGASVELLSFLPSDFFPSIRDLLDTASALYREALESPEHCSPHHTALRQAILCWGELMNLATWGGGDQKSTQNAINGITNKVNSVIEKGGGVGSNLEDPASGGGDQKSTQNAINGITNKVNSVIEKGGGRELVVSYVNVNMGLKIRQLLWFHISCLTFGRETVLEYLVSFGVWIRTPPAYRPPNAPILSTLPETTVVRRRGRSPRRRTPSPRRRRSQSPRRRRSQSRESQC | HBcAg with inserted helix A sequence from influenza H1. Helix sequence flanked by linkers. |

TABLE 1-continued

| SEQ ID NO | Sequence | Notes |
|---|---|---|
| 43 | MDIDPYKEFGASVELLSFLPSDFFPSIRDLLDTASALYREALESPEHC SPHHTALRQAILCWGELMNLATWGGGDQKSTQNAINGITNKVNTVIEK GGGVGSNLEDPASGGGDQKSTQNAINGITNKVNTVIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H1. Helix sequence flanked by linkers. |
| 44 | MDIDPYKEFGASVELLSFLPSDFFPSIRDLLDTASALYREALESPEHC SPHHTALRQAILCWGELMNLATWGGGDKESTQKAFDGITNKVNAVIEK GGGVGSNLEDPASGGGDKESTQKAFDGITNKVNAVIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H2. Helix sequence flanked by linkers. |
| 45 | MDIDPYKEFGASVELLSFLPSDFFPSIRDLLDTASALYREALESPEHC SPHHTALRQAILCWGELMNLATWGGGDKESTQKAFDGITNKVNSVIEK GGGVGSNLEDPASGGGDKESTQKAFDGITNKVNSVIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H2. Helix sequence flanked by linkers. |
| 46 | MDIDPYKEFGASVELLSFLPSDFFPSIRDLLDTASALYREALESPEHC SPHHTALRQAILCWGELMNLATWGGGDLKSTQAAIDQINGKLNRLIGK GGGVGSNLEDPASGGGDLKSTQAAIDQINGKLNRLIGKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 47 | MDIDPYKEFGASVELLSFLPSDFFPSIRDLLDTASALYREALESPEHC SPHHTALRQAILCWGELMNLATWGGGDLKSTQAAIDQINGKLNRLVEK GGGVGSNLEDPASGGGDLKSTQAAIDQINGKLNRLVEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 48 | MDIDPYKEFGASVELLSFLPSDFFPSIRDLLDTASALYREALESPEHC SPHHTALRQAILCWGELMNLATWGGGDLKSTQAAIDQINGKLNRVIEK GGGVGSNLEDPASGGGDLKSTQAAIDQINGKLNRVIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 49 | MDIDPYKEFGASVELLSFLPSDFFPSIRDLLDTASALYREALESPEHC SPHHTALRQAILCWGELMNLATWGGGDLKSTQAAINQINGKLNRLIEK GGGVGSNLEDPASGGGDLKSTQAAINQINGKLNRLIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 50 | MDIDPYKEFGASVELLSFLPSDFFPSIRDLLDTASALYREALESPEHC SPHHTALRQAILCWGELMNLATWGGGDLKSTQAAINQINGKLNRLIGK GGGVGSNLEDPASGGGDLKSTQAAINQINGKLNRLIGKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 51 | MDIDPYKEFGASVELLSFLPSDFFPSIRDLLDTASALYREALESPEHC SPHHTALRQAILCWGELMNLATWGGGDLKSTQAAINQITGKLNRVIKK GGGVGSNLEDPASGGGDLKSTQAAINQITGKLNRVIKKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H3. Helix sequence flanked by linkers. |
| 52 | MDIDPYKEFGASVELLSFLPSDFFPSIRDLLDTASALYREALESPEHC SPHHTALRQAILCWGELMNLATWGGGDLKSTQAAIDQINGKLNRLIEK GGGVGSNLEDPASGGGDLKSTQAAIDQINGKLNRLIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H4. Helix sequence flanked by linkers. |
| 53 | MDIDPYKEFGASVELLSFLPSDFFPSIRDLLDTASALYREALESPEHC SPHHTALRQAILCWGELMNLATWGGGDKESTQKAIDGITNKVNSIIDK GGGVGSNLEDPASGGGDKESTQKAIDGITNKVNSIIDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H5. Helix sequence flanked by linkers. |
| 54 | MDIDPYKEFGASVELLSFLPSDFFPSIRDLLDTASALYREALESPEHC SPHHTALRQAILCWGELMNLATWGGGDKESTQKAIDGVTNKVNSIIDK GGGVGSNLEDPASGGGDKESTQKAIDGVTNKVNSIIDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H5. Helix sequence flanked by linkers. |

TABLE 1-continued

| SEQ ID NO | Sequence | Notes |
|---|---|---|
| 55 | MDIDPYKEFGASVELLSFLPSDFFPSIRDLLDTASALYREALESPEHC SPHHTALRQAILCWGELMNLATWGGGDKESTQKAIDGVTNKVNSIINK GGGVGSNLEDPASGGGDKESTQKAIDGVTNKVNSIINKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H5. Helix sequence flanked by linkers. |
| 56 | MDIDPYKEFGASVELLSFLPSDFFPSIRDLLDTASALYREALESPEHC SPHHTALRQAILCWGELMNLATWGGGDYKSTQSAIDQITGKLNRLIGK GGGVGSNLEDPASGGGDYKSTQSAIDQITGKLNRLIGKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H7. Helix sequence flanked by linkers. |
| 57 | MDIDPYKEFGASVELLSFLPSDFFPSIRDLLDTASALYREALESPEHC SPHHTALRQAILCWGELMNLATWGGGDYKSTQSAIDQITGKLNRLIEK GGGVGSNLEDPASGGGDYKSTQSAIDQITGKLNRLIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H7. Helix sequence flanked by linkers. |
| 58 | MDIDPYKEFGASVELLSFLPSDFFPSIRDLLDTASALYREALESPEHC SPHHTALRQAILCWGELMNLATWGGGDQKSTQEAIDKITNKVNNIVDK GGGVGSNLEDPASGGGDQKSTQEAIDKITNKVNNIVDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H8. Helix sequence flanked by linkers. |
| 59 | MDIDPYKEFGASVELLSFLPSDFFPSIRDLLDTASALYREALESPEHC SPHHTALRQAILCWGELMNLATWGGGDRDSTQKAIDKITSKVNNIVDK GGGVGSNLEDPASGGGDRDSTQKAIDKITSKVNNIVDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H9. Helix sequence flanked by linkers. |
| 60 | MDIDPYKEFGASVELLSFLPSDFFPSIRDLLDTASALYREALESPEHC SPHHTALRQAILCWGELMNLATWGGGDRDSTQRAIDKITSKVNNIVDK GGGVGSNLEDPASGGGDRDSTQRAIDKITSKVNNIVDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H9. Helix sequence flanked by linkers. |
| 61 | MDIDPYKEFGASVELLSFLPSDFFPSIRDLLDTASALYREALESPEHC SPHHTALRQAILCWGELMNLATWGGGDYKSTQAAIDQITGKLNRIIKK GGGVGSNLEDPASGGGDYKSTQAAIDQITGKLNRIIKKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H10. Helix sequence flanked by linkers. |
| 62 | MDIDPYKEFGASVELLSFLPSDFFPSIRDLLDTASALYREALESPEHC SPHHTALRQAILCWGELMNLATWGGGDKESTQTAIDQITSKVNNIVDR GGGVGSNLEDPASGGGDKESTQTAIDQITSKVNNIVDRGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H11. Helix sequence flanked by linkers. |
| 63 | MDIDPYKEFGASVELLSFLPSDFFPSIRDLLDTASALYREALESPEHC SPHHTALRQAILCWGELMNLATWGGGDRDSTQRAIDNMQNKLNNVIDK GGGVGSNLEDPASGGGDRDSTQRAIDNMQNKLNNVIDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H12. Helix sequence flanked by linkers. |
| 64 | MDIDPYKEFGASVELLSFLPSDFFPSIRDLLDTASALYREALESPEHC SPHHTALRQAILCWGELMNLATWGGGDKESTQKAIDQITTKINNIIDK GGGVGSNLEDPASGGGDKESTQKAIDQITTKINNIIDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H13. Helix sequence flanked by linkers. |
| 65 | MDIDPYKEFGASVELLSFLPSDFFPSIRDLLDTASALYREALESPEHC SPHHTALRQAILCWGELMNLATWGGGDYKSTQAAIDQITGKLNRLIEK GGGVGSNLEDPASGGGDYKSTQAAIDQITGKLNRLIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H15. Helix sequence flanked by linkers. |
| 66 | MDIDPYKEFGASVELLSFLPSDFFPSIRDLLDTASALYREALESPEHC SPHHTALRQAILCWGELMNLATWGGGDKASTQKAIDEITTKINNIIEK GGGVGSNLEDPASGGGDKASTQKAIDEITTKINNIIEKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H16. Helix sequence flanked by linkers. |
| 67 | MDIDPYKEFGASVELLSFLPSDFFPSIRDLLDTASALYREALESPEHC SPHHTALRQAILCWGELMNLATWGGGDKEATQKAVDAITNKVNSIIDK GGGVGSNLEDPASGGGDKEATQKAVDAITNKVNSIIDKGGGRELVVSY | HBcAg with inserted helix A sequence from influenza H17. |

TABLE 1-continued

| SEQ ID NO | Sequence | Notes |
|---|---|---|
| | VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | Helix sequence flanked by linkers. |
| 68 | MDIDPYKEFGASVELLSFLPSDFFPSIRDLLDTASALYREALESPEHC SPHHTALRQAILCWGELMNLATWGGGDKEATQKAVDAITTKVNNIIDK GGGVGSNLEDPASGGGDKEATQKAVDAITTKVNNIIDKGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza H18. Helix sequence flanked by linkers. |
| 69 | MDIDPYKEFGASVELLSFLPSDFFPSIRDLLDTASALYREALESPEHC SPHHTALRQAILCWGELMNLATWGGGDLKSTQEAINKITKNLNSLSEL GGGVGSNLEDPASGGGDLKSTQEAINKITKNLNSLSELGGGRELVVSY VNVNMGLKIRQLLWFHISCLTFGRETVLEYLVSFGVWIRTPPAYRPPN APILSTLPETTVVRRRGRSPRRRTPSPRRRRSQSPRRRRSQSRESQC | HBcAg with inserted helix A sequence from influenza B. Helix sequence flanked by linkers. |
| 70 | DLKSTQNAIDEITNKVNSVIEK | Sequence of helix A from influenza H1 |
| 71 | DQKSTQNAINGITNKVNSIIEK | Sequence of helix A from influenza H1 |
| 72 | DQKSTQNAINGITNKVNSVIEK | Sequence of helix A from influenza H1 |
| 73 | DQKSTQNAINGITNKVNTVIEK | Sequence of helix A from influenza H1 |
| 74 | DKESTQKAFDGITNKVNAVIEK | Sequence of helix A from influenza H2 |
| 75 | DKESTQKAFDGITNKVNSVIEK | Sequence of helix A from influenza H2 |
| 76 | DLKSTQAAIDQINGKLNRLIGK | Sequence of helix A from influenza H3 |
| 77 | DLKSTQAAIDQINGKLNRLVEK | Sequence of helix A from influenza H3 |
| 78 | DLKSTQAAIDQINGKLNRVIEK | Sequence of helix A from influenza H3 |
| 79 | DLKSTQAAINQINGKLNRLIEK | Sequence of helix A from influenza H3 |
| 80 | DLKSTQAAINQINGKLNRLIGK | Sequence of helix A from influenza H3 |
| 81 | DLKSTQAAINQITGKLNRVIKK | Sequence of helix A from influenza H3 |
| 82 | DLKSTQAAIDQINGKLNRLIEK | Sequence of helix A from influenza H4/H3/H14 |
| 83 | DKESTQKAIDGITNKVNSIIDK | Sequence of helix A from influenza H5/H6 |
| 84 | DKESTQKAIDGVTNKVNSIIDK | Sequence of helix A from influenza H5 |

TABLE 1-continued

| SEQ ID NO | Sequence | Notes |
|---|---|---|
| 85 | DKESTQKAIDGVTNKVNSIINK | Sequence of helix A from influenza H5 |
| 86 | DYKSTQSAIDQITGKLNRLIGK | Sequence of helix A from influenza H7 |
| 87 | DYKSTQSAIDQITGKLNRLIEK | Sequence of helix A from influenza H7 |
| 88 | DQKSTQEAIDKITNKVNNIVDK | Sequence of helix A from influenza H8 |
| 89 | DRDSTQKAIDKITSKVNNIVDK | Sequence of helix A from influenza H9 |
| 90 | DRDSTQRAIDKITSKVNNIVDK | Sequence of helix A from influenza H9 |
| 91 | DYKSTQAAIDQITGKLNRIIKK | Sequence of helix A from influenza H10 |
| 92 | DKESTQTAIDQITSKVNNIVDR | Sequence of helix A from influenza H11 |
| 93 | DRDSTQRAIDNMQNKLNNVIDK | Sequence of helix A from influenza H12 |
| 94 | DKESTQKAIDQITTKINNIIDK | Sequence of helix A from influenza H13 |
| 95 | DYKSTQAAIDQITGKLNRLIEK | Sequence of helix A from influenza H15/H10 |
| 96 | DKASTQKAIDEITTKINNIIEK | Sequence of helix A from influenza H16 |
| 97 | DKEATQKAVDAITNKVNSIIDK | Sequence of helix A from influenza H17 |
| 98 | DKEATQKAVDAITTKVNNIIDK | Sequence of helix A from influenza H18 |
| 99 | DLKSTQEAINKITKNLNSLSEL | Sequence of helix A from influenza B |

As used herein, the terms "corresponding", "corresponding to", "corresponds to," and the like, refer to a structural and/or functional similarity between regions in two or more different proteins. Regions in different proteins are considered to correspond when they perform the same function and/or have nearly identical amino acid sequences and/or three-dimensional structures. For example, the stem regions of HA proteins from two different subtypes of influenza virus would be corresponding regions because they both serve to connect the membrane region to the head region. Corresponding regions of proteins may, but need not, have similar or identical sequences. Moreover, due to sequence variability in corresponding proteins between different species, which may include insertions and deletions of amino acids, corresponding regions may not be present in identical linear locations in the proteins. For example, while helix A of influenza virus California/07/09 may span amino acids 380-402, the corresponding region in a different subtype of influenza virus may, but need not, span, for example, amino acids 380-400, 380-401, or 381-403. Methods of identifying and comparing corresponding regions of HA proteins are known to those skilled in the art.

Helix A from the stem region of an influenza HA protein may refer to a region in an influenza HA protein comprising the amino acid sequence DLKSTQNAIDEITNKVNSVIEK (SEQ ID NO:2 and SEQ ID NO:70), or variants thereof (e.g., SEQ ID NOs: 71-99). Helix A may comprise a sequence corresponding to about amino acid 381 to about amino acid 402 of SEQ ID NO:1. Helix A may comprise a sequence at least 50%, at least 90%, at least 95%, at least 97% or at least 99% identical to a sequence selected from the group consisting of SEQ ID NOs:70-99. Helix A consists of a sequence at least 50%, at least 90%, at least 95%, at least 97% or at least 99% identical to a sequence selected from the group consisting of SEQ ID NOs:70-99. Helix A may comprise a sequence selected from the group consisting of SEQ ID NOs:70-99. Helix A may consist of a sequence selected from the group consisting of SEQ ID NOs:70-99.

As used herein, hepatitis B virus core antigen (HBcAg) refers to the hepatitis B virus protein that makes up the nucleocapsid core of hepatitis B virus. The terms hepatitis B core antigen, and hepatitis B core protein (core), can be used interchangeably herein. A HBcAg useful for practicing methods of this disclosure can be a HBcAG from any wild-type HBV, a variant thereof, or a modified form thereof. As used herein, the term "modified" refers to a protein or nucleic acid molecule, the properties of which have been altered by the hand of man so that it differs in sequence and/or structure from the same protein or nucleic acid molecule found in nature. For example, a nucleic acid molecule in which the nucleotide sequence has been altered using recombinant techniques would be considered a modified nucleic acid molecule. Such alterations include, but are not limited to, substitution of one or more nucleotides, deletion of one or more nucleotides, insertion of one or more nucleotides, and incorporation of one or more nucleotide analogues. Likewise, a protein, the sequence of which has been altered by the hand of man, is a modified protein. Such modifications include, but are not limited to, substitution, deletion, and/or insertion of one or more amino acids, and the like. Modified proteins include those proteins in which an entire region has been substituted with an amino acid sequence from a protein from a related or unrelated organism.

One example of a HBcAg protein useful for practicing methods of this disclosure is represented by SEQ ID NO:3. HBcAgs used to practice methods of this disclosure may comprise an amino acid sequence at least 50%, at least 90%, at least 95%, at least 95%, at least 99%, or 100% sequence identity with SEQ ID NO:3.

Fusion proteins of this disclosure comprise an immunogenic peptide from an influenza virus HA protein joined to a HBcAg α3 helix, and/or a HBcAg α4 helix. As used herein, a HBcAg α3 helix, α3 helix, α3 helix sequence, refer to an amino acid sequence corresponding to the amino acid sequence of the α3 helix region of the HBcAG protein represented by SEQ ID NO:3. The α3 helix region of the HBcAG represented by SEQ ID NO:3 consists of about amino acid 50 to about amino acid 73 of SEQ ID NO:3. As used herein, the word "about", with regard to the amino acid sequences of HBcAg helical sequences, means+/−3 amino acids. For example, the α3 helix region of the HBcAG represented by SEQ ID NO:3 can consist of amino acids 49-70, amino acids 50-71, amino acids 51-71, or amino acids 49-72. Variants of HBcAg α3 helices can also be used in the present invention, so long as the variant sequence is capable of forming a helix capable of associating with a HBcAg α4 helix to form the afore-mentioned spike-like, monomeric subunit. An HBcAg α3 helix of this disclosure comprises an amino acid sequence at least 50%, at least 90%, at least 95%, at least 97%, at least 99%, or 100% identical to the amino acid sequence of an HBcAg α3 helix from a wild-type HBV. An HBcAg α3 helix of this disclosure comprises an amino acid sequence at least 50%, at least 90%, at least 95%, at least 97%, or at least 99% identical to a sequence selected from the group consisting of SEQ ID NO:5, SEQ ID NO:6, SEQ ID NO:7 and SEQ ID NO:8. An HBcAg α3 helix of this disclosure consists of an amino acid sequence at least 50%, at least 90%, at least 95%, at least 97%, or at least 99% identical to a sequence selected from the group consisting of SEQ ID NO:5, SEQ ID NO:6, SEQ ID NO:7, and SEQ ID NO:8. An HBcAg α3 helix of this disclosure may comprise a sequence selected from the group consisting of SEQ ID NO:5, SEQ ID NO:6, SEQ ID NO:7, and SEQ ID NO:8. An HBcAg α3 helix of this disclosure may consist of a sequence selected from the group consisting of SEQ ID NO:5, SEQ ID NO:6, SEQ ID NO:7, and SEQ ID NO:8.

Fusion proteins of this disclosure may comprise an immunogenic peptide from an influenza virus HA protein joined to an HBcAg α4 helix. As used herein, a HBcAg α4 helix refers to an amino acid sequence corresponding to the amino acid sequence of the α4 helix region of the HBcAG protein represented by SEQ ID NO:3. The α4 helix region of the HBcAG represented by SEQ ID NO:3 consists of about amino acid 79 to about amino acid 110. For example, the α4 helix region of the HBcAG represented by SEQ ID NO:3 may consist of amino acids 82-110, amino acids 82-109, amino acids 79-109, or amino acids 80-110. Variants of HBcAg α4 helices can also be used in the present invention, so long as the variant sequence is capable of forming a helix that can associate with a HBcAg as helix to form the afore-mentioned spike-like, monomeric subunit. An HBcAg α4 helix of this disclosure may comprise an amino acid sequence at least 50%, at least 90%, at least 95%, at least 97%, at least 99%, or 100% identical to the amino acid sequence of an HBcAg α4 helix from a wild-type HBV. A HBcAg α4 helix of this disclosure may comprise an amino acid sequence at least 50%, at least 90%, at least 95%, at least 97%, or at least 99% identical to the amino acid sequence of the HBcAg α4 helix of SEQ ID NO:3. An HBcAg α4 helix of this disclosure may comprise an amino acid sequence at least 50%, at least 90%, at least 95%, at least 97%, or at least 99% identical to a sequence selected from the group consisting of SEQ ID NOs:9, 10, 11, and 12. An HBcAg α4 helix of this disclosure may consist of an amino acid sequence at least 50%, at least 90%, at least 95%, at least 97%, or at least 99% identical to a sequence selected from the group consisting of SEQ ID NOs:9, 10, 11, and 12. An HBcAg α4 helix of this disclosure comprises a sequence selected from the group consisting of SEQ ID NOs:9, 10, 11, and 12. An HBcAg α4 helix of this disclosure may consist of a sequence selected from the group consisting of SEQ ID Nos:9, 10, 11, and 12.

The HBcAG α4 helix is made of two closely spaced helices referred to as α4a and α4b. The α4a helix sequence resides at the amino-terminal end of the α4 helix, and consists of any one of amino acids 79-82 to about amino acid 90 of SEQ ID NO:3. The α4b helix sequence, which is represented by SEQ ID NO:17, lies downstream of the α4a helix sequence and consists of amino acids 92-110 of SEQ ID NO:3. Thus, the immunogenic peptide is joined to the amino-terminal end of the α4a helix, which is represented by a sequence selected from the group consisting of SEQ ID NOs:13, 14, 15, and 16.

Fusion proteins of this disclosure can self-assemble into virus-like particles. As used herein, a virus-like particle (VLP) is a particle comprising one or more viral capsid proteins (e.g., HBcAg), which self-assemble into a roughly spherical particle, such that the three-dimensional conformation of the VLP mimics the conformation, and usually the antigenicity, of the authentic native virus from which the capsid originates. An HBV VLP is a nanoparticle made from dimerized HBcAg monomeric subunits that mimics the three-dimensional shape and/or the antigenicity of an HBV core. VLPs of this disclosure lack sufficient nucleic acid sequences that enable autonomous replication of the VLP. That is, upon entry of a VLP into a cell, the VLP is unable to autonomously initiate or implement the production of VLPs or virus particles. Accordingly, VLPs lack the genome of the virus from which the capsid proteins originate. VLPs also typically lack functional nucleic acid sequences encoding functional replicase proteins, or capsid proteins of the virus from which the VLP coat protein originates. Generally, VLPs are envisioned by those skilled in the art as empty shells made from viral capsid proteins, and which lack any appreciable nucleic acid molecules. However, VLPs may, but need not, contain a small amount of nucleic acid molecules, which are unrelated to the virus from which the VLP capsid protein originates. As used herein, unrelated nucleic acid molecules are molecules from an organism in a family other than the family of the virus from which the VLP capsid proteins originate. For example, during assembly of an HBV VLP, a small amount of host DNA, or RNA, may be packaged within the VLP. The packaged human DNA/RNA would be considered unrelated to HBV. VLPs and methods of producing VLPs are well known to those skilled in relevant arts.

As has been discussed, it is known that if only a portion (e.g., approximately one half) of an HBcAg is produced, this HBcAg portion is still able to assemble into a VLP, so long as the other half of the HBcAg is provided in trans. For example, when a protein consisting of amino acid 1 to approximately amino acid 78 of a HBcAG (coreN) is mixed with a protein consisting of about amino acid 80 to about amino acid 149 (or about 183) of a HBcAG (coreC), the two proteins will associate to form HBcAg monomeric subunits, which can self-assemble into VLPs. Moreover, such VLPs (or core-like particles; CLPs) can display on their surface any sequence attached to either the coreN or coreC protein. Thus, such a construct allows each coreN/coreC complex to display at least two copies of an immunogenic sequence. Alternatively, each of the coreN and coreC proteins can be joined with different immunogenic peptides, allowing each coreN/coreC complex to display two different immunogenic sequences. Such a system is referred to as a split-core system, as disclosed in U.S. Pat. No. 8,282,932, which is incorporated herein by reference in its entirety.

One aspect of this disclosure is a fusion protein comprising an immunogenic peptide from helix A in the stem region of an influenza hemagglutinin protein, joined to an amino acid sequence comprising at least 30, at least 40, at least 50, or at least 60 contiguous amino acids from the polypeptide sequence immediately upstream of the HBcAg c/e1 loop sequence, wherein the amino acid sequence comprises an HBcAg α3 helix sequence. As used herein, a c/e1 loop refers to a sequence corresponding to the sequence connecting the carboxy-terminal end of the HBcAg α3 helix sequence with the amino-terminal end of the HBcAg α4 helix sequence in a wild-type HBcAg. In certain embodiments, the c/e1 loop consists of a sequence corresponding to sequence consisting of about amino acid 72 to about amino acid 81 of a wild-type HBcAg. The c/e1 loop may consist of a sequence corresponding to about amino acid 72 to about amino acid 81 of SEQ ID NO:3. The c/e1 loop may consist of a sequence in a wild-type HBcAG corresponding to VGSNLEDPAS (SEQ ID NO:18). The c/e1 loop may consist of a sequence in a wild-type HBcAG corresponding to SNLEDPAS (SEQ ID NO:19). The c/e1 loop may consist of a sequence in a wild-type HBcAG corresponding to VGSNLED (SEQ ID NO:20). The c/e1 loop may consist of a sequence in a wild-type HBcAG corresponding to SNLED (SEQ ID NO:21). The c/e1 loop may consist of VGSNLEDPAS (SEQ ID NO:18), SNLEDPAS (SEQ ID NO:19), VGSNLED (SEQ ID NO:20) or SNLED (SEQ ID NO:21). In certain embodiments, the fusion protein may form a virus-like particle (VLP) when combined with a HAcAg-C protein.

The immunogenic peptide may be joined to the carboxyl-terminal end of the HBcAg α3 helix sequence. The amino acid sequence may comprise at least 30, at least 40, at least 50, or at least 60 contiguous amino acids from the polypeptide sequence immediately upstream of any one of amino acids 72-82 of a wild-type HBcAg (e.g., SEQ ID NO:3). The amino acid sequence may be at least 50%, at least 90%, at least 95%, at least 97%, at least 99% or 100% identical to at least 30, at least 40, at least 50, or at least 60 contiguous amino acids from the polypeptide sequence immediately upstream of any one of amino acids 72-82 of SEQ ID NO:3. The amino acid sequence may comprise a polypeptide sequence at least 50%, at least 90%, at least 95%, at least 97%, or at least 99% identical to a sequence selected from the group consisting of SEQ ID NOs:22, 23, 24, 25, 30, 31, 32, and 33. The amino acid sequence may comprise a polypeptide sequence selected from the group consisting of SEQ ID NOs: 22, 23, 24, 25, 30, 31, 32, and 33.

Another aspect of this disclosure is a fusion protein comprising an immunogenic peptide from helix A in the stem region of an influenza hemagglutinin protein joined to an amino acid sequence comprising at least 50, at least 60, or at least 70 contiguous amino acids from the polypeptide sequence immediately downstream of the HBcAg c/e1 loop sequence, wherein the amino acid sequence comprises an HBcAg α4 helix sequence. The amino acid sequence may comprise at least 50, at least 60, or at least 70 contiguous amino acids from the polypeptide sequence immediately downstream of any one of amino acids 72-82 of a wild-type HBcAg, wherein the amino acid sequence comprises an HBcAg α4 helix sequence. The amino acid sequence may be at least 50%, at least 90%, at least 95%, at least 97%, at least 99% or 100% identical to at least 50, at least 60, or at least 70 contiguous amino acids from the polypeptide sequence immediately downstream of any one of amino acids 72-82 of a wild-type HBcAg, wherein the amino acid sequence comprises an HBcAg α4 helix sequence. The amino acid sequence may comprise a polypeptide sequence at least 50%, at least 90%, at least 95%, at least 97%, or at least 99% identical to a sequence selected from the group consisting of SEQ ID NOs:26, 27, 28, 29, 34, 35, 36, and 37. The amino acid sequence may comprise a polypeptide sequence selected from the group consisting of SEQ ID NOs: 26, 27, 28, 29, 34, 35, 36, and 37. In certain embodiments, the fusion protein may form a virus-like particle (VLP) when combined with a HAcAG-N protein.

In such fusion proteins, helix A comprises an amino acid sequence corresponding to a region in an influenza HA protein comprising DLKSTQNAIDEITNKVNSVIEK (SEQ ID NO:2 and SEQ ID NO:70), or variants thereof (e.g., SEQ ID NOs: 71-99). Alternatively or additionally, Helix A may comprise a sequence corresponding to about amino acid 381 to about amino acid 402 of SEQ ID NO:1. Helix A may comprise a sequence at least 50%, at least 90%, at least 95%, at least 97% or at least 99% identical to a sequence selected from the group consisting of SEQ ID NOs: 70-99. Helix A may consist of a sequence at least 50%, at least 90%, at least 95%, at least 97% or at least 99% identical to a sequence selected from the group consisting of SEQ ID NOs: 70-99. Helix A may comprise a sequence selected from the group consisting of SEQ ID NOs: 70-99, or consist of a sequence selected from the group consisting of SEQ ID NOs: 70-99.

Another aspect of this disclosure is a fusion protein comprising an immunogenic peptide from helix A in the stem region of an influenza hemagglutinin protein, joined to the carboxy-terminal end of a coreN domain of a HBcAG. As used herein, a coreN domain from an HBcAg is an amino acid sequence corresponding to approximately the first amino acid of a mature HBcAg to the carboxyl end of the HBcAg α3 helix sequence. A coreN sequence may consist of a sequence corresponding to a sequence consisting of about amino acid 1 to about amino acid 71-79 of SEQ ID NO:3. A coreN sequence may consist of a sequence at least 50%, at least 90%, at least 95%, at least 97%, at least 99%, or 100% identical to a sequence consisting of about amino acid 1 to about amino acids 71-79 of SEQ ID NO:3. A coreN sequence may consist of a sequence at least 50%, at least 90%, at least 95%, at least 97%, at least 99% or 100% identical to a sequence selected from the group consisting of SEQ ID NOs:30, 31, 32, and 33. A coreN sequence contains the HBcAg α3 helix sequence at its carboxy-terminal end. Thus, the immunogenic peptide from helix A may be joined to the carboxy-terminal end of the HBcAg α3 helix sequence present in the coreN domain. In certain embodiments, the fusion protein may form a virus-like particle (VLP) when combined with a HAcAg-C protein.

Another aspect of this disclosure is a fusion protein comprising an immunogenic peptide from helix A from the stem region of an influenza hemagglutinin protein, joined to the amino-terminal end of a coreC domain of a HBcAG. As used herein, a coreC domain from an HBcAg is an amino acid sequence corresponding to about the first amino acid following the c/e1 loop sequence of a mature HBcAg to an amino acid between about amino acid 143 and amino acid 183 of a wild-type HBcAg. A coreC sequence may consist of a sequence corresponding to about amino acid 80-82 of SEQ ID NO:3 to an amino acid between about amino acid 143 and amino acid 183 of SEQ ID NO:3. A coreC sequence may consist of a sequence at least 50%, at least 90%, at least 95%, at least 97%, at least 99%, or 100% identical to a sequence consisting of about amino acid 80-82 of SEQ ID NO:3 to an amino acid between about amino acid 143 and amino acid 183 of SEQ ID NO:3. A coreC sequence may consist of a sequence at least 50%, at least 90%, at least 95%, at least 97%, at least 99%, or 100% identical to a sequence selected from the group consisting of SEQ ID NOs:34, 35, 36, and 37. The coreC sequence contains the HBcAg α4 helix sequence at its amino-terminal end. Thus, the immunogenic peptide from helix A may be joined to the amino-terminal end of the HBcAg α4 helix sequence present in the coreC domain. In certain embodiments, the fusion protein may form a virus-like particle (VLP) when combined with a HAcAG-N protein.

Helix A may comprise an amino acid sequence corresponding to a region in an influenza HA protein comprising DLKSTQNAIDEITNKVNSVIEK (SEQ ID NO:2 and SEQ ID NO:70), or variants thereof (e.g., SEQ ID NOs: 71-99). Helix A may comprise a sequence corresponding to about amino acid 381 to about amino acid 402 of SEQ ID NO:1.

Helix A may comprise a sequence at least 50%, at least 90%, at least 95%, at least 97% or at least 99% identical to a sequence selected from the group consisting of SEQ ID NOs:70-99. Helix A may consist of a sequence at least 50%, at least 90%, at least 95%, at least 97% or at least 99% identical to a sequence selected from the group consisting of SEQ ID NOs:70-99. Helix A may comprise a sequence selected from the group consisting of SEQ ID NOs:70-99, or consist of a sequence selected from the group consisting of SEQ ID NOs:70-99.

Another aspect of this disclosure is a fusion protein comprising:
a) an immunogenic peptide from helix A in the stem region of an influenza hemagglutinin protein;
b) a first amino acid sequence comprising at least 25, at least 40, at least 50, or at least 60 contiguous amino acids from the polypeptide sequence immediately upstream of the HBcAg c/e1 loop sequence in a wild-type HBcAg, wherein the first amino acid sequence comprises an HBcAg α3 helix sequence; and
c) a second amino acid sequence comprising at least 50, at least 60, or at least 70 contiguous amino acids from the polypeptide sequence immediately downstream of the HBcAg c/e1 loop sequence in a wild-type HBcAg, wherein the second amino acid sequence comprises an HBcAg α4 helix sequence;
wherein one end of the immunogenic peptide is joined to the carboxy-terminal end of the first amino acid sequence, and the other end of the immunogenic peptide is joined to the amino-terminal end of the second amino acid sequence; and,
wherein the fusion protein self assembles into a VLP.

In these fusion proteins, the first fusion protein may form a virus-like particle (VLP) when combined with a HAcAG-C protein. The second fusion protein may form a virus-like particle (VLP) when combined with a HAcAG-N protein.

The amino-terminal end of the immunogenic peptide may be joined to the carboxy-terminal end of the HBcAg α3 helix sequence. The carboxy-terminal end of the immunogenic peptide may be joined to the amino-terminal end of the HBcAg α4 helix sequence.

In certain aspects, the c/e1 loop may consist of VGSNLEDPAS (SEQ ID NO:18), SNLEDPA (SEQ ID NO:19)S, VGSNLED (SEQ ID NO:20), or SNLED (SEQ ID NO:21). The immunogenic peptide may be joined to the carboxyl-terminal end of the HBcAg α3 helix sequence.

The first amino acid sequence comprises at least 30, at least 40, at least 50, or at least 60 contiguous amino acids from the polypeptide sequence immediately upstream of any one of amino acids 72-82 of a wild-type HBcAg. The first amino acid sequence is at least 50%, at least 90%, at least 95%, at least 97%, at least 99%, or 100% identical to at least 25, at least 40, at least 50, or at least 60 contiguous amino acids from the polypeptide sequence immediately upstream of any one of amino acids 72-82 of SEQ ID NO:3. The first amino acid sequence may comprise a polypeptide sequence at least 50%, at least 90%, at least 95%, at least 97%, or at least 99% identical to a sequence selected from the group consisting of SEQ ID NOs:22, 23, 24, 25, 30, 31, 32, and 33. The amino acid sequence may comprise a polypeptide sequence selected from the group consisting of SEQ ID NOs: 22, 23, 24, 25, 30, 31, 32, and 33.

The second amino acid sequence may comprise at least 50, at least 60, or at least 70 contiguous amino acids from the polypeptide sequence immediately downstream of any one of amino acids 72-82 of a wild-type HBcAg. The second amino acid sequence may be at least 50%, at least 90%, at least 95%, at least 97%, at least 99%, or 100% identical to at least 25, at least 40, at least 50, or at least 60 contiguous amino acids from the polypeptide sequence immediately downstream of any one of amino acids 72-82 of SEQ ID NO:3. The second amino acid sequence may comprise a polypeptide sequence at least 50%, at least 90%, at least 95%, at least 97%, or at least 99% identical to a sequence selected from the group consisting of SEQ ID NOs:26, 27, 28, 29, 34, 35, 36, and 37. The second amino acid sequence may comprise a polypeptide sequence selected from the group consisting of SEQ ID NOs: 26, 27, 28, 29, 34, 35, 36, and 37.

In these fusion proteins, helix A may comprise an amino acid sequence corresponding to a region in an influenza HA protein comprising DLKSTQNAIDEITNKVNSVIEK (SEQ ID NO:2 and SEQ ID NO:70), or variants thereof (e.g., SEQ ID NOs: 71-99). Helix A may comprise a sequence corresponding to about amino acid 381 to about amino acid 402 from SEQ ID NO:1. Helix A may comprise a sequence at least 50%, at least 90%, at least 95%, at least 97% or at least 99% identical to a sequence selected from the group consisting of SEQ ID NOs: 70-99. Helix A may consist of a sequence at least 50%, at least 90%, at least 95%, at least 97% or at least 99% identical to a sequence selected from the group consisting of SEQ ID NOs: 70-99. Helix A may comprise a sequence selected from the group consisting of SEQ ID NOs: 70-99 or consist of a sequence selected from the group consisting of SEQ ID NOs: 70-99.

Another aspect of this disclosure is a fusion protein comprising:
a) an immunogenic peptide from helix A in the stem region of an influenza hemagglutinin protein;
b) an HBcAg coreN domain; and,
c) an HBcAg coreC domain;
wherein one end of the immunogenic peptide is joined to the carboxy-terminal end of the coreN domain;
the other end of the immunogenic peptide is joined to the amino-terminal end of the coreC domain; and,
the fusion protein self-assembles into a VLP.

The coreN domain sequence may consist of a sequence corresponding to a sequence consisting of about amino acid 1 to about any one of amino acids 71-79 of SEQ ID NO:3. A coreN domain sequence may consist of a sequence at least 50%, at least 90%, at least 95%, at least 97%, at least 99% or 100% identical to a sequence consisting of about amino acid 1 to about any one of amino acids 71-79 of SEQ ID NO:3.

The coreC domain sequence may consist of a sequence corresponding to about any one of amino acids 80-82 of SEQ ID NO:3 to an amino acid between about amino acid 143 and amino acid 183 of SEQ ID NO:3. A coreC sequence may consist of a sequence at least 50%, at least 90%, at least 95%, at least 97%, at least 99%, or 100% identical to a sequence consisting of about any one of amino acids 80-82 of SEQ ID NO:3 to an amino acid between about amino acid 143 and amino acid 183 of SEQ ID NO:3.

The amino-terminal end of the immunogenic peptide may be joined to the carboxy-terminal end of the HBcAg α3 helix sequence in the coreN domain. The carboxy-terminal end of the immunogenic peptide may be joined to the amino-terminal end of the HBcAg α4 helix sequence in the coreC domain.

Helix A may comprise an amino acid sequence corresponding to a region in an influenza HA protein comprising DLKSTQNAIDEITNKVNSVIEK (SEQ ID NO:2 and SEQ ID NO:70), or variants thereof (e.g., SEQ ID NOs: 71-99). Helix A may comprise a sequence corresponding to the amino acids between about amino acid 381 and about amino acid 402 of SEQ ID NO:1. Helix A may comprise a sequence at least 50%, at least 90%, at least 95%, at least 97%, or at least 99% identical to a sequence selected from the group consisting of SEQ ID NOs:70-99. Helix A may consist of a sequence at least 50%, at least 90%, at least 95%, at least 97%, or at least 99% identical to a sequence selected from the group consisting of SEQ ID NOs:70-99. Helix A may comprise a sequence selected from the group consisting of SEQ ID NOs:70-99, or consist of a sequence selected from the group consisting of SEQ ID NOs:70-99.

Another aspect of this disclosure is a fusion protein comprising the amino acid sequence of a hepatitis B virus core antigen (HBcAg), wherein the fusion protein comprises in the HBcAg c/e1 loop, an immunogenic peptide from helix A from the stem region of an influenza virus hemagglutinin (HA) protein. The c/e1 loop may consist of a sequence corresponding to about amino acid 72 to about amino acid 81 of a HBcAg from a wild-type HBV. The c/e1 loop may consist of a sequence corresponding to the sequence from about amino acid 72 to about amino acid 81 of SEQ ID NO:3.

The immunogenic peptide can be present at any point in the sequence of the c/e1 loop. The immunogenic peptide may be inserted between the α3 helix sequence and the c/e1 loop sequence. The immunogenic peptide may be inserted between the c/e1 loop sequence and the α4 helix sequence. The immunogenic peptide may be inserted between the α3 helix sequence and the α4 helix sequence. The immunogenic peptide may be inserted between two or more amino acids within the c/e1 loop sequence. One or more amino acid residues of the c/e1 loop may be replaced by the immunogenic peptide.

The immunogenic peptide may be directly joined to the HBcAg amino acid sequences. The immunogenic peptide may be joined to the HBcAg amino acid sequences through linker sequences. Suitable linker sequences are provided in this disclosure.

More than one immunogenic peptide may be inserted into the c/e1 loop sequence. The multiple immunogenic peptides may comprise the same epitope, or they can comprise different epitopes. In embodiments in which the multiple epitopes differ, the multiple epitopes can be from the same virus (e.g., influenza A), or they can be from different viruses (e.g., influenza A and influenza B). They can also be from different organisms (e.g., influenza A and a pneumococcal bacteria).

Multiple immunogenic peptides may be inserted into the c/e1 loop, and the immunogenic peptides are inserted in tandem, i.e., the multiple immunogenic peptides are directly joined to one another. Individual copies of the immunogenic peptide may be separated by a linker sequence.

Multiple immunogenic peptides may also be inserted into the c/e1 loop such that each immunogenic peptide is inserted at a different location in the c/e1 loop sequence. For example, if the c/e1 loop region consists of W-VGSNLED-PAS-R, wherein the c/e1 loop sequence consists of VGSNLEDPAS (SEQ ID NO:18), one immunogenic peptide might be inserted between the tryptophan at the carboxy-terminal end of the α3 helix and the first valine of the c/e1 loop, and the second immunogenic peptide may be inserted between the last serine of the c/e1 loop and the arginine at the amino-terminal end of the α4 helix. The immunogenic peptide may be joined directly to HBcAg amino acids. The immunogenic peptide may be joined to HBcAg amino acids using one or more linked sequences.

The fusion protein may comprise an amino acid sequence at least 80%, at least 90%, at least 95%, at least 97%, at least 99%, or 100% identical to a sequence selected from the group consisting of SEQ ID NOs:38-69. The fusion protein may consist of an amino acid sequence at least 80%, at least 90%, at least 95%, at least 97%, at least 99%, or 100% identical to SEQ ID NOs:38-69. The fusion protein may consist of SEQ ID NOs:38-69.

Another aspect of this disclosure is nucleic acid molecule encoding a fusion protein of this disclosure. As used herein a nucleic acid construct is a recombinant expression vector, i.e., a vector linked to a nucleic acid molecule encoding a protein such that the nucleic acid molecule can affect expression of the protein when the nucleic acid construct is administered to a subject an organ, a tissue, or cell. The vector also enables transport of the nucleic acid molecule to a cell within an organism, tissue, or cell culture. Nucleic acid constructs of this disclosure may be produced by human intervention. These nucleic acid constructs may be DNA, RNA or variants thereof. The vector may be a DNA plasmid, a viral vector, or other vector. A vector may be a cytomegalovirus (CMV), retrovirus, adenovirus, adeno-associated virus, herpes virus, vaccinia virus, poliovirus, sindbis virus, or any other DNA or RNA virus vector. A vector may be a pseudotyped lentiviral or retroviral vector. A vector may be a DNA plasmid. A vector may be a DNA plasmid comprising viral components and plasmid components to enable nucleic acid molecule delivery and expression. Methods for the construction of nucleic acid constructs of this disclosure are well known. See, for example, *Molecular Cloning: A Laboratory Manual*, 3$^{rd}$ edition, Sambrook et al. 2001 Cold Spring Harbor Laboratory Press, and *Current Protocols in Molecular Biology*, Ausubel et al. eds., John Wiley & Sons, 1994. The vector may be a DNA plasmid, such as a CMV/R plasmid such as CMV/R or CMV/R 8 KB (also referred to herein as CMV/R 8 kb). Examples of CMV/R and CMV/R 8 kb are provided herein. CMV/R are also described in U.S. Pat. No. 7,094,598 B2, which is incorporated herein by reference.

Thus, one aspect of this disclosure is a VLP comprising one or more fusion proteins of this disclosure. A VLP of this disclosure may be a VLP comprising one or more fusion proteins selected from thee group consisting of:
a) a first fusion protein comprising an immunogenic peptide from an influenza HA protein stem region helix A sequence, joined to the carboxyl-terminal end of the α3 helix from a hepatitis B core antigen (HBcAg); and,
b) a second fusion protein comprising an immunogenic peptide from helix A from the stem region of an influenza hemagglutinin (HA) protein, joined to the amino-terminal end of the α4 helix from a hepatitis B core antigen (HBcAg).

The first fusion protein may comprise at least 30, at least 40, at least 50, or at least 60 contiguous amino acids from the polypeptide sequence immediately upstream of any one of amino acids 72-82 of a wild-type HBcAg. The first fusion protein may comprise at least 50%, at least 90%, at least 95%, at least 97%, at least 99%, or 100% identical to at least 25, at least 40, at least 50, or at least 60 contiguous amino acids from the polypeptide sequence immediately upstream of any one of amino acids 72-82 of SEQ ID NO:3. The first fusion protein may comprise a polypeptide sequence at least 50%, at least 90%, at least 95%, at least 97%, or at least 99% identical to a sequence selected from the group consisting of SEQ ID NOs:22, 23, 24, 25, 30, 31, 32, and 33. The first fusion protein may comprise a polypeptide sequence selected from the group consisting of SEQ ID NOs: 22, 23, 24, 25, 30, 31, 32, and 33.

The second fusion protein may comprise at least 50, at least 60, or at least 70 contiguous amino acids from the polypeptide sequence immediately downstream of any one of amino acids 72-82 of a wild-type HBcAg. The second fusion protein may comprise at least 50%, at least 90%, at least 95%, at least 97%, at least 99%, or 100% identical to at least 25, at least 40, at least 50, or at least 60 contiguous amino acids from the polypeptide sequence immediately downstream of any one of amino acids 72-82 of SEQ ID NO:3. The second fusion protein may comprise a polypeptide sequence at least 50%, at least 90%, at least 95%, at least 97%, or at least 99% identical to a sequence selected from the group consisting of SEQ ID NOs:26, 27, 28, 29, 34, 35, 36, and 37. The second fusion protein may comprise a polypeptide sequence selected from the group consisting of SEQ ID NOs: 26, 27, 28, 29, 34, 35, 36, and 37.

In certain embodiments, the first fusion protein may form a virus-like particle (VLP) when combined with a HAcAg-C protein. In certain embodiments, the second fusion protein may form a virus-like particle (VLP) when combined with a HAcAG-N protein.

The helix A sequence may comprise a sequence in an influenza HA protein corresponding to amino acids 38-58 of SEQ ID NO:1. The helix A may comprise a sequence at least 50%, at least 90%, at least 95%, at least 97% or at least 99% identical to a sequence selected from the group consisting of SEQ ID NOs:70-99. Helix A may consist of a sequence at least 50%, at least 90%, at least 95%, at least 97%, or at least 99% identical to a sequence selected from the group consisting of SEQ ID NOs:70-99. Helix A may comprise a sequence selected from the group consisting of SEQ ID NOs:70-99, or consist of a sequence selected from the group consisting of SEQ ID NOs:70-99.

HBcAgs used to practice methods of this disclosure may comprise an amino acid sequence at least 50%, at least 90%, at least 95%, at least 95%, at least 99%, or 100% identical to SEQ ID NO:2.

The HBcAg α3 helix comprises an amino acid sequence at least 50%, at least 90%, at least 95%, at least 97%, at least 99%, or 100% identical to the amino acid sequence of an HBcAg α3 helix from a wild-type HBV. The HBcAg α3 helix may comprise an amino acid sequence at least 50%, at least 90%, at least 95%, at least 97%, at least 99%, or 100% identical to a sequence selected from the group consisting of SEQ ID NOs:5, 6, 7, and 8.

The HBcAg α4 helix may comprise an amino acid sequence at least 50%, at least 90%, at least 95%, at least 97%, at least 99%, or 100% identical to the amino acid sequence of an HBcAg α4 helix from a wild-type HBV. The HBcAg α4 helix may comprise an amino acid sequence at least 50%, at least 90%, at least 95%, at least 97%, at least 99%, or 100% identical to a sequence selected from the group consisting of SEQ ID NOs:9, 10, 11, and 12.

This disclosure also provides is a VLP comprising at least one fusion protein selected from the group consisting of:
a) a first fusion protein comprising an immunogenic peptide from helix A from the stem region of an influenza HA protein, joined to a first amino acid sequence comprising at least 25, at least 40, at least 50, or at least 60 contiguous amino acids from the polypeptide sequence immediately upstream of the HBcAg c/e1 loop sequence, wherein the first amino acid sequence comprises an HBcAg α3 helix sequence; and, b) a second fusion protein comprising an immunogenic peptide from helix A in the stem region of an influenza hemagglutinin protein, joined to a second amino acid sequence comprising at least 50, at least 60, or at least 70 contiguous amino acids from the polypeptide sequence immediately downstream of the HBcAg c/e1 loop sequence, wherein the second amino acid sequence comprises an HBcAg α4 helix sequence.

In preferred embodiments, the first fusion protein may form a virus-like particle (VLP) when combined with a HAcAg-C protein. In preferred embodiments, the second fusion protein may form a virus-like particle (VLP) when combined with a HAcAG-N protein.

The c/e1 loop may consist of a sequence of about amino acid 72 to about amino acid 81 of a wild-type HBcAg. The c/e1 loop may consist of a sequence corresponding to about amino acid 72 to about amino acid 81 of SEQ ID NO:3. In certain aspects, the c/e1 loop may consist of a sequence in a wild-type HBcAG corresponding to VGSNLEDPAS (SEQ ID NO:18). In certain aspects, the c/e1 loop may consist of a sequence in a wild-type HBcAG corresponding to SNLEDPAS (SEQ ID NO:19). In certain aspects, the c/e1 loop may consist of a sequence in a wild-type HBcAG corresponding to VGSNLED (SEQ ID NO:20). In certain aspects, the c/e1 loop may consist of a sequence in a wild-type HBcAG corresponding to SNLED (SEQ ID NO:21). In certain aspects, the c/e1 loop may consist of VGSNLEDPAS, SNLEDPAS, VGSNLED, or SNLED.

The first the amino acid sequence may comprise at least 25, at least 40, at least 50, or at least 60 contiguous amino acids from the polypeptide sequence immediately upstream of any one of amino acids 72-82 of a wild-type HBcAg. The first amino acid sequence is at least 50%, at least 90%, at least 95%, at least 97%, at least 99%, or 100% identical to at least 25, at least 40, at least 50, or at least 60 contiguous amino acids from the polypeptide sequence immediately upstream of any one of amino acids 72-82 of SEQ ID NO:3. The first amino acid sequence may comprise a polypeptide sequence at least 50%, at least 90%, at least 95%, at least 97%, or at least 99% identical to a sequence selected from the group consisting of SEQ ID NOs:22, 23, 24, 25, 30, 31, 32, and 33. The first amino acid sequence may comprise a polypeptide sequence selected from the group consisting of SEQ ID NOs: 22, 23, 24, 25, 30, 31, 32, and 33.

The second amino acid sequence may comprise at least 50, at least 60, or at least 70 contiguous amino acids from the polypeptide sequence immediately downstream of any one of amino acids 72-82 of a wild-type HBcAg, wherein the amino acid sequence comprises an HBcAg α4 helix sequence. The amino acid sequence may be at least 50%, at least 90%, at least 95%, at least 97%, at least 99%, or 100% identical to at least 50, at least 60, or at least 70 contiguous amino acids from the polypeptide sequence immediately downstream of any one of amino acids 72-82 of SEQ ID NO:3. The second amino acid sequence may comprise a polypeptide sequence at least 50%, at least 90%, at least 95%, at least 97%, or at least 99% identical to a sequence selected from the group consisting of SEQ ID NOs:26, 27, 28, 29, 34, 35, 36, and 37. The second amino acid sequence may comprise a polypeptide sequence selected from the group consisting of SEQ ID NOs: 26, 27, 28, 29, 34, 35, 36, and 37.

One embodiment of this disclosure is a VLP comprising:
a) a first fusion protein comprising an immunogenic peptide from helix A from the stem region of an influenza hemagglutinin protein, joined to the carboxy-terminal end of a coreN domain sequence from a HBcAG; and, b) a second fusion protein comprising an immunogenic peptide from helix A in the stem region of an influenza hemagglutinin protein, joined to the amino-terminal end of a coreC domain sequence from a HBcAG.

In preferred embodiments, the first fusion protein may form a virus-like particle (VLP) when combined with a HAcAg-C protein. In preferred embodiments, the second fusion protein may form a virus-like particle (VLP) when combined with a HAcAG-N protein.

The coreN domain may consist of a sequence corresponding to a sequence consisting of about amino acid 1 to about amino acid 71-79 of SEQ ID NO:3. The coreN domain consists of a sequence at least 50%, at least 90%, at least 95%, at least 97%, at least 99%, or 100% identical to a sequence consisting of about amino acid 1 to about amino acid 71-79 of SEQ ID NO:3.

The coreC domain sequence consists of a sequence corresponding to amino acids 80-82 of SEQ ID NO:3 to an amino acid between about amino acid 143 and amino acid 183 of SEQ ID NO:3. The coreC sequence may consist of a sequence at least 50%, at least 90%, at least 95%, at least 97%, at least 99% or 100% identical to a sequence consisting of about amino acid 80-82 of SEQ ID NO:3 to an amino acid between about amino acid 143 and amino acid 183 of SEQ ID NO:3. The immunogenic peptide from helix A may be joined to the amino-terminal end of the HBcAg α4 helix sequence present in the coreC domain.

This disclosure provides a VLP comprising a fusion protein that comprises the amino acid sequence of a HBcAg, wherein the HBcAg loop of the fusion protein comprises an immunogenic peptide from helix A of the stem region of an influenza virus HA protein.

The c/e1 loop may consist of a sequence corresponding to about amino acid 72 to about amino acid 81 of a HBcAg from a wild-type HBV. The c/e1 loop may consist of a sequence corresponding to about amino acid 72 to about amino acid 81 of SEQ ID NO:3.

The immunogenic peptide may be inserted between the α3 helix sequence and the c/e1 loop sequence. The immunogenic peptide may be inserted between the c/e1 loop sequence and the α4 helix sequence. The immunogenic peptide may be inserted between the α3 helix sequence and the α4 helix sequence. The immunogenic peptide may be inserted between two amino acids within the c/e1 loop sequence. One or more amino acid residues may be replaced by the immunogenic peptide.

More than one immunogenic peptide may be inserted into the c/e1 loop sequence. The multiple immunogenic peptides may comprise the same epitope, or they can comprise different epitopes. In embodiments in which the multiple epitopes differ, the multiple epitopes can be from the same virus (e.g., influenza A), or they can be from different viruses (e.g., influenza A and influenza B). They can also be from different organisms (e.g., influenza A and a pneumococcal bacteria).

Multiple immunogenic peptides may be inserted into the c/e1 loop, and the immunogenic peptides may be inserted in tandem. Individual copies of the immunogenic peptide may be separated by a linker sequence.

Multiple immunogenic peptides may be inserted into the c/e1 loop, and each immunogenic peptide may be inserted at a different location in the c/e1 loop sequence. The immunogenic peptide may be joined directly to HBcAg amino acids. The immunogenic peptide may be joined to HBcAg amino acids using one or more linked sequences.

The fusion protein may comprise an amino acid sequence at least 50%, at least 90%, at least 95%, at least 97%, at least 99%, or 100% identical to a sequence selected from the group consisting of SEQ ID NOs:38-69. The fusion protein may consist of an amino acid sequence at least 50%, at least 90%, at least 95%, at least 97%, at least 99%, or 100% identical to a sequence selected from the group consisting of SEQ ID NOs:38-69. The fusion protein may comprise an amino acid sequence selected from the group consisting of SEQ ID NOs:38-69. The fusion protein may consist of a sequence selected from the group consisting of SEQ ID NOs:38-69.

Because VLPs of this disclosure can elicit an immune response to an influenza virus, they can be used as vaccines to protect individuals against infection by influenza virus. Thus, another aspect of this disclosure is a vaccine comprising a VLP of this disclosure. These vaccines may also contain other components such as adjuvants, buffers and the like. Although any adjuvant can be used, preferred adjuvants include chemical adjuvants such as aluminum phosphate, benzyalkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a method to elicit an immune response against influenza virus in an individual in need thereof or at risk of influenza infection, the method comprising administering a vaccine or VLP of this disclosure to the individual, such that an immune response against influenza virus is produced in the individual, wherein the VLP comprises one or more fusion proteins disclosed herein, and wherein the VLP displays an immunogenic peptide from helix A of an influenza virus HA stem region on its surface.

This disclosure provides a method to vaccinate an individual against influenza virus by administering a vaccine or VLP of this disclosure to an individual such that a protective immune response against influenza virus is produced in the individual, wherein the VLP comprises one or more fusion proteins disclosed herein, and wherein the VLP displays an immunogenic peptide from helix A of an influenza virus HA stem region on its surface.

Another method of this disclosure is a method to vaccinate an individual against infection with influenza virus by:
a) obtaining a vaccine comprising at least one VLP of this disclosure, wherein the VLP comprises one or more fusion proteins of this disclosure, and wherein the VLP displays the influenza HA on its surface; and,
b) administering the vaccine to an individual such that an immune response against an influenza virus is produced.

In these methods, the individual can be at risk for infection with influenza virus. The individual may have been exposed to influenza virus. As used herein, the terms exposed, exposure, and the like, indicate the subject has come in contact with a person or animal that is known to be infected with an influenza virus.

VLPs and vaccines of this disclosure may be administered using techniques well known to those in the art. Techniques for formulation and administration may be found, for example, in "Remington's Pharmaceutical Sciences", 18$^{th}$ ed., 1990, Mack Publishing Co., Easton, Pa. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the vaccines of this disclosure may be formulated in aqueous solutions, preferably in physiologically compatible buffers such as Hanks' solution, Ringer's solution, or physiological saline buffer.

Another aspect of the invention provides methods for producing antibodies that bind to influenza hemagglutinin protein, by immunizing a mammal with a vaccine of this disclosure to elicit an immunological response that generates antibodies to hemagglutinin; isolating mRNA molecules from antibody producing cells from the mammal; producing a phage display library displaying protein molecules encoded by the mRNA molecules; and isolating at least one phage from the phage display library. Thus, this disclosure also contemplates antibodies that specifically binds to influenza hemagglutinin protein that are induced following vaccination of a mammal with a vaccine construct of this disclosure. These antibodies may be polyclonal antibodies, monoclonal antibodies, bi-specific antibodies, and/or chimeric antibodies. These antibodies may bind influenza hemagglutinin protein with a binding affinity of below 20 nanomolar, and preferably of below 10 nanomolar. Methods for detecting, producing, and purifying such antibodies, and other tools for the production of these antibodies, are disclosed in WO 03/068201, WO 2004/084798, WO 01/72768, WO 03/070752, which are incorporated for herein for these purposes and in publications (Cohen et al., 2003a; Cohen et al., 2003b; Denkberg et al., 2003).

Also included in this disclosure are kits useful for practicing the disclosed methods. A kit may include nucleic acid molecules, proteins, or VLPs necessary for practicing this disclosure. These kits may also contain at least some of the reagents required to produce such nucleic acid molecules, proteins and/or VLPs. Such reagents may include, but are not limited to, isolated nucleic acid molecules, such as expression vectors, primers, sets of primers, or an array of primers.

The kit may also comprise instructions for using the kit, and various reagents, such as buffers, necessary to practice the methods of this disclosure. These reagents or buffers may be useful for producing or administering papilloma pseudovirus particles of this disclosure to a cell or an individual. The kit may also comprise any material necessary to practice the methods of this disclosure, such as syringes, tubes, swabs, and the like.

EXAMPLES

Example 1

Production of the Conserved Helix a Region of the HA2 Stem Fused with a Viral Capsid The HA2 region of HA has an alpha helix called helix A. It is part of the epitopes for a number of broadly neutralizing stem antibodies. However, some of the stem epitopes not only involve helix A, but also surrounding residues that may abrogate stem antibody binding by acquiring glycosylation sites and antibody escape mutations. Thus, the inventors sought to determine whether a smaller epitope footprint specific to helix A might be advantageous. To do so, they constructed the conserved helix A region of the HA2 stem fused with a viral capsid and tested the ability of this fusion protein to elicit antibodies to hemagglutinin. They designed a novel nanoparticle based on the insertion of helix A of H1 HA into a surface loop of the icosahedral hepatitis B virus capsid protein to assess whether a helix-A capsid nanoparticle could be produced and purified, and whether the helix-A nanoparticle would be immunogenic and induce antibodies that bound hemagglutinin, and whether immunization with the helix-A be protective in an influenza virus lethal challenge mouse model.

As depicted in FIGS. 1A-1E, the inventors first designed a novel protein construct consisting of the conserved helix A from the stem region of H1 HA inserted into a surface loop region for hepatitis B virus capsid. FIG. 1A shows the structure of influenza HA in complex with scFv from a broadly neutralizing antibody F10 that targets the stem region (PDBID 3FKU). The HA1 head region at the top (shown in medium gray with HA2 stem region in darker gray; the arrow points to helix A within the stem region; the antibody scFv (Ab) is colored in light grey). FIG. 1B shows a hepatitis B virus capsid dimer indicating the alpha helical fold of the protein (the immunodominant loop at the tip of the dimeric spike is denoted by an arrow; the loop area is also referred to the c1 epitope). FIG. 1C shows the structure of the hepatitis B virus capsid (PDBID 1QGT) with T=4 icosahedral symmetry with 240 subunits of the capsid dimer (the capsid is shown at a reduced scale; scale bar, 10 nm). FIG. 1D is a schematic of the capsid protein monomer. FIG. 1E is a schematic of the fusion protein design consisting of a capsid monomer with two copies of helix A (light grey) inserted into the tip of the loop of the capsid protein (dark grey). Alpha helices are schematically shown as rectangles with the base as an oval. Loops are between capsid and influenza sequences.

The expression constructs designed by the inventors are depicted in FIGS. 2A-2D. FIG. 2A depicts the capsid scaffold without epitope insertions. FIG. 2B depicts the nanoparticle stem 01 construct (NP st01) consisting of copies of helix A of influenza hemagglutinin inserted into the capsid at the immunodominant loop region. FIG. 2C depicts the nanoparticle stem 02 construct (NP st02) consisting of copies of helix A of influenza hemagglutinin inserted into the capsid at the immunodominant loop region. FIG. 2D is the diagram key to indicate the schematic representations for each region: capsid, detection epitope tag, epitope insertion site (immunodominant loop), helix-A, and flanking linkers).

Figure 3B:
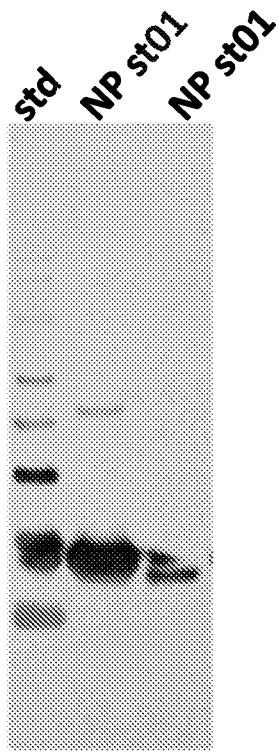
Figure 3C:
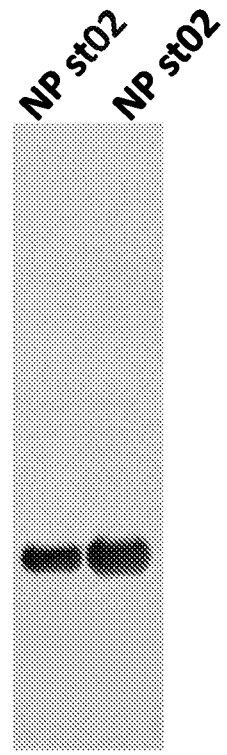

Protein expression from these expression constructs was detected by immunoblotting (western blotting) (FIGS. 3A-3C). Samples were denatured by SDS-PAGE under reducing conditions and then transferred to nitrocellulose membrane. Primary antibody was mAb 10E11 that recognizes residues 1-10 at the N-terminus of the capsid region. The secondary antibody used for detection was anti-mouse antibody conjugated to alkaline-phosphate and chromogenic development was used to visualize bands. For each construct two independent preparations of crude lysates of bacteria from expression cultures were tested. FIG. 3A shows an immunoblot of capsid expression (as positive-control) with a band at about 20 kilodaltons (kDa). FIG. 3B shows an immunoblot of nanoparticle stem 01 construct (NP st01) with a band at about 25 kilodaltons (kDa). FIG. 3C shows an immunoblot of nanoparticle stem 02 construct (NP st02) with a band at about 25 kilodaltons (kDa).

Figure 4A:
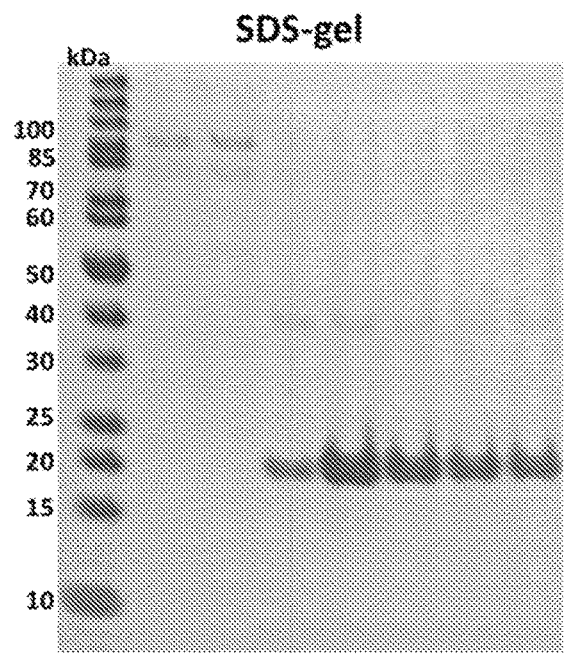
FIGS. 4A and 4B depict the purification and particle formation of capsid proteins.
Figure 4B:
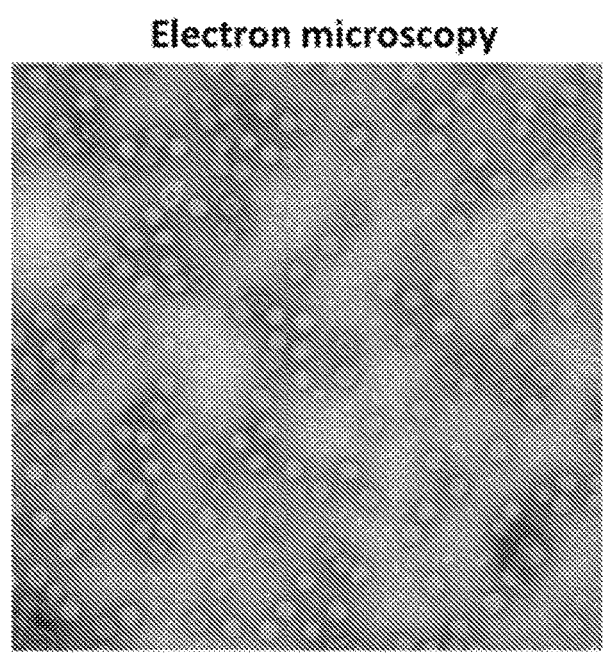

These expression constructs were used to form purified proteins, which formed capsids that were visualized by electron microscopy of capsid samples. FIG. 4A shows an SDS-PAGE gel analysis of purified capsid protein detected in different purification fractions, and FIG. 4B is an electron micrograph of capsid samples, in which capsids appear a round particles.

Figure 5A:
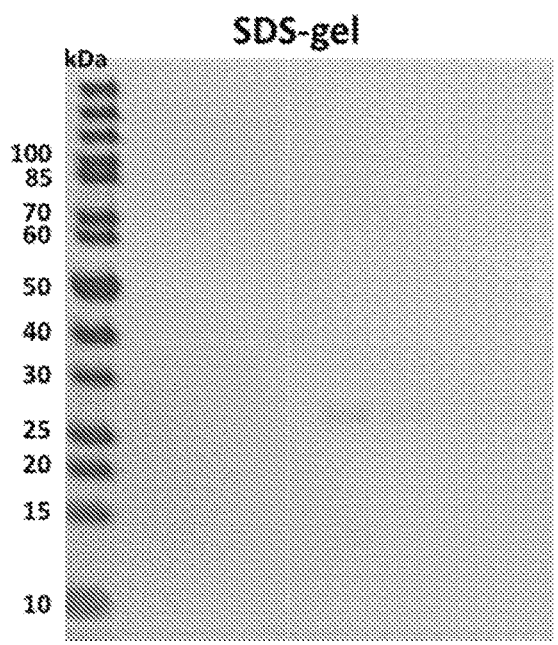
FIGS. 5A and 5B depict the purification and particle formation of nanoparticle stem 01 construct (NP st01).
Figure 5B:
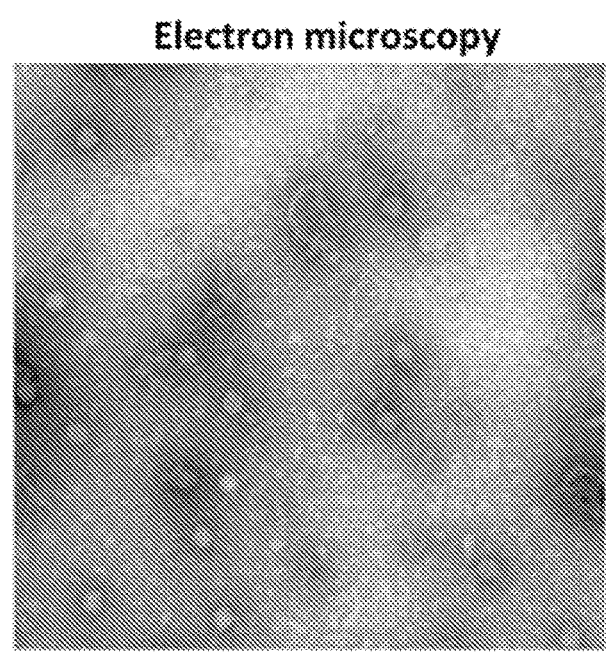

Similarly, FIG. 5A shows an SDS-gel analysis of purified NP st01 protein detected in different purification fractions, and FIG. 5B shows an electron microscopy of NP st01 samples, in which some nanoparticles appear as round particles. FIG. 6A shows an SDS-PAGE gel analysis of purified NP st02 protein detected in different purification fractions, and FIG. 6B shows an electron micrograph of NP st02 samples, in which nanoparticles appear as round particles.

This Example demonstrates that the inventors devised scale-up expression, purification, and endotoxin removal procedures for the preparation of this Helix-A nanoparticle for animal studies. This system can yield up to 10 mg/ml of protein per one liter of culture. Advantageously, this system can produce large amounts of particles easily and quickly without the need for eggs or large cell cultures, if a pandemic were to occur.

Example 2

Comparative Reactivity of Nanoparticles with Antibodies

The inventors tested the reactivity of the isolated nanoparticles described in Example 1 by dob-blot analysis. The cross-reactivity of the nanoparticles containing the capsid, NPst01, and NPst02 antigens (at decreasing concentrations from 1.0 to 0.003 micrograms) was tested with polyclonal rabbit antibodies to influenza H1 hemagglutinin protein. The primary antibody was a rabbit polyclonal (H1 pAb) that was raised against full-length H1 hemagglutinin. The secondary antibody (for detection) was anti-mouse antibody conjugated to alkaline-phosphate. The NP st01 construct showed low levels of reactivity while the NP st-02 construct showed relatively stronger reactivity to H1 polyclonal antibodies (FIG. 7).

The insertion of the foreign epitope into the capsid loop was verified by probing with the anti-loop monoclonal antibody 88 (mAb88). Dob-blot analysis was used to compare the reactivity of capsid versus the nanoparticle stem 02 construct (NP st02) probed with mAb88 that specifically recognizes the immunodominant loop (c1 epitope) of the capsid. Antigens were capsid and NPst02 preparations at decreasing concentrations, and hemagglutinin (HA) H1 was used as a negative control. FIG. 8 shows that the immunodominant epitope for mAb was maintained in the capsid, but foreign stem epitope insertion abrogates the binding of antibody to capsid for the NPst02 nanoparticle.

Example 3

NP st02 Nanoparticle Elicits Antibodies to Hemagglutinin

To test the ability of the nanoparticle constructs to elicit a broadly protective immune response, mice were immunized with the stem 02 (NP st02) nanoparticle and then challenged with the 2009 pandemic H1N1 influenza virus. FIG. 9 shows the immunization and challenge schedule for the mice. The immunological challenge was conducted with the pandemic influenza virus (A/California/07/09) H1N1.

The immunogenicity of the NP st02 nanoparticle was assessed by ELISA. FIG. 10A shows the antibody levels of sera of immunized mice analyzed by ELISA for reactivity to the nanoparticle (NP st02) and cross-reactivity with influenza H1 hemagglutinin (HA) protein at Day 14 with one intramuscular (IM) injection. FIG. 10B shows similar analysis of mice sera at Day 35 after two intramuscular (2IM) injections. There were three groups of sera tested consisting of PBS (saline, black bar), NP st-02 without adjuvant (white bar) and NP st-02 plus adjuvant (Ribi) (grey bar).

Survival curves were prepared to compare the protective efficacy of the nanoparticle constructs in the challenged mice. FIG. 11A shows a comparison of survival curves of mice challenged with 10 MLD50 (mouse lethal dose) of H1N1 virus at day 42 after two intramuscular inoculations at days 0 and 21 with nanoparticle NP-st02 without addition of Ribi adjuvant (panel A, dotted line) compared with a PBS control (FIG. 11A, solid line). FIG. 11B shows a comparison of survival curves of mice challenged with 10 MLD50 (mouse lethal dose) of H1N1 virus at day 42 after two intramuscular inoculations at days 0 and 21 with nanoparticle NP-st02 with the addition of Ribi adjuvant (panel B, dotted line) compared with a PBS control (panel B, solid line). Surprisingly, these data showed that nanoparticle without adjuvant appeared more efficacious than nanoparticle formulated with adjuvant.

Figure 12A:
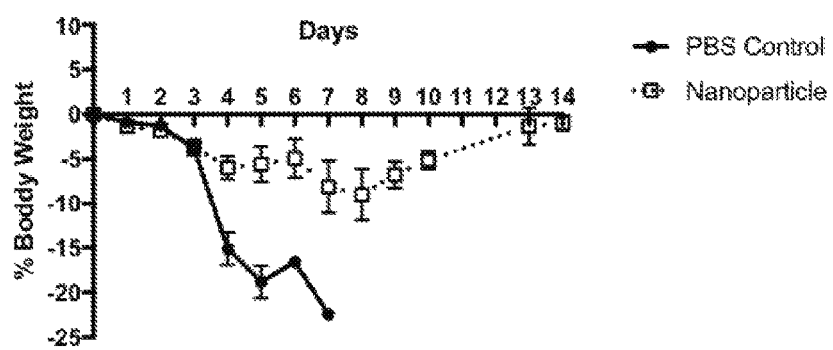
Figure 12B:
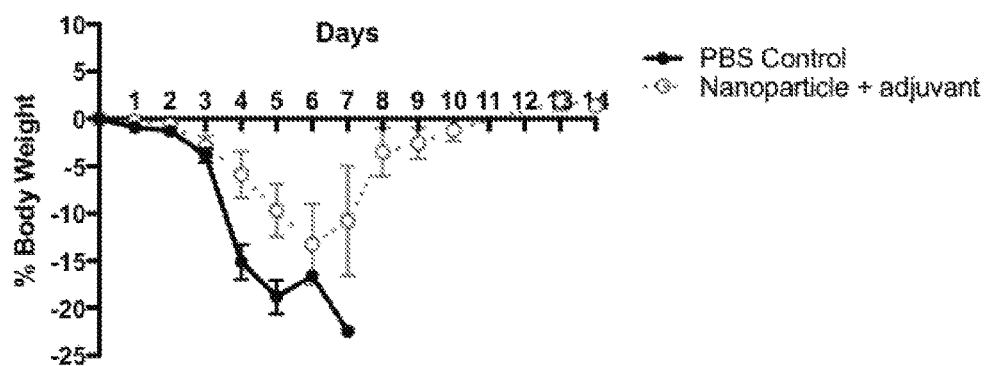

Similarly, weight loss in the challenged mice was monitored as a measure of protection following challenge with the pandemic influenza virus. FIG. 12A shows a comparison of weight-loss curves of challenged mice immunized with nanoparticle NP-st02 without Ribi adjuvant (panel A, dotted line with squares) compared to PBS control (panel A, solid black line). FIG. 12B shows a comparison of weight-loss curves of challenged mice immunized with nanoparticle NP-st02 with Ribi adjuvant (panel B, dotted line with circles) compared to PBS control (panel B, solid black line). Once again, the nanoparticle immunization without Ribi adjuvant appeared more efficacious in reducing weight-loss associated with infection.

Example 4

Stability and Immunogenicity of Nanoparticle (NP-st02)

Figure 13D:
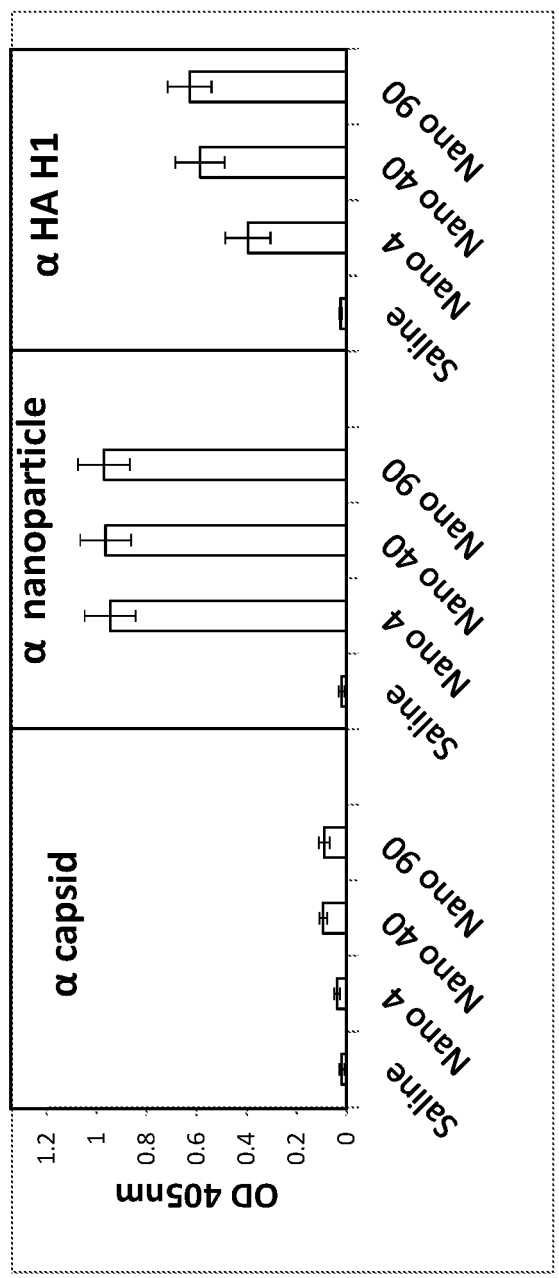
Figure 15A:
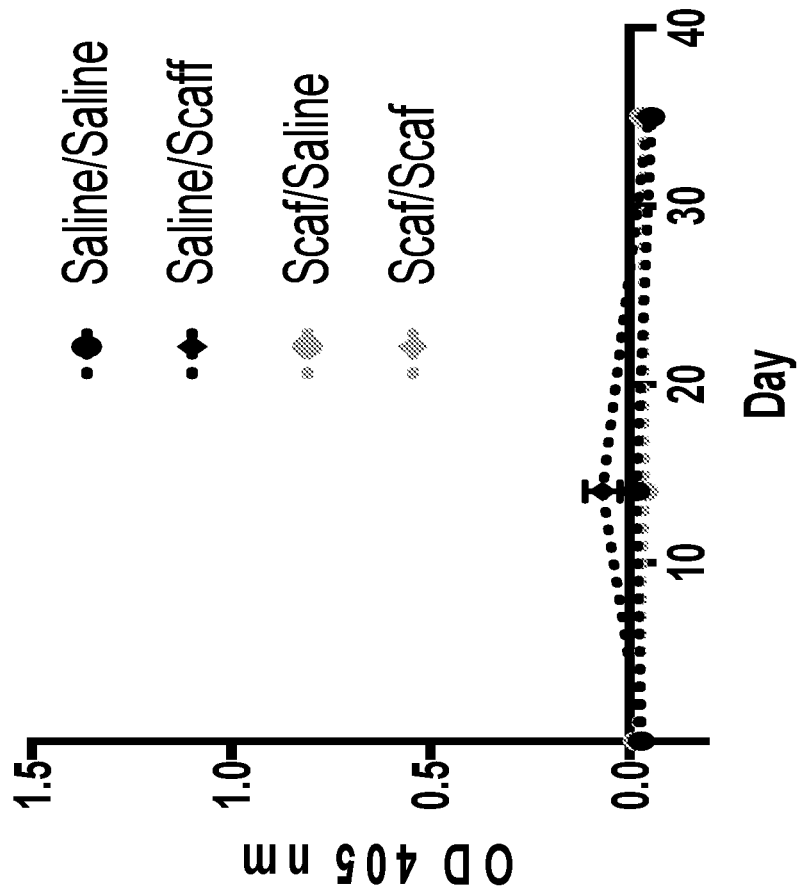
Figure 15B:
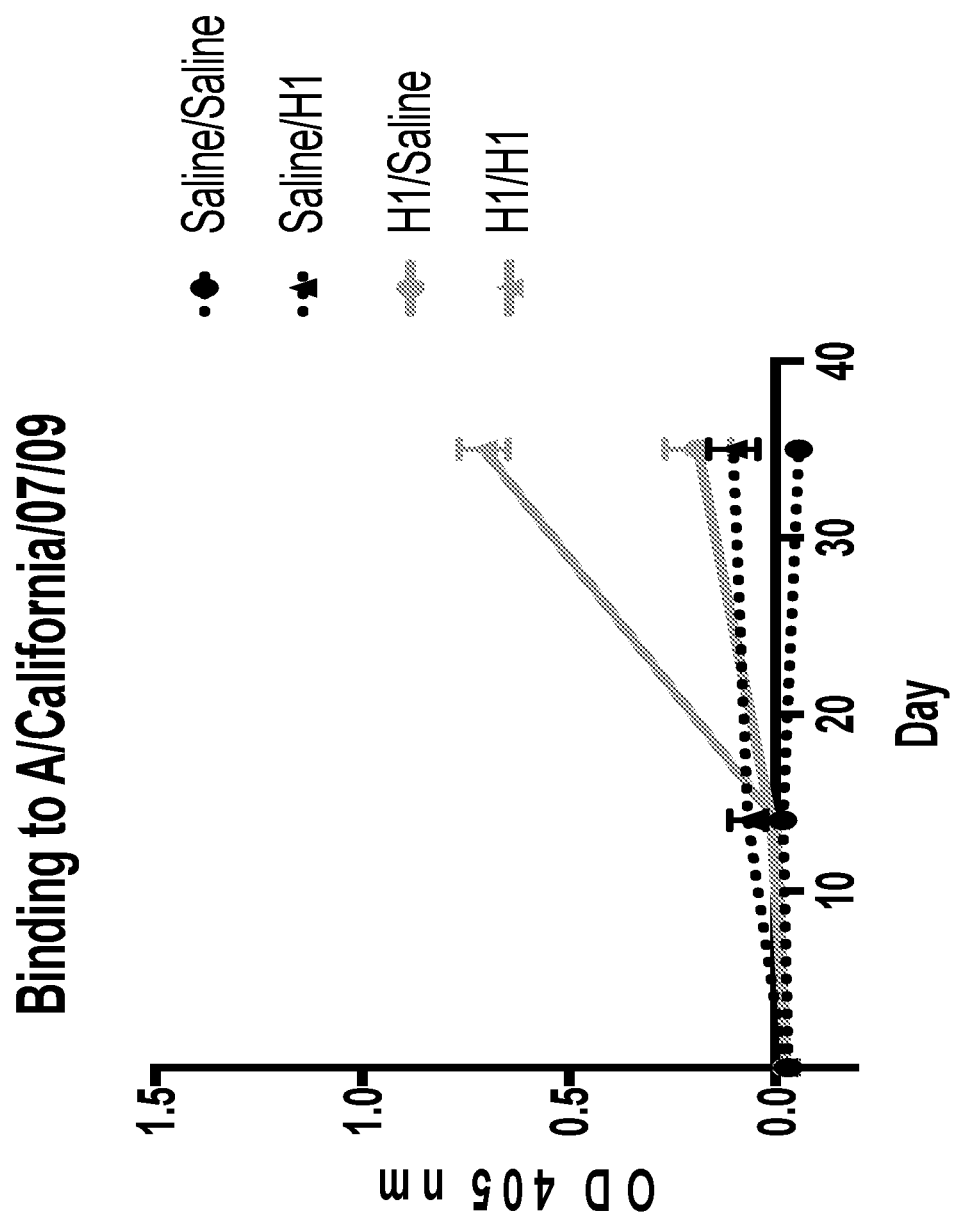
Figure 15C:
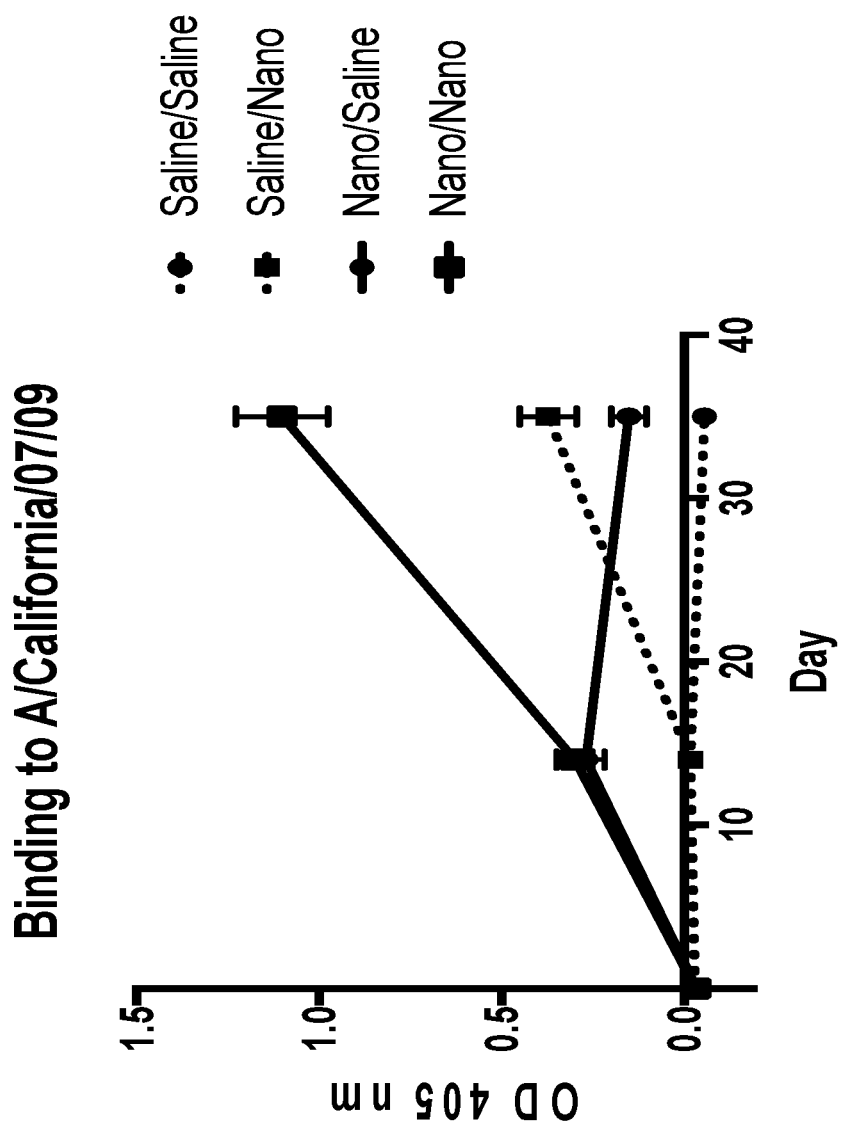
Figure 15D:
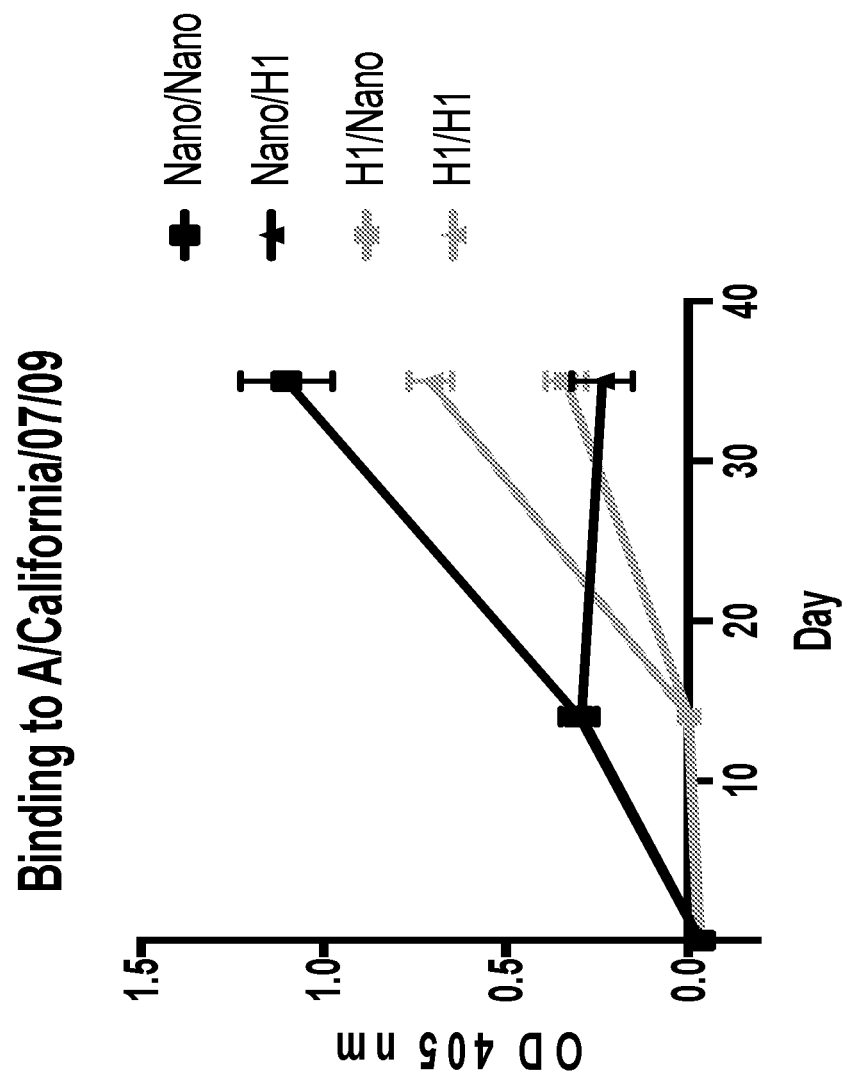
Figures 16A, 16B, 16C:
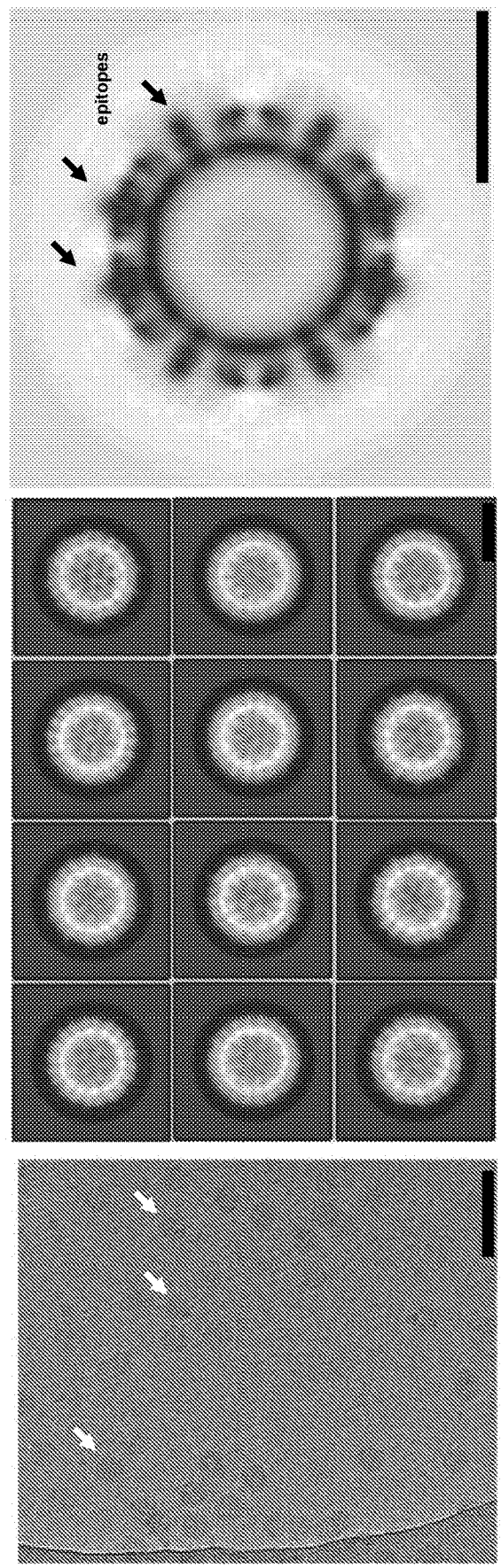
Figure 16E:
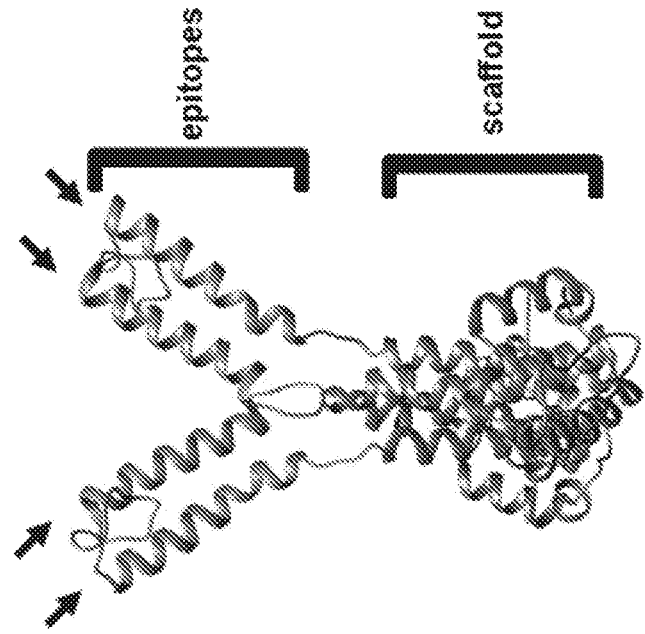
Figure 16D:
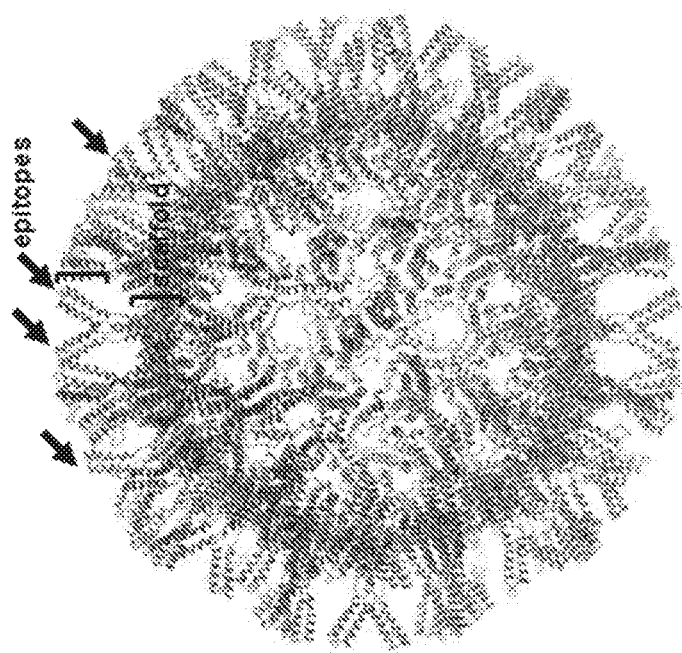
Figure 17D:
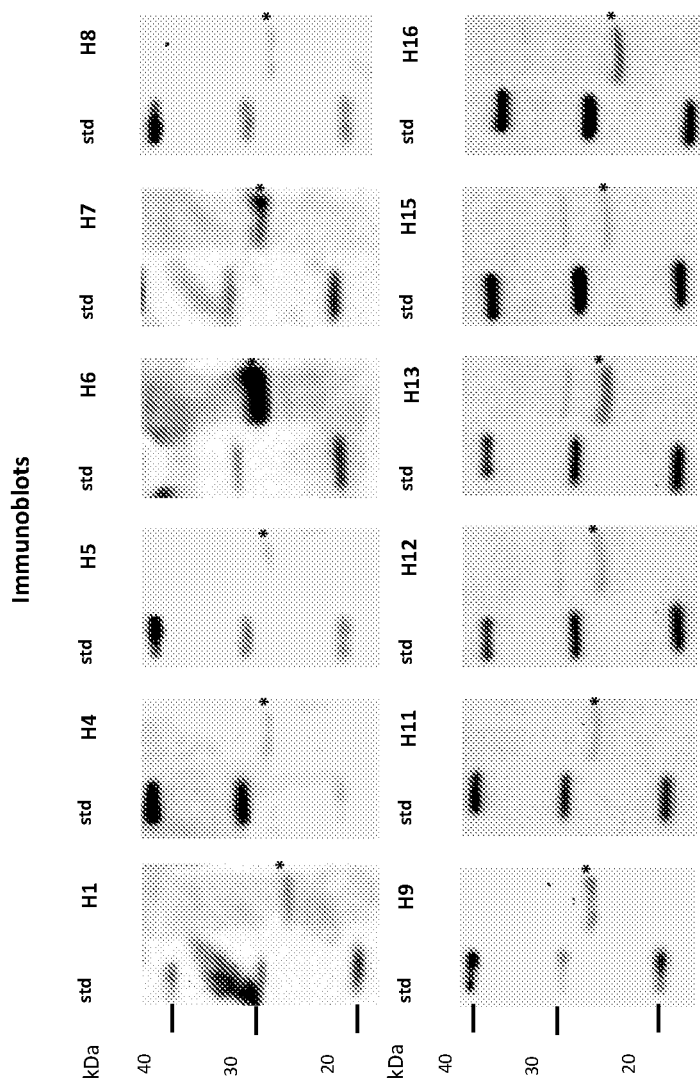
FIG. 17D shows expression of HA-nanoparticle fusion proteins from different HA subtypes from the nanoparticle library as indicated by immunoblotting. The proteins would have a molecular weight close to 25 kilodaltons. Asterisks denote bands for the nanoparticle proteins. Standards are std. Each hemagglutinin (HA) subtype is denoted as H1, H4, etc. The library displays greater than 90% sequence identity for greater than 96% coverage of stem epitopes from greater than 36,0000 HA sequences (H1 to H16). Nanoparticles with stem regions from different HA subtypes from both group 1 and group 2 influenza viruses can be expressed.
Figure 18D:
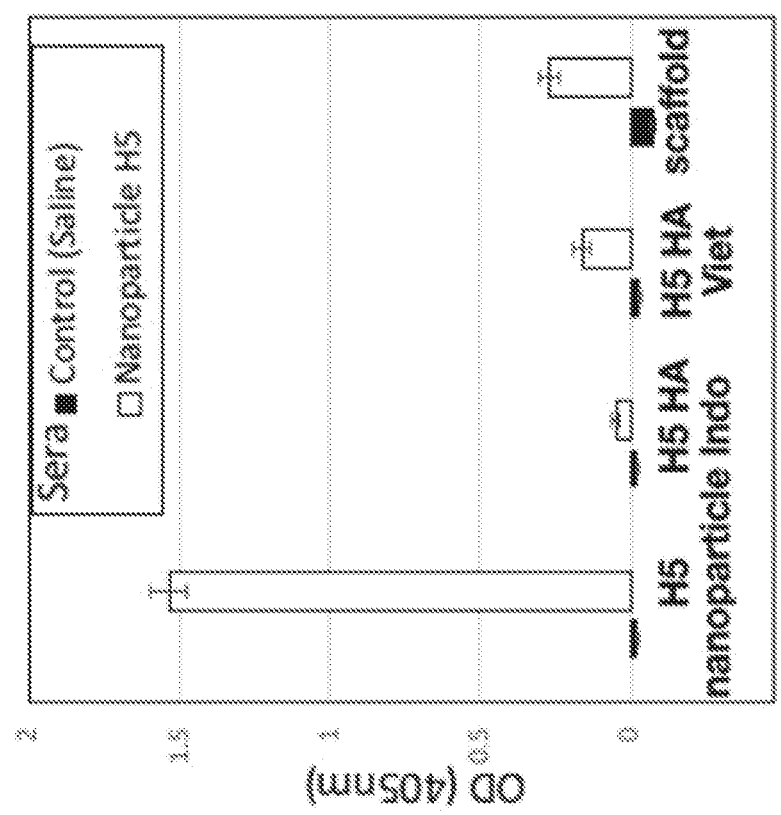
Figure 18E:
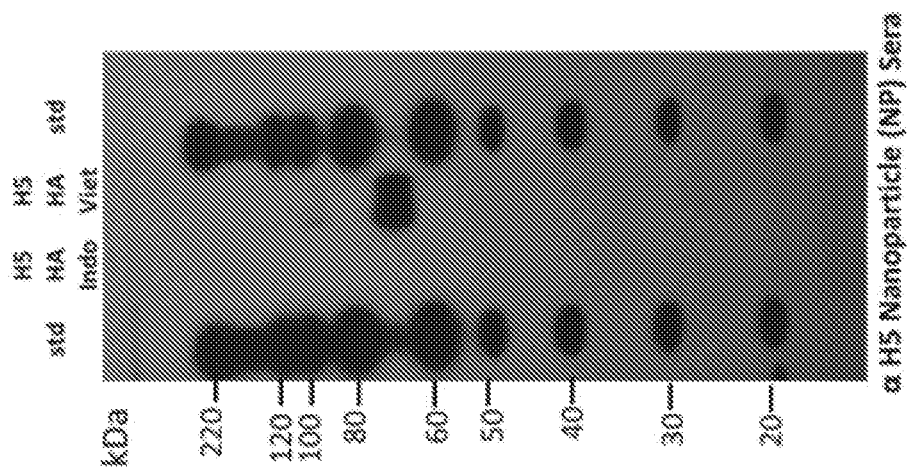
Figure 19E:
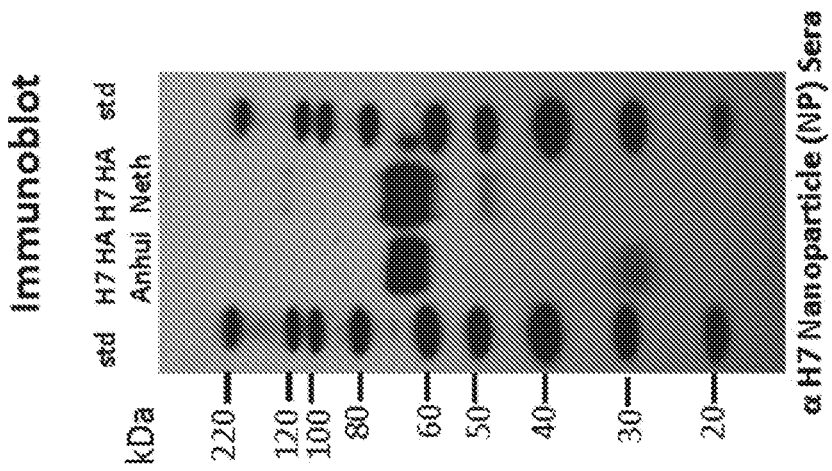
Figure 19D:
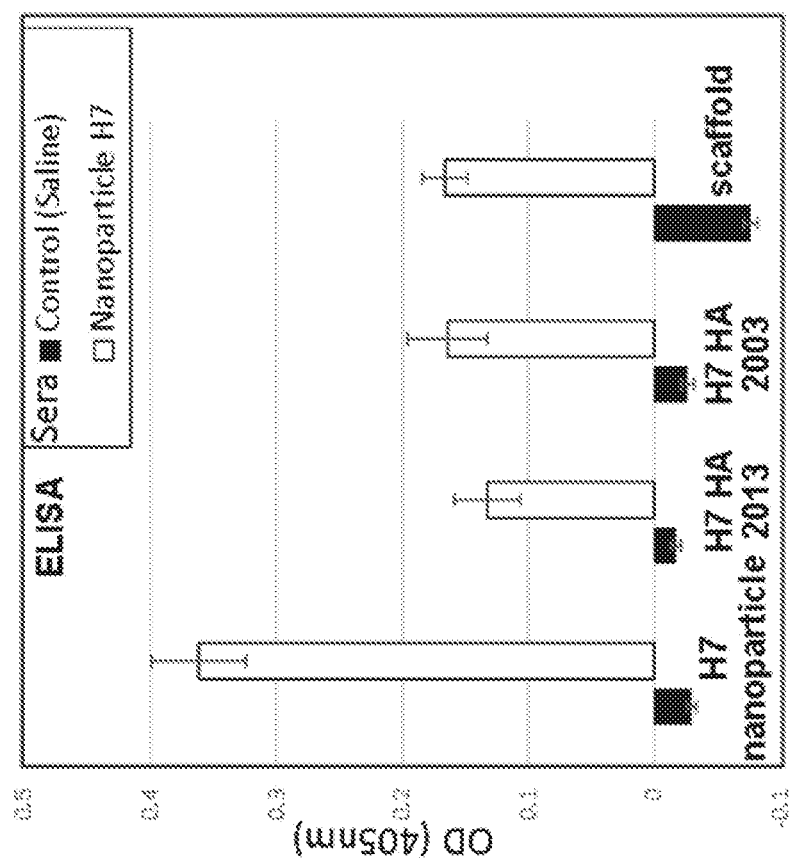
Figure 20B:
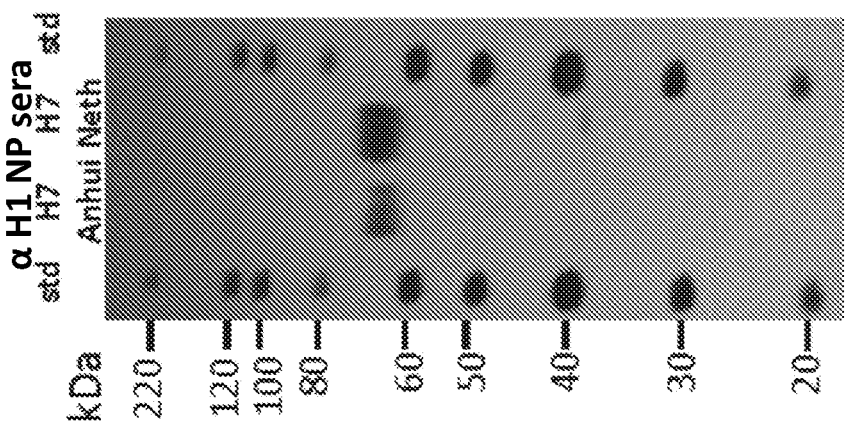
Figure 20A:
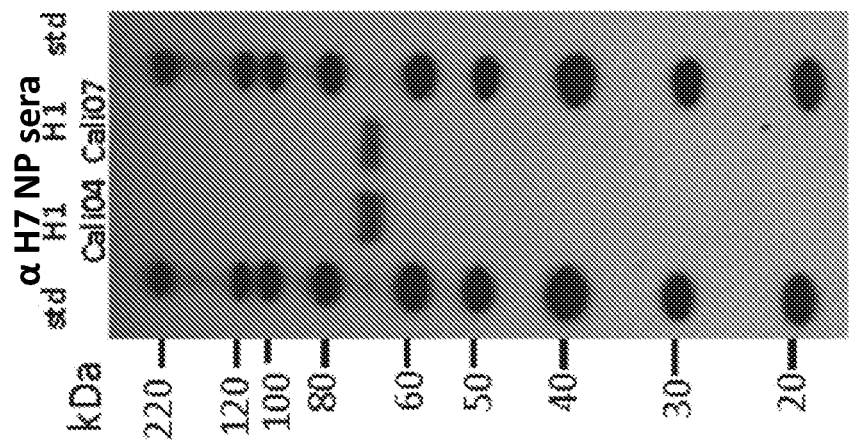
Figure 20D:
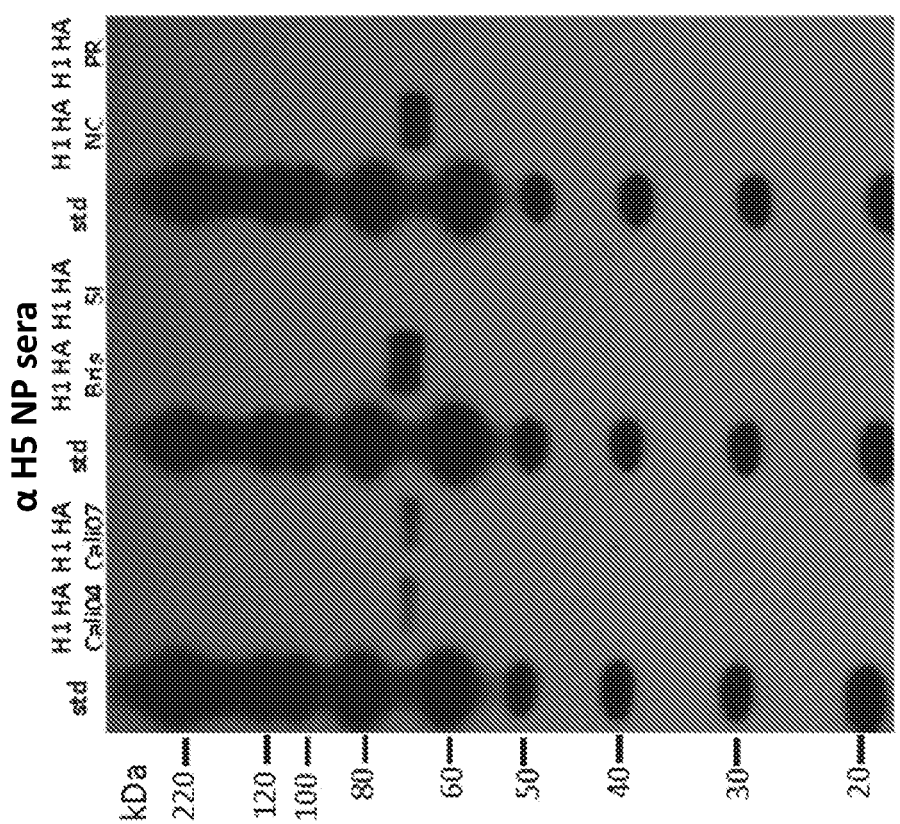
Figure 21A:
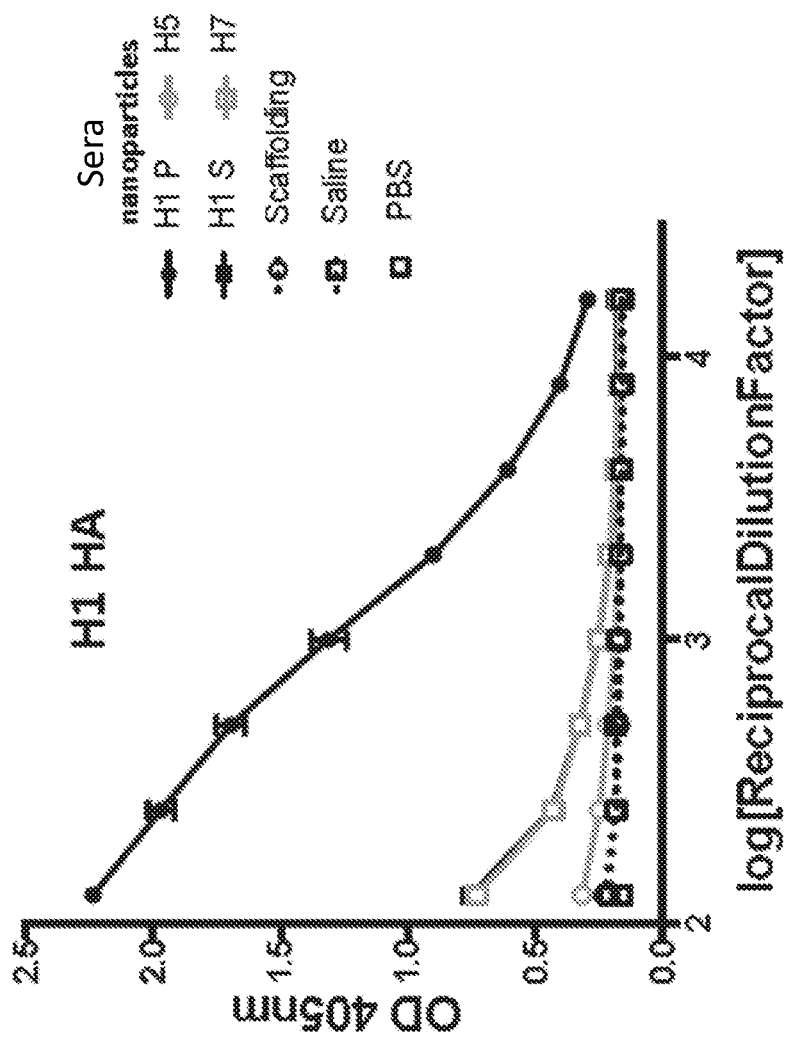
FIGS. 21A-21C show the results of using recombinant HA proteins and nanoparticle sera to assess the presence and relative levels of homosubtypic and heterosubtypic HA binding antibodies.
Figure 21B:
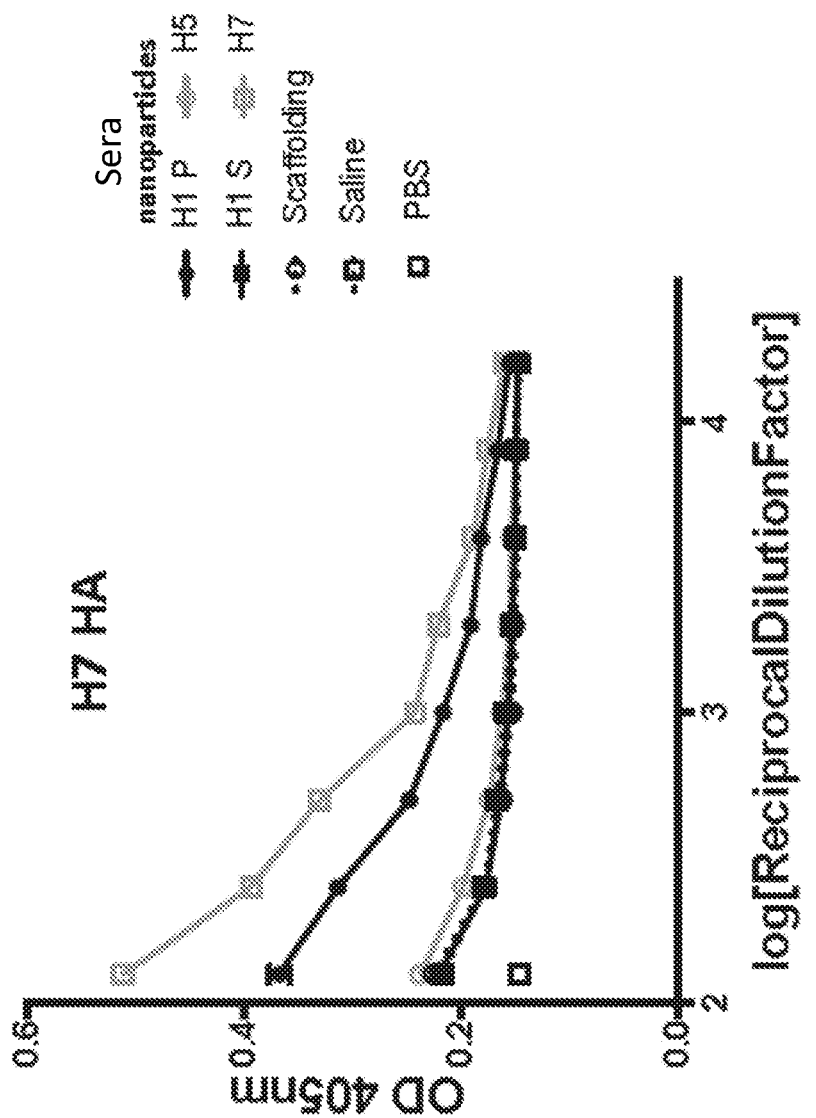
Figure 21C:
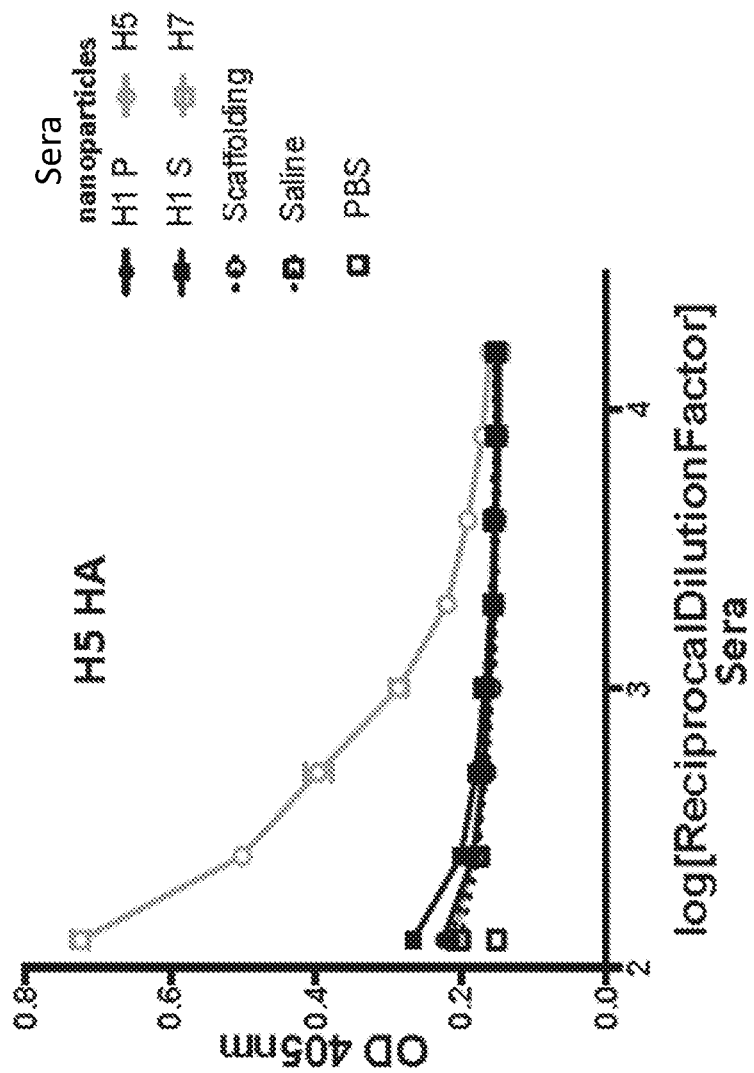

The stability of the nanoparticles was tested by subjecting the immunogenic VLP particles to different low and high temperatures before returning the particles to room temperature and conducing mouse immunogenicity studies. FIGS. 13A, 13B, and 13C show electron micrographs of negatively-stained of nanoparticles incubated at 4° C. (FIG. 13A), 40° C. (FIG. 13B), and 90° C. (FIG. 13C), for 30 minutes then returned to room temperature. For the immunization studies, the nanoparticles were equilibrated to 25° C. before being used to immunize mice. FIG. 13D shows the antibody levels in sera of immunized mice analyzed by ELISA for reactivity to capsid, nanoparticle (Nano) and influenza H1 hemagglutinin (HA) protein at day 35 after two intramuscular injections of the nanoparticles. There were four groups of sera tested consisting of PBS (saline) and nanoparticle NP st-02 exposed to the three temperatures: 4, 40, and 90 degrees Celsius (Nano 4, 40, 90).

These data demonstrate that these NP-st02 nanoparticle remains intact and immunogenic after exposure to variable temperatures, and elicits anti-hemagglutinin antibodies in mammals immunized with these nanoparticles.

Example 5

Bioinformatic Analysis of the Conservation and Sequence Variation of the Helix a Region Between Influenza Hemagglutinins Hemagglutinin sequences (n=50,426) (H1 to H16) from the influenza sequence database were analyzed by separating into H1 to H16 HA subtypes and extracting the helix A region for each sequence. A consensus sequence for helix A for each HA subtype was derived. Pair-wise sequence identity comparisons between different HA subtypes (H1-H16) were then performed and organized as a matrix (FIG. 14). The comparative data shows that the identities ranged from 50% to 100% for comparison between two different subtypes.

Example 6

Immunogenicity Study Using the Stem 02 (NP-St02) Nanoparticle for Prime and/or Prime/Boost Balb/c mice (n=5 per group) were used to test the ability of nanoparticles of the invention to elicit an immune response in a prime/boost immunization protocol. To prime the mice, each mouse was injected with either saline, scaffold alone (Scaf), HA protein from A/California/07/09 H1 (H1), or NP-st02. 21 days later, each mouse was then boosted by injection with either saline, scaffold alone (Scaf), A/California/07/09 H1 HA protein, or NP-st02. 50 ug of immunogen was given at each injection. Blood samples ere collected at days 0, 14, and 35, and the sera analyzed by ELISA for levels of anti-A/California/07/09 H1 HA protein antibody. The results of this analysis, which are shown in FIGS. 15A-D, indicate that the highest levels of antibody to the H1 HA protein resulted from using the H1-nanoparticle as both the prime and boost immunogen.

Example 7

Structural Analysis of H1-Nanoparticle (NPst02) by Cryo-Electron Microscopy and Molecular Modeling Purified H1-nanoparticles were analyzed by cryo-electron microscopy. Based on the electron micrographs, a 3-dimensional reconstruction of the nanoparticle was produced. The results of this analysis are illustrated in FIG. 16A-16E.

Example 8

Expression, Purification, and Immunogenicity of H5-Nanoparticle

H5-nanoparticles were produced according to the present disclosure, and the purified nanoparticles analyzed by SDS-PAGE analysis, and electron microscopy. The particles were also analyzed for their ability to elicit antibodies in mice that bind H5-nanoparticles, H5 HA protein. The results of these analyses are shown in in FIGS. 18A-18E. The results show that nanoparticles carrying the H5 HA stem region could be purified, were immumogenic, and could elicit antibodies that bound H5-nanoparticles and recombinant H5 HA protein.

Example 9

Expression, Purification, and Immunogenicity of H7-Nanoparticle

H7-nanoparticles were produced according to the present disclosure, and the purified nanoparticles analyzed by SDS-PAGE analysis, and electron microscopy. The particles were also analyzed for their ability to elicit antibodies in mice that bind H7-nanoparticles, H7 HA protein. The results of these analyses are shown in in FIGS. 18A-E. The results show that nanoparticles carrying the H7 HA stem region could be purified, were immunogenic, and could elicit antibodies that bound H7-nanoparticles and recombinant H7 HA protein.

Example 10

Study of the Ability of Recombinant HA Proteins and Nanoparticle Sera to Probe for Homosubtypic and Heterosubtypic Binding of Antibodies Mice were immunized with either H7-nanoparticles, H5-nanoparticles, or H1 nanoparticles. Sera was collected and tested for the presence of antibodies to H7 or H1 nanoparticles or H1 or H7 recombinant HA proteins. The results, which are shown in FIGS. 20A-E, indicate that nanoparticles containing HA system epitopes, and prepared according to the present disclosure, can elicit both homosubtypic and heterosubtypic antibodies to influenza hemagglutinin protein.

Example 11

Using Recombinant HA Proteins and Nanoparticle Sera to Assess the Presence and Relative Levels of Homosubtypic and Heterosubtypic HA Binding Antibodies Mice were immunized with nanoparticles containing HA protein from various Types of influenza virus. Sera was collected and tested for the presence of antibodies to H1, H5 or H7 recombinant HA proteins. The results, which are shown in FIGS. 21A-D, indicate that nanoparticles containing HA system epitopes, and prepared according to the present disclosure, can elicit both homosubtypic and heterosubtypic binding antibodies to influenza hemagglutinin protein.

The foregoing examples of the present invention have been presented for purposes of illustration and description. These examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

What is claimed:

1. A fusion protein comprising:
   a first fusion protein comprising an immunogenic peptide from helix A from the stem region of an influenza hemagglutinin (HA) protein joined to the carboxyl-terminal end of the α3 helix from a hepatitis B core antigen (HBcAg); and/or,
   a second fusion protein comprising an immunogenic peptide from helix A from the stem region of an influenza HA protein joined to the amino-terminal end of the α4 helix from a hepatitis B core antigen (HBcAg).

2. The fusion protein of claim 1, wherein the first fusion protein forms a virus-like particle (VLP) when combined with a HAcAg-C protein, and/or wherein the second fusion protein forms a VLP when combined with a HAcAG-N protein.

3. The fusion protein of claim 1, wherein the immunogenic peptide of the first fusion protein is joined to the carboxyl-terminal end of a HBcAg coreN domain.

4. The fusion protein of claim 1, wherein the immunogenic peptide of the second fusion protein is joined to the amino-terminal end of a HBcAg core C domain.

5. The fusion protein of claim 1, wherein one end of the immunogenic peptide is joined to the carboxyl-terminal end of the HBcAg α3 helix, wherein the other end of the immunogenic peptide is joined to the amino-terminal end of the HBcAg α4 helix, and wherein the fusion protein forms a VLP that displays the influenza HA helix A on its surface.

6. The fusion protein of claim 1, wherein the fusion protein comprises:
   a) the immunogenic peptide from helix A from the stem region of an influenza HA protein;
   b) a first amino acid sequence comprising at least 30, at least 40, at least 50, or at least 60 contiguous amino residues from the polypeptide sequence immediately upstream of the HBcAg c/e1 loop sequence, wherein the first amino acid sequence comprises an HBcAg α3 helix sequence; and,
   c) a second amino acid sequence comprising at least 50, at least 60, or at least 70 contiguous amino acid residues from the polypeptide sequence immediately downstream of the HBcAg c/e1 loop sequence, wherein the second amino acid sequence comprises an HBcAg α4 helix sequence;
   wherein one end of the immunogenic peptide is joined to the carboxy-terminal end of the first amino acid sequence, and the other end of the immunogenic peptide is joined to the amino-terminal end of the second amino acid sequence; and, the fusion protein self-assembles into a VLP that displays the influenza HA helix A on its surface.

7. The fusion protein of claim 1, wherein the fusion protein comprises:
   the immunogenic peptide from helix A in the stem region of an influenza HA protein;
   a HBcAg coreN domain; and,
   a HBcAg coreC domain;
   wherein
   one end of the immunogenic peptide is joined to the carboxy-terminal end of the coreN domain;
   the other end of the immunogenic peptide is joined to the amino-terminal end of the coreC domain; and,
   the fusion protein self-assembles into a VLP that displays the influenza HA helix A on its surface.

8. The fusion protein of claim 1, wherein the fusion protein comprises the amino acid sequence of a HBcAg, and wherein at least one immunogenic peptide from helix A from the stem region of an influenza HA protein is inserted into, or replaces, the c/e1 loop.

9. A kit comprising the fusion protein of claim 1.

10. A virus like particle (VLP) or nanoparticle comprising the fusion protein of claim 1.

11. A vaccine composition comprising the VLP or nanoparticle of claim 10.

12. A method of eliciting an immune response against influenza virus in an individual, comprising administering to the individual the VLP or nanoparticle of claim 10.

13. A nucleic acid molecule encoding a fusion protein comprising:
   a first fusion protein comprising an immunogenic peptide from helix A from the stem region of an influenza hemagglutinin (HA) protein, joined to the carboxyl-terminal end of the α3 helix from a hepatitis B core antigen (HBcAg); and/or,
   a second fusion protein comprising an immunogenic peptide from helix A from the stem region of an influenza HA protein, joined to the amino-terminal end of the α4 helix from a hepatitis B core antigen (HBcAg).

14. The nucleic acid molecule of claim 13, wherein the first fusion protein forms a virus-like particle (VLP) when combined with a HAcAg-C protein, and/or wherein the second fusion protein forms a VLP when combined with a HAcAG-N protein.

15. The nucleic acid molecule of claim 13, wherein the immunogenic peptide of the first fusion protein is joined to the carboxyl-terminal end of a HBcAg coreN domain.

16. The nucleic acid molecule of claim 13, wherein the immunogenic peptide of the second fusion protein is joined to the amino-terminal end of a HBcAg core C domain.

17. The nucleic acid molecule of claim 13, wherein one end of the immunogenic peptide is joined to the carboxyl-terminal end of the HBcAg α3 helix, wherein the other end of the immunogenic peptide is joined to the amino-terminal end of the HBcAg α4 helix, and wherein the fusion protein forms a VLP that displays the influenza HA helix A on its surface.

18. The nucleic acid molecule of claim 13, wherein the fusion protein comprises:
   a) the immunogenic peptide from helix A in the stem region of an influenza HA protein;
   b) a first amino acid sequence comprising at least 30, at least 40, at least 50, or at least 60 contiguous amino residues from the polypeptide sequence immediately upstream of the HBcAg c/e1 loop sequence, wherein the first amino acid sequence comprises an HBcAg α3 helix sequence; and,
   c) a second amino acid sequence comprising at least 50, at least 60, or at least 70 contiguous amino acid residues from the polypeptide sequence immediately downstream of the HBcAg c/e1 loop sequence, wherein the second amino acid sequence comprises an HBcAg α4 helix sequence;
   wherein one end of the immunogenic peptide is joined to the carboxy-terminal end of the first amino acid sequence, and the other end of the immunogenic peptide is joined to the amino-terminal end of the second amino acid sequence; and, the fusion protein self-assembles into a VLP that displays the influenza HA helix A on its surface.

19. The nucleic acid molecule of claim 13, wherein the fusion protein comprises:
   the immunogenic peptide from helix A in the stem region of an influenza hemagglutinin (HA) protein;
   a HBcAg coreN domain; and,
   a HBcAg coreC domain;
   wherein
   one end of the immunogenic peptide is joined to the carboxy-terminal end of the coreN domain;
   the other end of the immunogenic peptide is joined to the amino-terminal end of the coreC domain; and,
   the fusion protein self-assembles into a VLP that displays the influenza HA helix A on its surface.

20. The nucleic acid molecule of claim 13, wherein the fusion protein comprises the amino acid sequence of a HBcAg, and wherein at least one immunogenic peptide from helix A from the stem region of an influenza HA protein is inserted into, or replaces, the c/e1 loop.

21. The fusion protein of claim 8, wherein two immunogenic peptides from helix A from the stem region of an influenza HA protein are inserted into, or replace, the c/e1 loop.

22. The fusion protein of claim 1, wherein the immunogenic peptide comprises or consists of an amino acid sequence set forth as any one of SEQ ID NOs: 70-99.

23. The fusion protein of claim 1, wherein the fusion protein comprises or consists of an amino acid sequence set forth as any one of SEQ ID NOs: 38-69.

* * * * *

SEQUENCE LISTING

```
<160> NUMBER OF SEQ ID NOS: 99

<210> SEQ ID NO 1
<211> LENGTH: 566
<212> TYPE: PRT
<213> ORGANISM: Influenza Virus
<220> FEATURE:
<221> NAME/KEY: misc_feature
<222> LOCATION: (239)..(240)
<223> OTHER INFORMATION: Xaa can be any naturally occurring amino acid

<400> SEQUENCE: 1

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95
```

```
Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
            165                 170                 175

Lys Leu Ser Lys Ser Tyr Ile Asn Asp Lys Gly Lys Glu Val Leu Val
        180                 185                 190

Leu Trp Gly Ile His His Pro Ser Thr Ser Ala Asp Gln Gln Ser Leu
    195                 200                 205

Tyr Gln Asn Ala Asp Ala Tyr Val Phe Val Gly Ser Ser Arg Tyr Ser
210                 215                 220

Lys Lys Phe Lys Pro Glu Ile Ala Ile Arg Pro Lys Val Arg Xaa Xaa
225                 230                 235                 240

Glu Gly Arg Met Asn Tyr Tyr Trp Thr Leu Val Glu Pro Gly Asp Lys
            245                 250                 255

Ile Thr Phe Glu Ala Thr Gly Asn Leu Val Val Pro Arg Tyr Ala Phe
        260                 265                 270

Ala Met Glu Arg Asn Ala Gly Ser Gly Ile Ile Ile Ser Asp Thr Pro
    275                 280                 285

Val His Asp Cys Asn Thr Thr Cys Gln Thr Pro Lys Gly Ala Ile Asn
290                 295                 300

Thr Ser Leu Pro Phe Gln Asn Ile His Pro Ile Thr Ile Gly Lys Cys
305                 310                 315                 320

Pro Lys Tyr Val Lys Ser Thr Lys Leu Arg Leu Ala Thr Gly Leu Arg
            325                 330                 335

Asn Ile Pro Ser Ile Gln Ser Arg Gly Leu Phe Gly Ala Ile Ala Gly
        340                 345                 350

Phe Ile Glu Gly Gly Trp Thr Gly Met Val Asp Gly Trp Tyr Gly Tyr
    355                 360                 365

His His Gln Asn Glu Gln Gly Ser Gly Tyr Ala Ala Asp Leu Lys Ser
370                 375                 380

Thr Gln Asn Ala Ile Asp Glu Ile Thr Asn Lys Val Asn Ser Val Ile
385                 390                 395                 400

Glu Lys Met Asn Thr Gln Phe Thr Ala Val Gly Lys Glu Phe Asn His
            405                 410                 415

Leu Glu Lys Arg Ile Glu Asn Leu Asn Lys Lys Val Asp Asp Gly Phe
        420                 425                 430

Leu Asp Ile Trp Thr Tyr Asn Ala Glu Leu Leu Val Leu Leu Glu Asn
    435                 440                 445

Glu Arg Thr Leu Asp Tyr His Asp Ser Asn Val Lys Asn Leu Tyr Glu
450                 455                 460

Lys Val Arg Ser Gln Leu Lys Asn Asn Ala Lys Glu Ile Gly Asn Gly
465                 470                 475                 480

Cys Phe Glu Phe Tyr His Lys Cys Asp Asn Thr Cys Met Glu Ser Val
            485                 490                 495

Lys Asn Gly Thr Tyr Asp Tyr Pro Lys Tyr Ser Glu Glu Ala Lys Leu
        500                 505                 510

Asn Arg Glu Glu Ile Asp Gly Val Lys Leu Glu Ser Thr Arg Ile Tyr
```

```
                515                 520                 525

Gln Ile Leu Ala Ile Tyr Ser Thr Val Ala Ser Ser Leu Val Leu Val
    530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 2
<211> LENGTH: 22
<212> TYPE: PRT
<213> ORGANISM: Influenza Virus

<400> SEQUENCE: 2

Asp Leu Lys Ser Thr Gln Asn Ala Ile Asp Glu Ile Thr Asn Lys Val
1               5                   10                  15

Asn Ser Val Ile Glu Lys
            20

<210> SEQ ID NO 3
<211> LENGTH: 183
<212> TYPE: PRT
<213> ORGANISM: Hepatitis B Virus

<400> SEQUENCE: 3

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp Pro Ala
65                  70                  75                  80

Ser Arg Glu Leu Val Val Ser Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Gln Ser Arg Glu Ser Gln Cys
            180

<210> SEQ ID NO 4
<211> LENGTH: 30
<212> TYPE: PRT
<213> ORGANISM: Hepatitis B Virus

<400> SEQUENCE: 4

Pro His His Thr Ala Leu Arg Gln Ala Ile Leu Cys Trp Gly Glu Leu
1               5                   10                  15
```

```
Met Asn Leu Ala Thr Trp Val Gly Ser Asn Leu Glu Asp Pro
            20                  25                  30

<210> SEQ ID NO 5
<211> LENGTH: 25
<212> TYPE: PRT
<213> ORGANISM: Hepatitis B Virus

<400> SEQUENCE: 5

Pro His His Thr Ala Leu Arg Gln Ala Ile Leu Cys Trp Gly Glu Leu
1               5                   10                  15

Met Asn Leu Ala Thr Trp Val Gly Ser
            20                  25

<210> SEQ ID NO 6
<211> LENGTH: 24
<212> TYPE: PRT
<213> ORGANISM: Hepatitis B Virus

<400> SEQUENCE: 6

Pro His His Thr Ala Leu Arg Gln Ala Ile Leu Cys Trp Gly Glu Leu
1               5                   10                  15

Met Asn Leu Ala Thr Trp Val Gly
            20

<210> SEQ ID NO 7
<211> LENGTH: 23
<212> TYPE: PRT
<213> ORGANISM: Hepatitis B Virus

<400> SEQUENCE: 7

Pro His His Thr Ala Leu Arg Gln Ala Ile Leu Cys Trp Gly Glu Leu
1               5                   10                  15

Met Asn Leu Ala Thr Trp Val
            20

<210> SEQ ID NO 8
<211> LENGTH: 22
<212> TYPE: PRT
<213> ORGANISM: Hepatitis B Virus

<400> SEQUENCE: 8

Pro His His Thr Ala Leu Arg Gln Ala Ile Leu Cys Trp Gly Glu Leu
1               5                   10                  15

Met Asn Leu Ala Thr Trp
            20

<210> SEQ ID NO 9
<211> LENGTH: 32
<212> TYPE: PRT
<213> ORGANISM: Hepatitis B Virus

<400> SEQUENCE: 9

Pro Ala Ser Arg Glu Leu Val Val Ser Tyr Val Asn Val Asn Met Gly
1               5                   10                  15

Leu Lys Ile Arg Gln Leu Leu Trp Phe His Ile Ser Cys Leu Thr Phe
            20                  25                  30

<210> SEQ ID NO 10
<211> LENGTH: 31
<212> TYPE: PRT
<213> ORGANISM: Hepatitis B Virus
```

```
<400> SEQUENCE: 10

Ala Ser Arg Glu Leu Val Val Ser Tyr Val Asn Val Asn Met Gly Leu
1               5                   10                  15

Lys Ile Arg Gln Leu Leu Trp Phe His Ile Ser Cys Leu Thr Phe
            20                  25                  30

<210> SEQ ID NO 11
<211> LENGTH: 30
<212> TYPE: PRT
<213> ORGANISM: Hepatitis B Virus

<400> SEQUENCE: 11

Ser Arg Glu Leu Val Val Ser Tyr Val Asn Val Asn Met Gly Leu Lys
1               5                   10                  15

Ile Arg Gln Leu Leu Trp Phe His Ile Ser Cys Leu Thr Phe
            20                  25                  30

<210> SEQ ID NO 12
<211> LENGTH: 29
<212> TYPE: PRT
<213> ORGANISM: Hepatitis B Virus

<400> SEQUENCE: 12

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe
            20                  25

<210> SEQ ID NO 13
<211> LENGTH: 12
<212> TYPE: PRT
<213> ORGANISM: Hepatitis B Virus

<400> SEQUENCE: 13

Pro Ala Ser Arg Glu Leu Val Val Ser Tyr Val Asn
1               5                   10

<210> SEQ ID NO 14
<211> LENGTH: 11
<212> TYPE: PRT
<213> ORGANISM: Hepatitis B Virus

<400> SEQUENCE: 14

Ala Ser Arg Glu Leu Val Val Ser Tyr Val Asn
1               5                   10

<210> SEQ ID NO 15
<211> LENGTH: 10
<212> TYPE: PRT
<213> ORGANISM: Hepatitis B Virus

<400> SEQUENCE: 15

Ser Arg Glu Leu Val Val Ser Tyr Val Asn
1               5                   10

<210> SEQ ID NO 16
<211> LENGTH: 9
<212> TYPE: PRT
<213> ORGANISM: Hepatitis B Virus

<400> SEQUENCE: 16

Arg Glu Leu Val Val Ser Tyr Val Asn
```

```
<210> SEQ ID NO 17
<211> LENGTH: 19
<212> TYPE: PRT
<213> ORGANISM: Hepatitis B Virus

<400> SEQUENCE: 17

Asn Met Gly Leu Lys Ile Arg Gln Leu Leu Trp Phe His Ile Ser Cys
1               5                   10                  15

Leu Thr Phe

<210> SEQ ID NO 18
<211> LENGTH: 10
<212> TYPE: PRT
<213> ORGANISM: Hepatitis B Virus

<400> SEQUENCE: 18

Val Gly Ser Asn Leu Glu Asp Pro Ala Ser
1               5                   10

<210> SEQ ID NO 19
<211> LENGTH: 8
<212> TYPE: PRT
<213> ORGANISM: Hepatitis B Virus

<400> SEQUENCE: 19

Ser Asn Leu Glu Asp Pro Ala Ser
1               5

<210> SEQ ID NO 20
<211> LENGTH: 7
<212> TYPE: PRT
<213> ORGANISM: Hepatitis B Virus

<400> SEQUENCE: 20

Val Gly Ser Asn Leu Glu Asp
1               5

<210> SEQ ID NO 21
<211> LENGTH: 5
<212> TYPE: PRT
<213> ORGANISM: Hepatitis B Virus

<400> SEQUENCE: 21

Ser Asn Leu Glu Asp
1               5

<210> SEQ ID NO 22
<211> LENGTH: 30
<212> TYPE: PRT
<213> ORGANISM: Hepatitis B Virus

<400> SEQUENCE: 22

Leu Glu Ser Pro Glu His Cys Ser Pro His His Thr Ala Leu Arg Gln
1               5                   10                  15

Ala Ile Leu Cys Trp Gly Glu Leu Met Asn Leu Ala Thr Trp
            20                  25                  30

<210> SEQ ID NO 23
<211> LENGTH: 40
<212> TYPE: PRT
<213> ORGANISM: Hepatitis B Virus
```

<400> SEQUENCE: 23

Asp Thr Ala Ser Ala Leu Tyr Arg Glu Ala Leu Glu Ser Pro Glu His
1               5                   10                  15

Cys Ser Pro His His Thr Ala Leu Arg Gln Ala Ile Leu Cys Trp Gly
                20                  25                  30

Glu Leu Met Asn Leu Ala Thr Trp
                35                  40

<210> SEQ ID NO 24
<211> LENGTH: 50
<212> TYPE: PRT
<213> ORGANISM: Hepatitis B Virus

<400> SEQUENCE: 24

Asp Phe Phe Pro Ser Ile Arg Asp Leu Leu Asp Thr Ala Ser Ala Leu
1               5                   10                  15

Tyr Arg Glu Ala Leu Glu Ser Pro Glu His Cys Ser Pro His His Thr
                20                  25                  30

Ala Leu Arg Gln Ala Ile Leu Cys Trp Gly Glu Leu Met Asn Leu Ala
                35                  40                  45

Thr Trp
    50

<210> SEQ ID NO 25
<211> LENGTH: 60
<212> TYPE: PRT
<213> ORGANISM: Hepatitis B Virus

<400> SEQUENCE: 25

Ser Val Glu Leu Leu Ser Phe Leu Pro Ser Asp Phe Phe Pro Ser Ile
1               5                   10                  15

Arg Asp Leu Leu Asp Thr Ala Ser Ala Leu Tyr Arg Glu Ala Leu Glu
                20                  25                  30

Ser Pro Glu His Cys Ser Pro His His Thr Ala Leu Arg Gln Ala Ile
                35                  40                  45

Leu Cys Trp Gly Glu Leu Met Asn Leu Ala Thr Trp
            50                  55                  60

<210> SEQ ID NO 26
<211> LENGTH: 70
<212> TYPE: PRT
<213> ORGANISM: Hepatitis B Virus

<400> SEQUENCE: 26

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe Gly Arg Glu
                20                  25                  30

Thr Val Leu Glu Tyr Leu Val Ser Phe Gly Val Trp Ile Arg Thr Pro
                35                  40                  45

Pro Ala Tyr Arg Pro Pro Asn Ala Pro Ile Leu Ser Thr Leu Pro Glu
            50                  55                  60

Thr Thr Val Val Arg Arg
65                  70

<210> SEQ ID NO 27
<211> LENGTH: 60
<212> TYPE: PRT
<213> ORGANISM: Hepatitis B Virus

<400> SEQUENCE: 27

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe Gly Arg Glu
            20                  25                  30

Thr Val Leu Glu Tyr Leu Val Ser Phe Gly Val Trp Ile Arg Thr Pro
        35                  40                  45

Pro Ala Tyr Arg Pro Pro Asn Ala Pro Ile Leu Ser
    50                  55                  60

<210> SEQ ID NO 28
<211> LENGTH: 50
<212> TYPE: PRT
<213> ORGANISM: Hepatitis B Virus

<400> SEQUENCE: 28

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe Gly Arg Glu
            20                  25                  30

Thr Val Leu Glu Tyr Leu Val Ser Phe Gly Val Trp Ile Arg Thr Pro
        35                  40                  45

Pro Ala
    50

<210> SEQ ID NO 29
<211> LENGTH: 40
<212> TYPE: PRT
<213> ORGANISM: Hepatitis B Virus

<400> SEQUENCE: 29

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe Gly Arg Glu
            20                  25                  30

Thr Val Leu Glu Tyr Leu Val Ser
        35                  40

<210> SEQ ID NO 30
<211> LENGTH: 78
<212> TYPE: PRT
<213> ORGANISM: Hepatitis B Virus

<400> SEQUENCE: 30

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly Ser Asn Leu Glu Asp
65                  70                  75

<210> SEQ ID NO 31
<211> LENGTH: 73
<212> TYPE: PRT

<213> ORGANISM: Hepatitis B Virus

<400> SEQUENCE: 31

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val Gly
65                  70

<210> SEQ ID NO 32
<211> LENGTH: 72
<212> TYPE: PRT
<213> ORGANISM: Hepatitis B Virus

<400> SEQUENCE: 32

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Val
65                  70

<210> SEQ ID NO 33
<211> LENGTH: 71
<212> TYPE: PRT
<213> ORGANISM: Hepatitis B Virus

<400> SEQUENCE: 33

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp
65                  70

<210> SEQ ID NO 34
<211> LENGTH: 65
<212> TYPE: PRT
<213> ORGANISM: Hepatitis B Virus

<400> SEQUENCE: 34

Pro Ala Ser Arg Glu Leu Val Val Ser Tyr Val Asn Val Asn Met Gly
1               5                   10                  15

Leu Lys Ile Arg Gln Leu Leu Trp Phe His Ile Ser Cys Leu Thr Phe
            20                  25                  30

Gly Arg Glu Thr Val Leu Glu Tyr Leu Val Ser Phe Gly Val Trp Ile
            35                  40                  45

Arg Thr Pro Pro Ala Tyr Arg Pro Pro Asn Ala Pro Ile Leu Ser Thr
    50                  55                  60

Leu
65

<210> SEQ ID NO 35
<211> LENGTH: 64
<212> TYPE: PRT
<213> ORGANISM: Hepatitis B Virus

<400> SEQUENCE: 35

Ala Ser Arg Glu Leu Val Val Ser Tyr Val Asn Val Asn Met Gly Leu
1               5                   10                  15

Lys Ile Arg Gln Leu Leu Trp Phe His Ile Ser Cys Leu Thr Phe Gly
            20                  25                  30

Arg Glu Thr Val Leu Glu Tyr Leu Val Ser Phe Gly Val Trp Ile Arg
        35                  40                  45

Thr Pro Pro Ala Tyr Arg Pro Pro Asn Ala Pro Ile Leu Ser Thr Leu
    50                  55                  60

<210> SEQ ID NO 36
<211> LENGTH: 63
<212> TYPE: PRT
<213> ORGANISM: Hepatitis B Virus

<400> SEQUENCE: 36

Ser Arg Glu Leu Val Val Ser Tyr Val Asn Val Asn Met Gly Leu Lys
1               5                   10                  15

Ile Arg Gln Leu Leu Trp Phe His Ile Ser Cys Leu Thr Phe Gly Arg
            20                  25                  30

Glu Thr Val Leu Glu Tyr Leu Val Ser Phe Gly Val Trp Ile Arg Thr
        35                  40                  45

Pro Pro Ala Tyr Arg Pro Pro Asn Ala Pro Ile Leu Ser Thr Leu
    50                  55                  60

<210> SEQ ID NO 37
<211> LENGTH: 62
<212> TYPE: PRT
<213> ORGANISM: Hepatitis B Virus

<400> SEQUENCE: 37

Arg Glu Leu Val Val Ser Tyr Val Asn Val Asn Met Gly Leu Lys Ile
1               5                   10                  15

Arg Gln Leu Leu Trp Phe His Ile Ser Cys Leu Thr Phe Gly Arg Glu
            20                  25                  30

Thr Val Leu Glu Tyr Leu Val Ser Phe Gly Val Trp Ile Arg Thr Pro
        35                  40                  45

Pro Ala Tyr Arg Pro Pro Asn Ala Pro Ile Leu Ser Thr Leu
    50                  55                  60

<210> SEQ ID NO 38
<211> LENGTH: 226
<212> TYPE: PRT
<213> ORGANISM: Artificial sequence
<220> FEATURE:
<223> OTHER INFORMATION: Synthetic

<400> SEQUENCE: 38

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Asp Leu Lys Ser Thr Gln Asn Ala Ile
65                  70                  75                  80

Asp Glu Ile Thr Asn Lys Val Asn Ser Val Ile Glu Lys Val Gly Ser
                85                  90                  95

Asn Leu Glu Asp Pro Ala Ser Asp Leu Lys Ser Thr Gln Asn Ala Ile
            100                 105                 110

Asp Glu Ile Thr Asn Lys Val Asn Ser Val Ile Glu Lys Arg Glu Leu
            115                 120                 125

Trp Ser Tyr Val Asn Val Asn Met Gly Leu Lys Ile Arg Gln Leu Leu
        130                 135                 140

Trp Phe His Ile Ser Cys Leu Thr Phe Gly Arg Glu Thr Val Leu Glu
145                 150                 155                 160

Tyr Leu Val Ser Phe Gly Val Trp Ile Arg Thr Pro Pro Ala Tyr Arg
                165                 170                 175

Pro Pro Asn Ala Pro Ile Leu Ser Thr Leu Pro Glu Thr Thr Val Val
            180                 185                 190

Arg Arg Arg Gly Arg Ser Pro Arg Arg Thr Pro Ser Pro Arg Arg
        195                 200                 205

Arg Arg Ser Gln Ser Pro Arg Arg Arg Ser Gln Ser Arg Glu Ser
    210                 215                 220

Gln Cys
225

<210> SEQ ID NO 39
<211> LENGTH: 238
<212> TYPE: PRT
<213> ORGANISM: Artificial sequence
<220> FEATURE:
<223> OTHER INFORMATION: Synthetic

<400> SEQUENCE: 39

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Gly Asp Leu Lys Ser Thr Gln
65                  70                  75                  80

Asn Ala Ile Asp Glu Ile Thr Asn Lys Val Asn Ser Val Ile Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Asn Ala Ile Asp Glu Ile Thr Asn Lys Val
            115                 120                 125

```
Asn Ser Val Ile Glu Lys Gly Gly Arg Glu Leu Trp Ser Tyr Val
    130                 135                 140

Asn Val Asn Met Gly Leu Lys Ile Arg Gln Leu Leu Trp Phe His Ile
145                 150                 155                 160

Ser Cys Leu Thr Phe Gly Arg Glu Thr Val Leu Glu Tyr Leu Val Ser
                165                 170                 175

Phe Gly Val Trp Ile Arg Thr Pro Ala Tyr Arg Pro Pro Asn Ala
            180                 185                 190

Pro Ile Leu Ser Thr Leu Pro Glu Thr Thr Val Arg Arg Gly
            195                 200                 205

Arg Ser Pro Arg Arg Thr Pro Ser Pro Arg Arg Arg Ser Gln
210                 215                 220

Ser Pro Arg Arg Arg Ser Gln Ser Arg Glu Ser Gln Cys
225                 230                 235
```

<210> SEQ ID NO 40
<211> LENGTH: 239
<212> TYPE: PRT
<213> ORGANISM: Artificial Sequence
<220> FEATURE:
<223> OTHER INFORMATION: Synthetic

<400> SEQUENCE: 40

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Leu Lys Ser Thr Gln
65                  70                  75              80

Asn Ala Ile Asp Glu Ile Thr Asn Lys Val Asn Ser Val Ile Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Asn Ala Ile Asp Glu Ile Thr Asn Lys Val
        115                 120                 125

Asn Ser Val Ile Glu Lys Gly Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Ser
210                 215                 220

Gln Ser Pro Arg Arg Arg Arg Ser Gln Ser Arg Glu Ser Gln Cys
225                 230                 235
```

<210> SEQ ID NO 41
<211> LENGTH: 239

```
<212> TYPE: PRT
<213> ORGANISM: Artificial Sequence
<220> FEATURE:
<223> OTHER INFORMATION: Synthetic

<400> SEQUENCE: 41

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Gln Lys Ser Thr Gln
65                  70                  75                  80

Asn Ala Ile Asn Gly Ile Thr Asn Lys Val Asn Ser Ile Ile Glu Lys
                85                  90                  95

Gly Gly Gly Val Gly Ser Asn Leu Glu Asp Pro Ala Ser Gly Gly
                100                 105                 110

Asp Gln Lys Ser Thr Gln Asn Ala Ile Asn Gly Ile Thr Asn Lys Val
            115                 120                 125

Asn Ser Ile Ile Glu Lys Gly Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
        210                 215                 220

Gln Ser Pro Arg Arg Arg Ser Gln Ser Arg Glu Ser Gln Cys
225                 230                 235

<210> SEQ ID NO 42
<211> LENGTH: 239
<212> TYPE: PRT
<213> ORGANISM: Artificial Sequence
<220> FEATURE:
<223> OTHER INFORMATION: Synthetic

<400> SEQUENCE: 42

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Gln Lys Ser Thr Gln
65                  70                  75                  80

Asn Ala Ile Asn Gly Ile Thr Asn Lys Val Asn Ser Val Ile Glu Lys
                85                  90                  95
```

```
Gly Gly Gly Val Gly Ser Asn Leu Glu Asp Pro Ala Ser Gly Gly Gly
            100                 105                 110

Asp Gln Lys Ser Thr Gln Asn Ala Ile Asn Gly Ile Thr Asn Lys Val
            115                 120                 125

Asn Ser Val Ile Glu Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
210                 215                 220

Gln Ser Pro Arg Arg Arg Arg Ser Gln Ser Arg Glu Ser Gln Cys
225                 230                 235
```

<210> SEQ ID NO 43
<211> LENGTH: 239
<212> TYPE: PRT
<213> ORGANISM: Artificial Sequence
<220> FEATURE:
<223> OTHER INFORMATION: Synthetic

<400> SEQUENCE: 43

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Gly Asp Gln Lys Ser Thr Gln
65                  70                  75                  80

Asn Ala Ile Asn Gly Ile Thr Asn Lys Val Asn Thr Val Ile Glu Lys
                85                  90                  95

Gly Gly Gly Val Gly Ser Asn Leu Glu Asp Pro Ala Ser Gly Gly Gly
            100                 105                 110

Asp Gln Lys Ser Thr Gln Asn Ala Ile Asn Gly Ile Thr Asn Lys Val
            115                 120                 125

Asn Thr Val Ile Glu Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
210                 215                 220
```

```
Gln Ser Pro Arg Arg Arg Ser Gln Ser Arg Glu Ser Gln Cys
225                 230                 235
```

<210> SEQ ID NO 44
<211> LENGTH: 239
<212> TYPE: PRT
<213> ORGANISM: Artificial Sequence
<220> FEATURE:
<223> OTHER INFORMATION: Synthetic

<400> SEQUENCE: 44

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Lys Glu Ser Thr Gln
65                  70                  75                  80

Lys Ala Phe Asp Gly Ile Thr Asn Lys Val Asn Ala Val Ile Glu Lys
                85                  90                  95

Gly Gly Gly Val Gly Ser Asn Leu Glu Asp Pro Ala Ser Gly Gly
            100                 105                 110

Asp Lys Glu Ser Thr Gln Lys Ala Phe Asp Gly Ile Thr Asn Lys Val
        115                 120                 125

Asn Ala Val Ile Glu Lys Gly Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Arg Arg Arg
        195                 200                 205

Gly Arg Ser Pro Arg Arg Arg Thr Pro Ser Pro Arg Arg Arg Ser
    210                 215                 220

Gln Ser Pro Arg Arg Arg Ser Gln Ser Arg Glu Ser Gln Cys
225                 230                 235
```

<210> SEQ ID NO 45
<211> LENGTH: 239
<212> TYPE: PRT
<213> ORGANISM: Artificial Sequence
<220> FEATURE:
<223> OTHER INFORMATION: Synthetic

<400> SEQUENCE: 45

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
```

```
                50                  55                  60
Leu Met Asn Leu Ala Thr Trp Gly Gly Gly Asp Lys Glu Ser Thr Gln
 65                  70                  75                  80

Lys Ala Phe Asp Gly Ile Thr Asn Lys Val Asn Ser Val Ile Glu Lys
                 85                  90                  95

Gly Gly Gly Val Gly Ser Asn Leu Glu Asp Pro Ala Ser Gly Gly Gly
                100                 105                 110

Asp Lys Glu Ser Thr Gln Lys Ala Phe Asp Gly Ile Thr Asn Lys Val
            115                 120                 125

Asn Ser Val Ile Glu Lys Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Thr Pro Ser Pro Arg Arg Arg Arg Ser
210                 215                 220

Gln Ser Pro Arg Arg Arg Ser Gln Ser Arg Glu Ser Gln Cys
225                 230                 235
```

<210> SEQ ID NO 46
<211> LENGTH: 239
<212> TYPE: PRT
<213> ORGANISM: Artificial Sequence
<220> FEATURE:
<223> OTHER INFORMATION: Synthetic

<400> SEQUENCE: 46

```
Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Gly Asp Leu Lys Ser Thr Gln
 65                  70                  75                  80

Ala Ala Ile Asp Gln Ile Asn Gly Lys Leu Asn Arg Leu Ile Gly Lys
                 85                  90                  95

Gly Gly Gly Val Gly Ser Asn Leu Glu Asp Pro Ala Ser Gly Gly Gly
                100                 105                 110

Asp Leu Lys Ser Thr Gln Ala Ala Ile Asp Gln Ile Asn Gly Lys Leu
            115                 120                 125

Asn Arg Leu Ile Gly Lys Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
```

```
                180               185                 190
Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
            210                 215                 220

Gln Ser Pro Arg Arg Arg Arg Ser Gln Ser Arg Glu Ser Gln Cys
225                 230                 235
```

<210> SEQ ID NO 47
<211> LENGTH: 239
<212> TYPE: PRT
<213> ORGANISM: Artificial Sequence
<220> FEATURE:
<223> OTHER INFORMATION: Synthetic

<400> SEQUENCE: 47

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Leu Lys Ser Thr Gln
65                  70                  75                  80

Ala Ala Ile Asp Gln Ile Asn Gly Lys Leu Asn Arg Leu Val Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asp Gln Ile Asn Gly Lys Leu
            115                 120                 125

Asn Arg Leu Val Glu Lys Gly Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
            210                 215                 220

Gln Ser Pro Arg Arg Arg Arg Ser Gln Ser Arg Glu Ser Gln Cys
225                 230                 235
```

<210> SEQ ID NO 48
<211> LENGTH: 239
<212> TYPE: PRT
<213> ORGANISM: Artificial Sequence
<220> FEATURE:
<223> OTHER INFORMATION: Synthetic

<400> SEQUENCE: 48

```
Met Asp Ile Asp Pro Tyr Lys Glu Phe Gly Ala Ser Val Glu Leu Leu
1               5                   10                  15
```

```
Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Gly Asp Leu Lys Ser Thr Gln
65                  70                  75                  80

Ala Ala Ile Asp Gln Ile Asn Gly Lys Leu Asn Arg Val Ile Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asp Gln Ile Asn Gly Lys Leu
        115                 120                 125

Asn Arg Val Ile Glu Lys Gly Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Arg Ser Gln Ser Arg Glu Ser Gln Cys
225                 230                 235

<210> SEQ ID NO 49
<211> LENGTH: 239
<212> TYPE: PRT
<213> ORGANISM: Artificial Sequence
<220> FEATURE:
<223> OTHER INFORMATION: Synthetic

<400> SEQUENCE: 49

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Gly Asp Leu Lys Ser Thr Gln
65                  70                  75                  80

Ala Ala Ile Asn Gln Ile Asn Gly Lys Leu Asn Arg Leu Ile Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asn Gln Ile Asn Gly Lys Leu
        115                 120                 125

Asn Arg Leu Ile Glu Lys Gly Gly Gly Arg Glu Leu Val Val Ser Tyr
    130                 135                 140
```

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Arg Arg Arg
        195                 200                 205

Gly Arg Ser Pro Arg Arg Thr Pro Ser Pro Arg Arg Arg Ser
    210                 215                 220

Gln Ser Pro Arg Arg Arg Ser Gln Ser Arg Glu Ser Gln Cys
225                 230                 235

<210> SEQ ID NO 50
<211> LENGTH: 239
<212> TYPE: PRT
<213> ORGANISM: Artificial Sequence
<220> FEATURE:
<223> OTHER INFORMATION: Synthetic

<400> SEQUENCE: 50

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Leu Lys Ser Thr Gln
65                  70                  75                  80

Ala Ala Ile Asn Gln Ile Asn Gly Lys Leu Asn Arg Leu Ile Gly Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asn Gln Ile Asn Gly Lys Leu
        115                 120                 125

Asn Arg Leu Ile Gly Lys Gly Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Arg Arg Arg
        195                 200                 205

Gly Arg Ser Pro Arg Arg Thr Pro Ser Pro Arg Arg Arg Ser
    210                 215                 220

Gln Ser Pro Arg Arg Arg Ser Gln Ser Arg Glu Ser Gln Cys
225                 230                 235

<210> SEQ ID NO 51
<211> LENGTH: 239
<212> TYPE: PRT
<213> ORGANISM: Artificial Sequence
<220> FEATURE:

<223> OTHER INFORMATION: Synthetic

<400> SEQUENCE: 51

| | | | | | | | | | | | | | | |
|---|---|---|---|---|---|---|---|---|---|---|---|---|---|---|
|Met|Asp|Ile|Asp|Pro|Tyr|Lys|Glu|Phe|Gly|Ala|Ser|Val|Glu|Leu|Leu|
|1| | | |5| | | | |10| | | | |15|

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Leu Lys Ser Thr Gln
65                  70                  75                  80

Ala Ala Ile Asn Gln Ile Thr Gly Lys Leu Asn Arg Val Ile Lys Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asn Gln Ile Thr Gly Lys Leu
            115                 120                 125

Asn Arg Val Ile Lys Lys Gly Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Arg Ser Gln Ser Arg Glu Ser Gln Cys
225                 230                 235

<210> SEQ ID NO 52
<211> LENGTH: 239
<212> TYPE: PRT
<213> ORGANISM: Artificial Sequence
<220> FEATURE:
<223> OTHER INFORMATION: Synthetic

<400> SEQUENCE: 52

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Leu Lys Ser Thr Gln
65                  70                  75                  80

Ala Ala Ile Asp Gln Ile Asn Gly Lys Leu Asn Arg Leu Ile Glu Lys
                85                  90                  95

Gly Gly Gly Val Gly Ser Asn Leu Glu Asp Pro Ala Ser Gly Gly Gly
            100                 105                 110

Asp Leu Lys Ser Thr Gln Ala Ala Ile Asp Gln Ile Asn Gly Lys Leu
            115                 120                 125

Asn Arg Leu Ile Glu Lys Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Val Arg Arg Arg
                195                 200                 205

Gly Arg Ser Pro Arg Arg Arg Thr Pro Ser Pro Arg Arg Arg Arg Ser
            210                 215                 220

Gln Ser Pro Arg Arg Arg Arg Ser Gln Ser Arg Glu Ser Gln Cys
225                 230                 235

<210> SEQ ID NO 53
<211> LENGTH: 239
<212> TYPE: PRT
<213> ORGANISM: Artificial Sequence
<220> FEATURE:
<223> OTHER INFORMATION: Synthetic

<400> SEQUENCE: 53

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Lys Glu Ser Thr Gln
65                  70                  75                  80

Lys Ala Ile Asp Gly Ile Thr Asn Lys Val Asn Ser Ile Ile Asp Lys
                85                  90                  95

Gly Gly Gly Val Gly Ser Asn Leu Glu Asp Pro Ala Ser Gly Gly Gly
                100                 105                 110

Asp Lys Glu Ser Thr Gln Lys Ala Ile Asp Gly Ile Thr Asn Lys Val
            115                 120                 125

Asn Ser Ile Ile Asp Lys Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Val Arg Arg Arg
                195                 200                 205

Gly Arg Ser Pro Arg Arg Arg Thr Pro Ser Pro Arg Arg Arg Arg Ser
            210                 215                 220

Gln Ser Pro Arg Arg Arg Arg Ser Gln Ser Arg Glu Ser Gln Cys
225                 230                 235

<210> SEQ ID NO 54
<211> LENGTH: 239
<212> TYPE: PRT
<213> ORGANISM: Artificial Sequence
<220> FEATURE:
<223> OTHER INFORMATION: Synthetic

<400> SEQUENCE: 54

```
Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Gly Asp Lys Glu Ser Thr Gln
65                  70                  75                  80

Lys Ala Ile Asp Gly Val Thr Asn Lys Val Asn Ser Ile Ile Asp Lys
                85                  90                  95

Gly Gly Gly Val Gly Ser Asn Leu Glu Asp Pro Ala Ser Gly Gly
                100                 105                 110

Asp Lys Glu Ser Thr Gln Lys Ala Ile Asp Gly Val Thr Asn Lys Val
            115                 120                 125

Asn Ser Ile Ile Asp Lys Gly Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Ser Gln Ser Arg Glu Ser Gln Cys
225                 230                 235
```

<210> SEQ ID NO 55
<211> LENGTH: 239
<212> TYPE: PRT
<213> ORGANISM: Artificial Sequence
<220> FEATURE:
<223> OTHER INFORMATION: Synthetic

<400> SEQUENCE: 55

```
Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Gly Asp Lys Glu Ser Thr Gln
```

```
            65                  70                  75                  80
Lys Ala Ile Asp Gly Val Thr Asn Lys Val Asn Ser Ile Ile Asn Lys
                    85                  90                  95
Gly Gly Gly Val Gly Ser Asn Leu Glu Asp Pro Ala Ser Gly Gly Gly
                    100                 105                 110
Asp Lys Glu Ser Thr Gln Lys Ala Ile Asp Gly Val Thr Asn Lys Val
                    115                 120                 125
Asn Ser Ile Ile Asn Lys Gly Gly Arg Glu Leu Val Val Ser Tyr
                    130                 135                 140
Val Asn Val Asn Met Gly Leu Lys Ile Arg Gln Leu Leu Trp Phe His
145                 150                 155                 160
Ile Ser Cys Leu Thr Phe Gly Arg Glu Thr Val Leu Glu Tyr Leu Val
                    165                 170                 175
Ser Phe Gly Val Trp Ile Arg Thr Pro Pro Ala Tyr Arg Pro Pro Asn
                    180                 185                 190
Ala Pro Ile Leu Ser Thr Leu Pro Glu Thr Thr Val Val Arg Arg Arg
                    195                 200                 205
Gly Arg Ser Pro Arg Arg Thr Pro Ser Arg Arg Arg Ser
                    210                 215                 220
Gln Ser Pro Arg Arg Arg Arg Ser Gln Ser Arg Glu Ser Gln Cys
225                 230                 235

<210> SEQ ID NO 56
<211> LENGTH: 239
<212> TYPE: PRT
<213> ORGANISM: Artificial Sequence
<220> FEATURE:
<223> OTHER INFORMATION: Synthetic

<400> SEQUENCE: 56

Met Asp Ile Asp Pro Tyr Lys Glu Phe Gly Ala Ser Val Glu Leu Leu
1               5                   10                  15
Ser Phe Leu Pro Ser Asp Phe Phe Pro Ser Ile Arg Asp Leu Leu Asp
                    20                  25                  30
Thr Ala Ser Ala Leu Tyr Arg Glu Ala Leu Glu Ser Pro Glu His Cys
                    35                  40                  45
Ser Pro His His Thr Ala Leu Arg Gln Ala Ile Leu Cys Trp Gly Glu
                    50                  55                  60
Leu Met Asn Leu Ala Thr Trp Gly Gly Gly Asp Tyr Lys Ser Thr Gln
65                  70                  75                  80
Ser Ala Ile Asp Gln Ile Thr Gly Lys Leu Asn Arg Leu Ile Gly Lys
                    85                  90                  95
Gly Gly Gly Val Gly Ser Asn Leu Glu Asp Pro Ala Ser Gly Gly Gly
                    100                 105                 110
Asp Tyr Lys Ser Thr Gln Ser Ala Ile Asp Gln Ile Thr Gly Lys Leu
                    115                 120                 125
Asn Arg Leu Ile Gly Lys Gly Gly Arg Glu Leu Val Val Ser Tyr
                    130                 135                 140
Val Asn Val Asn Met Gly Leu Lys Ile Arg Gln Leu Leu Trp Phe His
145                 150                 155                 160
Ile Ser Cys Leu Thr Phe Gly Arg Glu Thr Val Leu Glu Tyr Leu Val
                    165                 170                 175
Ser Phe Gly Val Trp Ile Arg Thr Pro Pro Ala Tyr Arg Pro Pro Asn
                    180                 185                 190
Ala Pro Ile Leu Ser Thr Leu Pro Glu Thr Thr Val Val Arg Arg Arg
```

```
            195                 200                 205
Gly Arg Ser Pro Arg Arg Arg Thr Pro Ser Pro Arg Arg Arg Ser
    210                 215                 220
Gln Ser Pro Arg Arg Arg Ser Gln Ser Arg Glu Ser Gln Cys
225                 230                 235
```

<210> SEQ ID NO 57
<211> LENGTH: 239
<212> TYPE: PRT
<213> ORGANISM: Artificial Sequence
<220> FEATURE:
<223> OTHER INFORMATION: Synthetic

<400> SEQUENCE: 57

```
Met Asp Ile Asp Pro Tyr Lys Glu Phe Gly Ala Ser Val Glu Leu Leu
1               5                   10                  15
Ser Phe Leu Pro Ser Asp Phe Phe Pro Ser Ile Arg Asp Leu Leu Asp
                20                  25                  30
Thr Ala Ser Ala Leu Tyr Arg Glu Ala Leu Glu Ser Pro Glu His Cys
            35                  40                  45
Ser Pro His His Thr Ala Leu Arg Gln Ala Ile Leu Cys Trp Gly Glu
        50                  55                  60
Leu Met Asn Leu Ala Thr Trp Gly Gly Asp Tyr Lys Ser Thr Gln
65                  70                  75                  80
Ser Ala Ile Asp Gln Ile Thr Gly Lys Leu Asn Arg Leu Ile Glu Lys
                85                  90                  95
Gly Gly Gly Val Gly Ser Asn Leu Glu Asp Pro Ala Ser Gly Gly Gly
            100                 105                 110
Asp Tyr Lys Ser Thr Gln Ser Ala Ile Asp Gln Ile Thr Gly Lys Leu
        115                 120                 125
Asn Arg Leu Ile Glu Lys Gly Gly Gly Arg Glu Leu Val Val Ser Tyr
130                 135                 140
Val Asn Val Asn Met Gly Leu Lys Ile Arg Gln Leu Leu Trp Phe His
145                 150                 155                 160
Ile Ser Cys Leu Thr Phe Gly Arg Glu Thr Val Leu Glu Tyr Leu Val
                165                 170                 175
Ser Phe Gly Val Trp Ile Arg Thr Pro Pro Ala Tyr Arg Pro Pro Asn
            180                 185                 190
Ala Pro Ile Leu Ser Thr Leu Pro Glu Thr Thr Val Val Arg Arg Arg
        195                 200                 205
Gly Arg Ser Pro Arg Arg Arg Thr Pro Ser Pro Arg Arg Arg Ser
    210                 215                 220
Gln Ser Pro Arg Arg Arg Ser Gln Ser Arg Glu Ser Gln Cys
225                 230                 235
```

<210> SEQ ID NO 58
<211> LENGTH: 239
<212> TYPE: PRT
<213> ORGANISM: Artificial Sequence
<220> FEATURE:
<223> OTHER INFORMATION: Synthetic

<400> SEQUENCE: 58

```
Met Asp Ile Asp Pro Tyr Lys Glu Phe Gly Ala Ser Val Glu Leu Leu
1               5                   10                  15
Ser Phe Leu Pro Ser Asp Phe Phe Pro Ser Ile Arg Asp Leu Leu Asp
                20                  25                  30
```

```
Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Asn Leu Ala Thr Trp Gly Gly Gly Asp Gln Lys Ser Thr Gln
 65                  70                  75                  80

Glu Ala Ile Asp Lys Ile Thr Asn Lys Val Asn Asn Ile Val Asp Lys
                85                  90                  95

Gly Gly Gly Val Gly Ser Asn Leu Glu Asp Pro Ala Ser Gly Gly Gly
            100                 105                 110

Asp Gln Lys Ser Thr Gln Glu Ala Ile Asp Lys Ile Thr Asn Lys Val
            115                 120                 125

Asn Asn Ile Val Asp Lys Gly Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
            210                 215                 220

Gln Ser Pro Arg Arg Arg Ser Gln Ser Arg Glu Ser Gln Cys
225                 230                 235

<210> SEQ ID NO 59
<211> LENGTH: 239
<212> TYPE: PRT
<213> ORGANISM: Artificial Sequence
<220> FEATURE:
<223> OTHER INFORMATION: Synthetic

<400> SEQUENCE: 59

Met Asp Ile Asp Pro Tyr Lys Glu Phe Gly Ala Ser Val Glu Leu Leu
 1               5                  10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
 50                  55                  60

Leu Met Asn Leu Ala Thr Trp Gly Gly Gly Asp Arg Asp Ser Thr Gln
 65                  70                  75                  80

Lys Ala Ile Asp Lys Ile Thr Ser Lys Val Asn Asn Ile Val Asp Lys
                85                  90                  95

Gly Gly Gly Val Gly Ser Asn Leu Glu Asp Pro Ala Ser Gly Gly Gly
            100                 105                 110

Asp Arg Asp Ser Thr Gln Lys Ala Ile Asp Lys Ile Thr Ser Lys Val
            115                 120                 125

Asn Asn Ile Val Asp Lys Gly Gly Gly Arg Glu Leu Val Val Ser Tyr
130                 135                 140

Val Asn Val Asn Met Gly Leu Lys Ile Arg Gln Leu Leu Trp Phe His
145                 150                 155                 160
```

Ile Ser Cys Leu Thr Phe Gly Arg Glu Thr Val Leu Glu Tyr Leu Val
            165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Thr Pro Ser Pro Arg Arg Arg Arg Arg Ser
            210                 215                 220

Gln Ser Pro Arg Arg Arg Arg Ser Gln Ser Arg Glu Ser Gln Cys
225                 230                 235

<210> SEQ ID NO 60
<211> LENGTH: 239
<212> TYPE: PRT
<213> ORGANISM: Artificial Sequence
<220> FEATURE:
<223> OTHER INFORMATION: Synthetic

<400> SEQUENCE: 60

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Arg Asp Ser Thr Gln
65                  70                  75                  80

Arg Ala Ile Asp Lys Ile Thr Ser Lys Val Asn Asn Ile Val Asp Lys
                85                  90                  95

Gly Gly Gly Val Gly Ser Asn Leu Glu Asp Pro Ala Ser Gly Gly Gly
            100                 105                 110

Asp Arg Asp Ser Thr Gln Arg Ala Ile Asp Lys Ile Thr Ser Lys Val
            115                 120                 125

Asn Asn Ile Val Asp Lys Gly Gly Gly Arg Glu Leu Val Val Ser Tyr
        130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
            165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Thr Pro Ser Pro Arg Arg Arg Arg Arg Ser
            210                 215                 220

Gln Ser Pro Arg Arg Arg Arg Ser Gln Ser Arg Glu Ser Gln Cys
225                 230                 235

<210> SEQ ID NO 61
<211> LENGTH: 239
<212> TYPE: PRT
<213> ORGANISM: Artificial Sequence
<220> FEATURE:
<223> OTHER INFORMATION: Synthetic

<400> SEQUENCE: 61

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Tyr Lys Ser Thr Gln
65                  70                  75                  80

Ala Ala Ile Asp Gln Ile Thr Gly Lys Leu Asn Arg Ile Ile Lys Lys
                85                  90                  95

Gly Gly Gly Val Gly Ser Asn Leu Glu Asp Pro Ala Ser Gly Gly Gly
                100                 105                 110

Asp Tyr Lys Ser Thr Gln Ala Ala Ile Asp Gln Ile Thr Gly Lys Leu
            115                 120                 125

Asn Arg Ile Ile Lys Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Val Arg Arg Arg
                195                 200                 205

Gly Arg Ser Pro Arg Arg Arg Thr Pro Ser Pro Arg Arg Arg Arg Ser
210                 215                 220

Gln Ser Pro Arg Arg Arg Arg Ser Gln Ser Arg Glu Ser Gln Cys
225                 230                 235

<210> SEQ ID NO 62
<211> LENGTH: 239
<212> TYPE: PRT
<213> ORGANISM: Artificial Sequence
<220> FEATURE:
<223> OTHER INFORMATION: Synthetic

<400> SEQUENCE: 62

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Lys Glu Ser Thr Gln
65                  70                  75                  80

Thr Ala Ile Asp Gln Ile Thr Ser Lys Val Asn Asn Ile Val Asp Arg
                85                  90                  95

Gly Gly Gly Val Gly Ser Asn Leu Glu Asp Pro Ala Ser Gly Gly Gly
                100                 105                 110

Asp Lys Glu Ser Thr Gln Thr Ala Ile Asp Gln Ile Thr Ser Lys Val
            115                 120                 125

Asn Asn Ile Val Asp Arg Gly Gly Arg Glu Leu Val Val Ser Tyr
            130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Arg Arg Arg
            195                 200                 205

Gly Arg Ser Pro Arg Arg Thr Pro Ser Pro Arg Arg Arg Ser
            210                 215                 220

Gln Ser Pro Arg Arg Arg Ser Gln Ser Arg Glu Ser Gln Cys
225                 230                 235

<210> SEQ ID NO 63
<211> LENGTH: 239
<212> TYPE: PRT
<213> ORGANISM: Artificial Sequence
<220> FEATURE:
<223> OTHER INFORMATION: Synthetic

<400> SEQUENCE: 63

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Asp Arg Asp Ser Thr Gln
65                  70                  75              80

Arg Ala Ile Asp Asn Met Gln Asn Lys Leu Asn Asn Val Ile Asp Lys
                85                  90                  95

Gly Gly Gly Val Gly Ser Asn Leu Glu Asp Pro Ala Ser Gly Gly
            100                 105                 110

Asp Arg Asp Ser Thr Gln Arg Ala Ile Asp Asn Met Gln Asn Lys Leu
        115                 120                 125

Asn Asn Val Ile Asp Lys Gly Gly Arg Glu Leu Val Val Ser Tyr
            130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Arg Arg Arg
            195                 200                 205

Gly Arg Ser Pro Arg Arg Thr Pro Ser Pro Arg Arg Arg Ser
            210                 215                 220

Gln Ser Pro Arg Arg Arg Ser Gln Ser Arg Glu Ser Gln Cys
225                 230                 235

<210> SEQ ID NO 64

<211> LENGTH: 239
<212> TYPE: PRT
<213> ORGANISM: Artificial Sequence
<220> FEATURE:
<223> OTHER INFORMATION: Synthetic

<400> SEQUENCE: 64

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Gly Asp Lys Glu Ser Thr Gln
65                  70                  75                  80

Lys Ala Ile Asp Gln Ile Thr Thr Lys Ile Asn Asn Ile Ile Asp Lys
                85                  90                  95

Gly Gly Gly Val Gly Ser Asn Leu Glu Asp Pro Ala Ser Gly Gly Gly
            100                 105                 110

Asp Lys Glu Ser Thr Gln Lys Ala Ile Asp Gln Ile Thr Thr Lys Ile
        115                 120                 125

Asn Asn Ile Ile Asp Lys Gly Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Ser Gln Ser Arg Glu Ser Gln Cys
225                 230                 235
```

<210> SEQ ID NO 65
<211> LENGTH: 239
<212> TYPE: PRT
<213> ORGANISM: Artificial Sequence
<220> FEATURE:
<223> OTHER INFORMATION: Synthetic

<400> SEQUENCE: 65

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Gly Asp Tyr Lys Ser Thr Gln
65                  70                  75                  80

Ala Ala Ile Asp Gln Ile Thr Gly Lys Leu Asn Arg Leu Ile Glu Lys
```

```
                85                  90                  95
Gly Gly Gly Val Gly Ser Asn Leu Glu Asp Pro Ala Ser Gly Gly Gly
            100                 105                 110

Asp Tyr Lys Ser Thr Gln Ala Ala Ile Asp Gln Ile Thr Gly Lys Leu
            115                 120                 125

Asn Arg Leu Ile Glu Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
            210                 215                 220

Gln Ser Pro Arg Arg Arg Arg Ser Gln Ser Arg Glu Ser Gln Cys
225                 230                 235
```

<210> SEQ ID NO 66
<211> LENGTH: 239
<212> TYPE: PRT
<213> ORGANISM: Artificial Sequence
<220> FEATURE:
<223> OTHER INFORMATION: Synthetic

<400> SEQUENCE: 66

```
Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Asn Leu Ala Thr Trp Gly Gly Gly Asp Lys Ala Ser Thr Gln
65                  70                  75                  80

Lys Ala Ile Asp Glu Ile Thr Thr Lys Ile Asn Asn Ile Ile Glu Lys
                85                  90                  95

Gly Gly Gly Val Gly Ser Asn Leu Glu Asp Pro Ala Ser Gly Gly Gly
            100                 105                 110

Asp Lys Ala Ser Thr Gln Lys Ala Ile Asp Glu Ile Thr Thr Lys Ile
            115                 120                 125

Asn Asn Ile Ile Glu Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
            195                 200                 205

Gly Arg Ser Pro Arg Arg Arg Thr Pro Ser Pro Arg Arg Arg Arg Ser
```

210                 215                 220
Gln Ser Pro Arg Arg Arg Ser Gln Ser Arg Glu Ser Gln Cys
225                 230                 235

<210> SEQ ID NO 67
<211> LENGTH: 239
<212> TYPE: PRT
<213> ORGANISM: Artificial Sequence
<220> FEATURE:
<223> OTHER INFORMATION: Synthetic

<400> SEQUENCE: 67

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Lys Glu Ala Thr Gln
65              70                  75                  80

Lys Ala Val Asp Ala Ile Thr Asn Lys Val Asn Ser Ile Ile Asp Lys
                85                  90                  95

Gly Gly Gly Val Gly Ser Asn Leu Glu Asp Pro Ala Ser Gly Gly
            100                 105                 110

Asp Lys Glu Ala Thr Gln Lys Ala Val Asp Ala Ile Thr Asn Lys Val
        115                 120                 125

Asn Ser Ile Ile Asp Lys Gly Gly Arg Glu Leu Val Val Ser Tyr
    130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                165                 170                 175

Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Ser Gln Ser Arg Glu Ser Gln Cys
225                 230                 235

<210> SEQ ID NO 68
<211> LENGTH: 239
<212> TYPE: PRT
<213> ORGANISM: Artificial Sequence
<220> FEATURE:
<223> OTHER INFORMATION: Synthetic

<400> SEQUENCE: 68

Met Asp Ile Asp Pro Tyr Lys Glu Phe Gly Ala Ser Val Glu Leu Leu
1               5                   10                  15

Ser Phe Leu Pro Ser Asp Phe Pro Ser Ile Arg Asp Leu Leu Asp
            20                  25                  30

Thr Ala Ser Ala Leu Tyr Arg Glu Ala Leu Glu Ser Pro Glu His Cys
        35                  40                  45

```
Ser Pro His His Thr Ala Leu Arg Gln Ala Ile Leu Cys Trp Gly Glu
    50                  55                  60

Leu Met Asn Leu Ala Thr Trp Gly Gly Asp Lys Glu Ala Thr Gln
65                  70                  75                  80

Lys Ala Val Asp Ala Ile Thr Thr Lys Val Asn Asn Ile Ile Asp Lys
                    85                  90                  95

Gly Gly Gly Val Gly Ser Asn Leu Glu Asp Pro Ala Ser Gly Gly Gly
                100                 105                 110

Asp Lys Glu Ala Thr Gln Lys Ala Val Asp Ala Ile Thr Thr Lys Val
            115                 120                 125

Asn Asn Ile Ile Asp Lys Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                    165                 170                 175

Ser Phe Gly Val Trp Ile Arg Thr Pro Pro Ala Tyr Arg Pro Pro Asn
                180                 185                 190

Ala Pro Ile Leu Ser Thr Leu Pro Glu Thr Thr Val Val Arg Arg Arg
                195                 200                 205

Gly Arg Ser Pro Arg Arg Thr Pro Ser Pro Arg Arg Arg Arg Ser
210                 215                 220

Gln Ser Pro Arg Arg Arg Arg Ser Gln Ser Arg Glu Ser Gln Cys
225                 230                 235

<210> SEQ ID NO 69
<211> LENGTH: 239
<212> TYPE: PRT
<213> ORGANISM: Artificial Sequence
<220> FEATURE:
<223> OTHER INFORMATION: Synthetic

<400> SEQUENCE: 69

Met Asp Ile Asp Pro Tyr Lys Glu Phe Gly Ala Ser Val Glu Leu Leu
1               5                   10                  15

Ser Phe Leu Pro Ser Asp Phe Phe Pro Ser Ile Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
    50                  55                  60

Leu Met Asn Leu Ala Thr Trp Gly Gly Asp Leu Lys Ser Thr Gln
65                  70                  75                  80

Glu Ala Ile Asn Lys Ile Thr Lys Asn Leu Asn Ser Leu Ser Glu Leu
                85                  90                  95

Gly Gly Gly Val Gly Ser Asn Leu Glu Asp Pro Ala Ser Gly Gly Gly
                100                 105                 110

Asp Leu Lys Ser Thr Gln Glu Ala Ile Asn Lys Ile Thr Lys Asn Leu
            115                 120                 125

Asn Ser Leu Ser Glu Leu Gly Gly Gly Arg Glu Leu Val Val Ser Tyr
130                 135                 140

Val Asn Val Asn Met Gly Leu Lys Ile Arg Gln Leu Leu Trp Phe His
145                 150                 155                 160

Ile Ser Cys Leu Thr Phe Gly Arg Glu Thr Val Leu Glu Tyr Leu Val
                    165                 170                 175
```

```
Ser Phe Gly Val Trp Ile Arg Thr Pro Pro Ala Tyr Arg Pro Pro Asn
            180                 185                 190

Ala Pro Ile Leu Ser Thr Leu Pro Glu Thr Thr Val Val Arg Arg Arg
        195                 200                 205

Gly Arg Ser Pro Arg Arg Arg Thr Pro Ser Pro Arg Arg Arg Arg Ser
    210                 215                 220

Gln Ser Pro Arg Arg Arg Arg Ser Gln Ser Arg Glu Ser Gln Cys
225                 230                 235
```

<210> SEQ ID NO 70
<211> LENGTH: 22
<212> TYPE: PRT
<213> ORGANISM: Influenza Virus

<400> SEQUENCE: 70

```
Asp Leu Lys Ser Thr Gln Asn Ala Ile Asp Glu Ile Thr Asn Lys Val
1               5                   10                  15

Asn Ser Val Ile Glu Lys
            20
```

<210> SEQ ID NO 71
<211> LENGTH: 22
<212> TYPE: PRT
<213> ORGANISM: Influenza Virus

<400> SEQUENCE: 71

```
Asp Gln Lys Ser Thr Gln Asn Ala Ile Asn Gly Ile Thr Asn Lys Val
1               5                   10                  15

Asn Ser Ile Ile Glu Lys
            20
```

<210> SEQ ID NO 72
<211> LENGTH: 22
<212> TYPE: PRT
<213> ORGANISM: Influenza Virus

<400> SEQUENCE: 72

```
Asp Gln Lys Ser Thr Gln Asn Ala Ile Asn Gly Ile Thr Asn Lys Val
1               5                   10                  15

Asn Ser Val Ile Glu Lys
            20
```

<210> SEQ ID NO 73
<211> LENGTH: 22
<212> TYPE: PRT
<213> ORGANISM: Influenza Virus

<400> SEQUENCE: 73

```
Asp Gln Lys Ser Thr Gln Asn Ala Ile Asn Gly Ile Thr Asn Lys Val
1               5                   10                  15

Asn Thr Val Ile Glu Lys
            20
```

<210> SEQ ID NO 74
<211> LENGTH: 22
<212> TYPE: PRT
<213> ORGANISM: Influenza Virus

<400> SEQUENCE: 74

```
Asp Lys Glu Ser Thr Gln Lys Ala Phe Asp Gly Ile Thr Asn Lys Val
1               5                   10                  15
```

```
Asn Ala Val Ile Glu Lys
            20

<210> SEQ ID NO 75
<211> LENGTH: 22
<212> TYPE: PRT
<213> ORGANISM: Influenza Virus

<400> SEQUENCE: 75

Asp Lys Glu Ser Thr Gln Lys Ala Phe Asp Gly Ile Thr Asn Lys Val
1               5                   10                  15

Asn Ser Val Ile Glu Lys
            20

<210> SEQ ID NO 76
<211> LENGTH: 22
<212> TYPE: PRT
<213> ORGANISM: Influenza Virus

<400> SEQUENCE: 76

Asp Leu Lys Ser Thr Gln Ala Ala Ile Asp Gln Ile Asn Gly Lys Leu
1               5                   10                  15

Asn Arg Leu Ile Gly Lys
            20

<210> SEQ ID NO 77
<211> LENGTH: 22
<212> TYPE: PRT
<213> ORGANISM: Influenza Virus

<400> SEQUENCE: 77

Asp Leu Lys Ser Thr Gln Ala Ala Ile Asp Gln Ile Asn Gly Lys Leu
1               5                   10                  15

Asn Arg Leu Val Glu Lys
            20

<210> SEQ ID NO 78
<211> LENGTH: 22
<212> TYPE: PRT
<213> ORGANISM: Influenza Virus

<400> SEQUENCE: 78

Asp Leu Lys Ser Thr Gln Ala Ala Ile Asp Gln Ile Asn Gly Lys Leu
1               5                   10                  15

Asn Arg Val Ile Glu Lys
            20

<210> SEQ ID NO 79
<211> LENGTH: 22
<212> TYPE: PRT
<213> ORGANISM: Influenza Virus

<400> SEQUENCE: 79

Asp Leu Lys Ser Thr Gln Ala Ala Ile Asn Gln Ile Asn Gly Lys Leu
1               5                   10                  15

Asn Arg Leu Ile Glu Lys
            20

<210> SEQ ID NO 80
<211> LENGTH: 22
<212> TYPE: PRT
<213> ORGANISM: Influenza Virus
```

-continued

<400> SEQUENCE: 80

Asp Leu Lys Ser Thr Gln Ala Ala Ile Asn Gln Ile Asn Gly Lys Leu
1               5                   10                  15

Asn Arg Leu Ile Gly Lys
            20

<210> SEQ ID NO 81
<211> LENGTH: 22
<212> TYPE: PRT
<213> ORGANISM: Influenza Virus

<400> SEQUENCE: 81

Asp Leu Lys Ser Thr Gln Ala Ala Ile Asn Gln Ile Thr Gly Lys Leu
1               5                   10                  15

Asn Arg Val Ile Lys Lys
            20

<210> SEQ ID NO 82
<211> LENGTH: 22
<212> TYPE: PRT
<213> ORGANISM: Influenza Virus

<400> SEQUENCE: 82

Asp Leu Lys Ser Thr Gln Ala Ala Ile Asp Gln Ile Asn Gly Lys Leu
1               5                   10                  15

Asn Arg Leu Ile Glu Lys
            20

<210> SEQ ID NO 83
<211> LENGTH: 22
<212> TYPE: PRT
<213> ORGANISM: Influenza Virus

<400> SEQUENCE: 83

Asp Lys Glu Ser Thr Gln Lys Ala Ile Asp Gly Ile Thr Asn Lys Val
1               5                   10                  15

Asn Ser Ile Ile Asp Lys
            20

<210> SEQ ID NO 84
<211> LENGTH: 22
<212> TYPE: PRT
<213> ORGANISM: Influenza Virus

<400> SEQUENCE: 84

Asp Lys Glu Ser Thr Gln Lys Ala Ile Asp Gly Val Thr Asn Lys Val
1               5                   10                  15

Asn Ser Ile Ile Asp Lys
            20

<210> SEQ ID NO 85
<211> LENGTH: 22
<212> TYPE: PRT
<213> ORGANISM: Influenza Virus

<400> SEQUENCE: 85

Asp Lys Glu Ser Thr Gln Lys Ala Ile Asp Gly Val Thr Asn Lys Val
1               5                   10                  15

Asn Ser Ile Ile Asn Lys
            20

-continued

```
<210> SEQ ID NO 86
<211> LENGTH: 22
<212> TYPE: PRT
<213> ORGANISM: Influenza Virus

<400> SEQUENCE: 86

Asp Tyr Lys Ser Thr Gln Ser Ala Ile Asp Gln Ile Thr Gly Lys Leu
1               5                   10                  15

Asn Arg Leu Ile Gly Lys
            20

<210> SEQ ID NO 87
<211> LENGTH: 22
<212> TYPE: PRT
<213> ORGANISM: Influenza Virus

<400> SEQUENCE: 87

Asp Tyr Lys Ser Thr Gln Ser Ala Ile Asp Gln Ile Thr Gly Lys Leu
1               5                   10                  15

Asn Arg Leu Ile Glu Lys
            20

<210> SEQ ID NO 88
<211> LENGTH: 22
<212> TYPE: PRT
<213> ORGANISM: Influenza Virus

<400> SEQUENCE: 88

Asp Gln Lys Ser Thr Gln Glu Ala Ile Asp Lys Ile Thr Asn Lys Val
1               5                   10                  15

Asn Asn Ile Val Asp Lys
            20

<210> SEQ ID NO 89
<211> LENGTH: 22
<212> TYPE: PRT
<213> ORGANISM: Influenza Virus

<400> SEQUENCE: 89

Asp Arg Asp Ser Thr Gln Lys Ala Ile Asp Lys Ile Thr Ser Lys Val
1               5                   10                  15

Asn Asn Ile Val Asp Lys
            20

<210> SEQ ID NO 90
<211> LENGTH: 22
<212> TYPE: PRT
<213> ORGANISM: Influenza Virus

<400> SEQUENCE: 90

Asp Arg Asp Ser Thr Gln Arg Ala Ile Asp Lys Ile Thr Ser Lys Val
1               5                   10                  15

Asn Asn Ile Val Asp Lys
            20

<210> SEQ ID NO 91
<211> LENGTH: 22
<212> TYPE: PRT
<213> ORGANISM: Influenza Virus

<400> SEQUENCE: 91

Asp Tyr Lys Ser Thr Gln Ala Ala Ile Asp Gln Ile Thr Gly Lys Leu
1               5                   10                  15
```

Asn Arg Ile Ile Lys Lys
            20

<210> SEQ ID NO 92
<211> LENGTH: 22
<212> TYPE: PRT
<213> ORGANISM: Influenza Virus

<400> SEQUENCE: 92

Asp Lys Glu Ser Thr Gln Thr Ala Ile Asp Gln Ile Thr Ser Lys Val
1               5                   10                  15

Asn Asn Ile Val Asp Arg
            20

<210> SEQ ID NO 93
<211> LENGTH: 22
<212> TYPE: PRT
<213> ORGANISM: Influenza Virus

<400> SEQUENCE: 93

Asp Arg Asp Ser Thr Gln Arg Ala Ile Asp Asn Met Gln Asn Lys Leu
1               5                   10                  15

Asn Asn Val Ile Asp Lys
            20

<210> SEQ ID NO 94
<211> LENGTH: 22
<212> TYPE: PRT
<213> ORGANISM: Influenza Virus

<400> SEQUENCE: 94

Asp Lys Glu Ser Thr Gln Lys Ala Ile Asp Gln Ile Thr Thr Lys Ile
1               5                   10                  15

Asn Asn Ile Ile Asp Lys
            20

<210> SEQ ID NO 95
<211> LENGTH: 22
<212> TYPE: PRT
<213> ORGANISM: Influenza Virus

<400> SEQUENCE: 95

Asp Tyr Lys Ser Thr Gln Ala Ala Ile Asp Gln Ile Thr Gly Lys Leu
1               5                   10                  15

Asn Arg Leu Ile Glu Lys
            20

<210> SEQ ID NO 96
<211> LENGTH: 22
<212> TYPE: PRT
<213> ORGANISM: Influenza Virus

<400> SEQUENCE: 96

Asp Lys Ala Ser Thr Gln Lys Ala Ile Asp Glu Ile Thr Thr Lys Ile
1               5                   10                  15

Asn Asn Ile Ile Glu Lys
            20

<210> SEQ ID NO 97
<211> LENGTH: 22
<212> TYPE: PRT
<213> ORGANISM: Influenza Virus

```
<400> SEQUENCE: 97

Asp Lys Glu Ala Thr Gln Lys Ala Val Asp Ala Ile Thr Asn Lys Val
1               5                   10                  15

Asn Ser Ile Ile Asp Lys
            20

<210> SEQ ID NO 98
<211> LENGTH: 22
<212> TYPE: PRT
<213> ORGANISM: Influenza Virus

<400> SEQUENCE: 98

Asp Lys Glu Ala Thr Gln Lys Ala Val Asp Ala Ile Thr Thr Lys Val
1               5                   10                  15

Asn Asn Ile Ile Asp Lys
            20

<210> SEQ ID NO 99
<211> LENGTH: 22
<212> TYPE: PRT
<213> ORGANISM: Influenza Virus

<400> SEQUENCE: 99

Asp Leu Lys Ser Thr Gln Glu Ala Ile Asn Lys Ile Thr Lys Asn Leu
1               5                   10                  15

Asn Ser Leu Ser Glu Leu
            20
```